United States Patent [19]

Nagao et al.

[11] Patent Number: 5,753,700
[45] Date of Patent: May 19, 1998

[54] NAPHTHYLOXYACETIC ACID DERIVATIVES

[75] Inventors: Yuuki Nagao; Kazuhiko Torisu; Takayuki Maruyama, all of Mishima, Japan

[73] Assignee: Ono Pharmaceutical Co., Ltd., Osaka, Japan

[21] Appl. No.: 574,133

[22] Filed: Dec. 18, 1995

[30] Foreign Application Priority Data

Dec. 28, 1994 [JP] Japan ................... 6-337651

[51] Int. Cl.[6] ..................................... A61K 31/24
[52] U.S. Cl. .................. 514/539; 560/21; 562/441
[58] Field of Search ................... 562/441; 514/539, 514/411; 548/444; 560/21

[56] References Cited

U.S. PATENT DOCUMENTS

| | | | |
|---|---|---|---|
| 3,930,672 | 1/1976 | Ozutsumi | 282/27.5 |
| 4,327,022 | 4/1982 | Bailey | 260/239 B |
| 4,780,469 | 10/1988 | Toda et al. | 514/382 |
| 5,344,836 | 9/1994 | Hamanaka et al. | 514/332 |

FOREIGN PATENT DOCUMENTS

| | | |
|---|---|---|
| A0512399 | 11/1992 | European Pat. Off. . |
| A0542203 | 5/1993 | European Pat. Off. . |
| A0603953 | 6/1994 | European Pat. Off. . |
| A2413986 | 11/1974 | Germany . |
| A899714 | 6/1962 | United Kingdom . |
| A8404245 | 11/1984 | WIPO . |

OTHER PUBLICATIONS

Chemical Abstracts, vol. 107, No. 23, 7 Dec. 1987.
Synthesis, No. 5, 1983, Stuttgart, Germany, pp. 385–386.
Chemical Abstracts, vol. 94, No. 15, 13 Apr. 1981.
Journal of Medicinal Chemistry, vol. 37, No. 20, 1994, Wash, Us, pp. 3231–3239.
Journal of Medicinal Chemistry, vol. 34, No. 8, 1991, Wash. US, p. 2504–2529.
Journal of Organic Chemistry, vol. 52, No. 15, 1987, Easton, US, pp. 3181–3185.
Chemical Abstracts, vol. 99, No. 13, 26 Sep. 1983.
Chemical Abstracts, vol. 91, No. 14, 1 Oct. 1979.
Chemical Abstracts, vol. 83, No. 25, 22 Dec. 1975.
Chemical Abstracts, vol. 82, No. 5, 3 Feb. 1975.

*Primary Examiner*—Amelia Owens
*Attorney, Agent, or Firm*—Watson Cole Stevens Davis, P.L.L.C.

[57] ABSTRACT

A naphthyloxyacetic acid derivative of the formula (I)

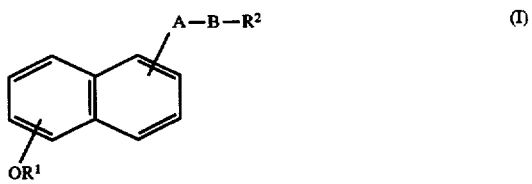

wherein $R^1$ is H, alkyl, alkylene-($-COOR^{10}$, $-OH$, $-CONR^4R^5$, $-CONR^6$-alkylene-OH, $-NR^4R^5$, -cyano or -tetrazolyl); A is single bond, alkylene, alkenylene, $-S$-alkylene, $-O$-alkylene; B is $NR^3CO$, $CONR^3$; $R^2$ is (1) alkyl (2) alkenyl, (3) alkyl or alkenyl substituted by 1–3 of phenyl, cycloalkyl, naphthyl and heterocyclic ring containing nitrogen atom (the said ring may be substituted by 1–3 of alkyl, alkoxy and halogen etc.), (4) $NR^7R^8$ or (5) alkylene-$NR^7R^8$; non-toxic salt thereof, non-toxic acid addition salt thereof and hydrate thereof can bind the $PGE_2$ receptor and exhibits the activity to antagonize or agonize for $PGE_2$, therefore, they are useful as $PGE_2$ antagonist or $PGE_2$ agonist.

4 Claims, No Drawings

NAPHTHYLOXYACETIC ACID DERIVATIVES

SUMMARY

This invention is related to naphthyloxyacetic acid derivatives. More particularly, this invention is related to (1) naphthyloxyacetic acid derivatives of the formula (I)

[Structure: naphthalene with $A-B-R^2$ substituent and $OR^1$ substituent] (I)

wherein all the symbols are the same meaning as hereafter defined, non-toxic salts thereof, non-toxic acid addition salts and hydrates thereof, (2) processes for the preparation thereof and (3) prostaglandin $E_2$ ($PGE_2$) antagonists or agonists which comprise them as an active ingredient.

BACKGROUND

As $PGE_2$ agonist, many compounds have been known including $PGE_2$ per se. However, no compounds which antagonize for $PGE_2$ or inhibit $PGE_2$ activity ($PGE_2$ antagonist) have been known until now.

$PGE_2$ has been known as metabolite in the arachidonate cascade. It has been known that $PGE_2$ has uterine contractile activity, pain-inducing effect, promoting effect of digestive peristalsis, awaking effect, suppressive effect of gastric acid secretion, hypotensive activity, blood platelet inhibition activity etc. It is expected that the following activities are possessed according to antagonizing or agonizing these activities of $PGE_2$.

To antagonize $PGE_2$ means to suppress the effects above mentioned, so $PGE_2$ antagonists are considered to inhibit uterine contraction, to have analgesic action, to inhibit digestive peristalsis, to induce sleep. Therefor, $PGE_2$ antagonists are considered to be useful for the prevention of abortion, or as analgesics, antidiarrheals or sleep inducer.

To agonize for $PGE_2$ means to promote the effects above mentioned, so $PGE_2$ agonists are considered to stimulate uterine contraction, to promote digestive peristalsis, to suppress gastric acid secretion, to lower blood pressure or to inhibit blood platelet aggregation. Therefor, $PGE_2$ agonists are considered to be useful as abortient, cathartics, and antiulcer, anti-gastritis, antihypertensive or antithrombosis agents.

RELATED ART

Japanese Patent Application Kokai Hei 6-72978 or U.S. Pat No. 5,344,836 disclose that the fused benzeneoxyacetic acid derivatives of the formula (A).

[Structure (A): fused bicyclic ring with $B^A-A^A$, $D^A$, and $O-COOR^{1A}$ groups]

wherein

[Structures showing various ring systems with $B^A$, $D^A$, $(CH_2)_p$, $(CH2)_e$, $CH=CH-(CH_2)_q$, $(CH_2)_r$, $CH-(CH_2)_r$, $(CH2)_f$ groups]

$A^A$ is
  (i) $-COW^A$,
  (ii) $-NR^{4A}-Y^A$ or
  (iii) $-Z^A-NR^{4A}-CONR^{2A}R^{3A}$;

$W^A$ is
  (i) $-NR^{2A}R^{3A}$,
  (ii) $-NR^{4A}-OR^{5A}$,
  (iii) $-NR^{4A}-NR^{2A}R^{3A}$ or
  (iv) $-NR^{4A}-N=CR^{2A}R^{3A}$;

$Y^A$ is
  (i) $-CO-R^{5A}$,
  (ii) $-CO-U^A-NR^{2A}R^{3A}$ or
  (iii) $-CS-U^A-NR^{2A}R^{3A}$;

$Z^A$ is
  (i) $-CH=N-$ or
  (ii) $-CH_2-NR^{6A}-$;

$R^{1A}$ is hydrogen atom or C1–4 alkyl;

$R^{2A}$ and $R^{3A}$ each, independently, is
  (i) hydrogen atom,
  (ii) phenyl,
  (iii) benzoylphenyl,
  (iv) 4–7 membered, unsaturated monocyclic hetero ring containing one nitrogen atom as hetero atom or
  (v) C1–4 alkyl substituted by 1–3 rings optionally selected from 4–7 membered, unsaturated monocyclic hetero ring containing one nitrogen atom as hetero atom, and phenyl;

$R^{4A}$ is hydrogen atom, C1–6 alkyl or phenyl;

$R^{5A}$ is
  (i) phenyl,
  (ii) 4–7 membered, unsaturated monocyclic hetero ring containing one nitrogen atom as hetero atom or
  (iii) C1–4 alkyl substituted by 1–3 rings optionally selected from 4–7 membered, unsaturated monocyclic hetero ring containing one nitrogen atom as hetero atom, and phenyl;

$R^{6A}$ is hydrogen atom, C1–6 alkyl or phenyl;

$U^A$ is single bond or C1–4 alkylene;

the said phenyl and hetero rings may be also substituted by C1–4 alkyl, C1–4 alkoxy, halogen atom, nitro or trihalomethyl, when $R^{2A}$, $R^{3A}$, $R^{4A}$, $R^{5A}$ or $R^{6A}$ is phenyl or the group containing phenyl, and when $R^{2A}$, $R^{3A}$ or $R^{5A}$ is the said hetero ring or the group containing the hetero ring;

e is integer of 3–5;
f is integer of 1–3;
p is zero or integer of 1–4;
q is zero or integer of 1–2;
r is zero or integer of 1–4;
s is zero or integer of 1–3;

with the proviso that, when $A^A$ is (ii) —N—$R^{4A}$—$Y^A$ (in which $R^{4A}$ and $Y^A$ are the same meaning as hereinbefore defined), q, r, or s is not zero; and that when

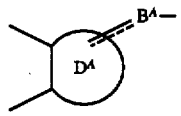

is the formula (iii) or (iv), —(CH$_2$)r or =CH—(CH$_2$)s in the side chain should be bonded to the carbon atom at the position a or b in the ring can bind the PGI$_2$ receptor and that they are useful as medicine.

Comparison with the Related Art

The compounds disclosed in the above Japanese Patent Application Kokai Hei 6-72978 or U.S. Pat No. 5,344,836 are different in structure from the compounds of the present invention in view of the point that the naphthalene ring as basic skeleton in the former compounds is always partially saturated. It is disclosed that the activity of these compounds is as PGI$_2$ antagonist or agonist.

As apparent to the ordinary skilled person in the art, PGE$_2$ and PGI$_2$ belong to the common PG family, but their activities are entirely different from each other. Therefore, naturally, the activities and effectiveness of the compounds which antagonize or agonize PGE$_2$ are different from those of the compounds which antagonize or agonize PGI$_2$. So, it is not possible to predict that the compounds of the present invention possesses PGE$_2$ antagonist or agonist activities from the disclosure of Japanese Patent Application Kokai Hei 6-72978 or U.S. Pat. No. 5,344,836.

DISCLOSURE OF THE INVENTION

The present invention is related to
(1) naphthyloxyacetic acid derivatives of the formula (I)

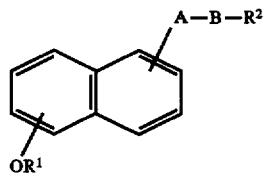

wherein
$R^1$ is
  (i) hydrogen,
  (ii) C1–4 alkyl,
  (iii) (C1–4 alkylene)-COOR$^{10}$ in which R$^{10}$ is hydrogen or C1–4 alkyl,
  (iv) (C1–4 alkylene)-OH,
  (v) (C1–4 alkylene)-CONR$^4$R$^5$ in which R$^4$ and R$^5$ each, independently, is hydrogen or C1–4 alkyl,
  (vi) (C1–4 alkylene)-CONR$^6$-(C1–4 alkylene)-OH in which R$^6$ is hydrogen or C1–4 alkyl,
  (vii) (C1–4 alkylene)-NR$^4$R$^5$ in which R$^4$ and R$^5$ are the same meaning as defined hereinbefore,
  (viii) (C1–4 alkylene)-cyano or
  (ix) (C1–4 alkylene)-tetrazolyl, A is single bond, C1–6 alkylene, C2–6 alkenylene, —S-(C1–6 alkylene) or —O-(C1–6 alkylene), B is NR$^3$CO or CONR$^3$ in which R$^3$ is hydrogen or C1–4 alkyl, and R$^2$ is
  (i) C1–6 alkyl,
  (ii) C2–6 alkenyl,
  (iii) C1–6 alkyl substituted by 1–3 of substituent(s) selected from the group consisting of phenyl, C4–7 cycloalkyl, naphthyl and 4–7 membered heterocyclic ring containing one nitrogen atom,
  (iv) C2–6 alkenyl substituted by 1–3 of substituent(s) selected from the group consisting of phenyl, C4–7 cycloalkyl, naphthyl and 4–7 membered heterocyclic ring containing one nitrogen atom,
  (v) NR$^7$R$^8$ in which R$^7$ and R$^8$ each, independently, is phenyl, C4–7 cycloalkyl, naphthyl or 4–7 membered heterocyclic ring containing one nitrogen atom, or
  (vi) (C1–6 alkylene)-NR$^7$R$^8$ in which R$^7$ and R$^8$ are the same meaning as defined hereinbefore, with the proviso that the ring in R$^2$ may be substituted by 1–3 of C1–4 alkyl, C1–4 alkoxy, halogen, nitro or trifluoromethyl;

or non-toxic salts thereof, non-toxic acid addition salts thereof and hydrates thereof, (2) processes for the preparation thereof, and
(3) PGE$_2$ antagonists or agonists which comprise them as an active ingredient.

In the formula (I), C1–4 alkyl represented by R$^1$, R$^3$, R$^4$, R$^5$, R$^6$ and R$^{10}$, and in R$^2$ means methyl, ethyl, propyl, butyl and isomeric groups thereof.

In the formula (I), the C1–4 alkoxy in R$^2$ means methoxy, ethoxy, propoxy, butoxy and isomeric groups thereof.

In the formula (I), C1–4 alkylene in R$^1$ means methylene, ethylene, trimethylene, tetramethylene and isomeric groups thereof.

In the formula (I), the C1–6 alkylene represented by A and in A means methylene, ethylene, trimethylene, tetramethylene, pentamethylene, hexamethylene and isomeric groups thereof.

In the formula (I), the C2–6 alkenylene represented by A means the above mentioned alkylene having 1–3 of double bond and, for example vinylene, propenylene, butenylene, pentenylene and hexenylene etc.

In the formula (I), C1–6 alkyl represented by R$^2$ means methyl, ethyl, propyl, butyl, pentyl, hexyl and isomeric groups thereof.

In the formula (I), C2–6 alkenyl represented by R$^2$ and in R$^2$ means the above mentioned alkyl having 1–3 of double bond and, for example, vinyl, propenyl, butenyl, pentenyl, hexenyl etc.

In the formula (I), C4–7 cycloalkyl in R$^2$ means cyclobutyl, cyclopentyl, cyclohexyl, cyclohepthyl.

In the formula (I), 4–7 membered heterocyclic ring containing one nitrogen atom in R$^2$ may be saturated or unsaturated. As such a ring, for example, azete, pyrrole, pyrroline, pyrrolidine, pyridine, pyridoline, pyridolidine, piperidine, azepine, azoline and azolidine etc. are listed.

In the formula (I), the halogen in R$^2$ means chlorine, bromine, fluorine and iodine.

As for $R^2$, the group which does not contain any 4–7 membered heterocyclic ring containing one nitrogen atom, for example, (i) C1–6 alkyl,
(ii) C2–6 alkenyl,
(iii-a) C1–6 alkyl substituted by 1–3 of substituent(s) selected from the group consisting of phenyl, C4–7 cycloalkyl and naphthyl,
(iv-a) C2–6 alkenyl substituted by 1–3 of substituent(s) selected from the group consisting of phenyl, C4–7 cycloalkyl and naphthyl,
(v-a) $NR^{7a}R^{8a}$ in which $R^{7a}$ and $R^{8a}$ each, independently, is phenyl, C4–7 cycloalkyl or naphthyl or
(vi-a) (C1–6 alkylene)-$NR^{7a}R^{7a}$ in which $R^{7a}$ and $R^{8a}$ are the same meaning as defined hereinbefore, is preferable.

In addition, as for $R^2$, the group which essentially contains one 4–7 membered heterocyclic ring containing one nitrogen atom, for example, (iii-b) C1–6 alkyl substituted by one 4–7 membered heterocyclic ring containing one nitrogen atom as essential substituent and no additional or one or two additional group(s) selected from phenyl, C4–7 cycloalkyl, naphthyl and 4–7 membered heterocyclic ring containing one nitrogen atom as another substituent,
(iv-b) C2–6 alkenyl substituted by one 4–7 membered heterocyclic ring containing one nitrogen atom as essential substituent and no additional or one or two additional group(s) selected from phenyl, C4–7 cycloalkyl, naphthyl and 4–7 membered heterocyclic ring containing one nitrogen atom as another substituent,
(v-b) $NR^{7b}R^{8b}$ in which one of $R^{7b}$ and $R^{8b}$ is phenyl, C4–7 cycloalkyl, naphthyl or 4–7 membered heterocyclic ring containing one nitrogen atom and the other is 4–7 membered heterocyclic ring containing one nitrogen atom or
(vi-b) (C1–6 alkylene)- $NR^{7b}R^{8b}$ in which $R^{7b}$ and $R^{8b}$ are the same meaning as defined hereinbefore, is also preferable.

Unless otherwise, specified all isomers are included in the invention. For example, alkyl, alkylene and alkenylene includes straight-chain or branched-chain ones. Double bond in alkenylene include structure of configurations E, Z and EZ mixtures. Isomers generated by asymmetric carbon (s) e.g. branched alkyl are also included within the present invention.

Salts, Acid addition salts and Hydrates

The compounds of the formula (I) may be converted into the corresponding salts by known methods. Non-toxic and water-soluble salts are preferable. Suitable salts, for example, are follows: salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris, (hydroxymethyl)aminomethane, lysine, arginine, N-methyl-D-glucamine etc.).

The compounds of the formula (I) may be converted into the corresponding acid additional salts by methods known per se. Non-toxic and water-soluble acid addition salts are preferable. Suitable acid addition salts, for example, are salts of inorganic acids, e.g., hydrochloride, hydrobromide, sulphate, phosphate, nitrate etc., or salts of organic acids, e.g., acetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of the formula (I), salts thereof or acid additional salts thereof may be converted into hydrates thereof by methods known per se.

Preferable compounds

In the compounds of the formula (I) of the present invention, the compounds described in Example and the following Tables 1–49 are preferable, particularly.

TABLE 1

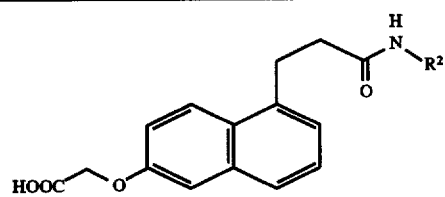

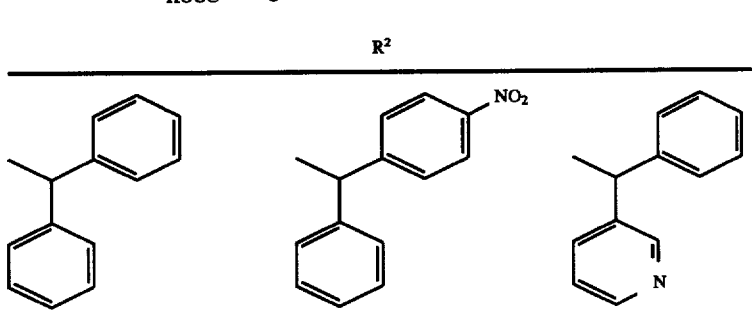

TABLE 1-continued
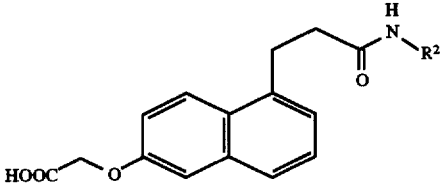
R²
 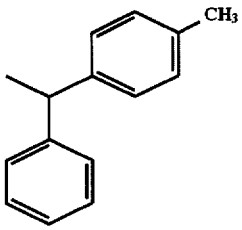
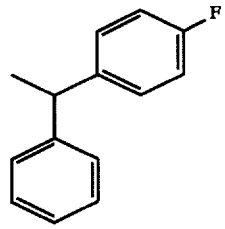 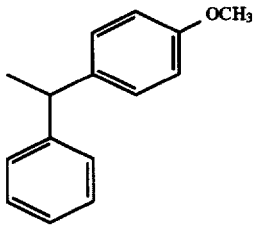
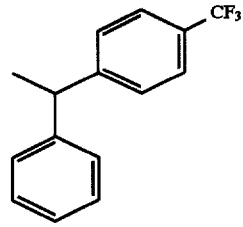 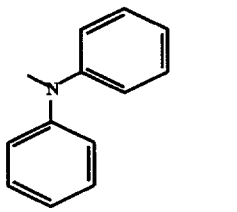 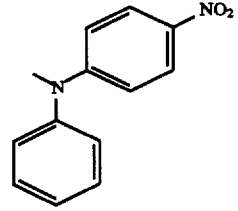
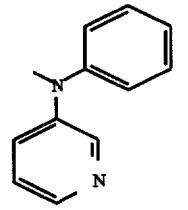 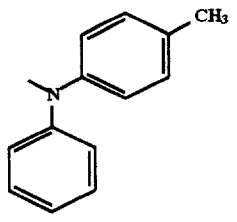
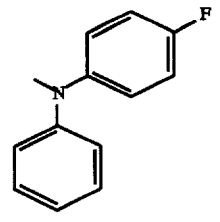 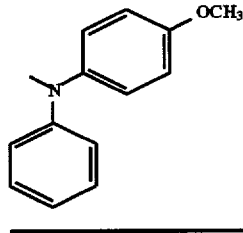

TABLE 2

TABLE 3
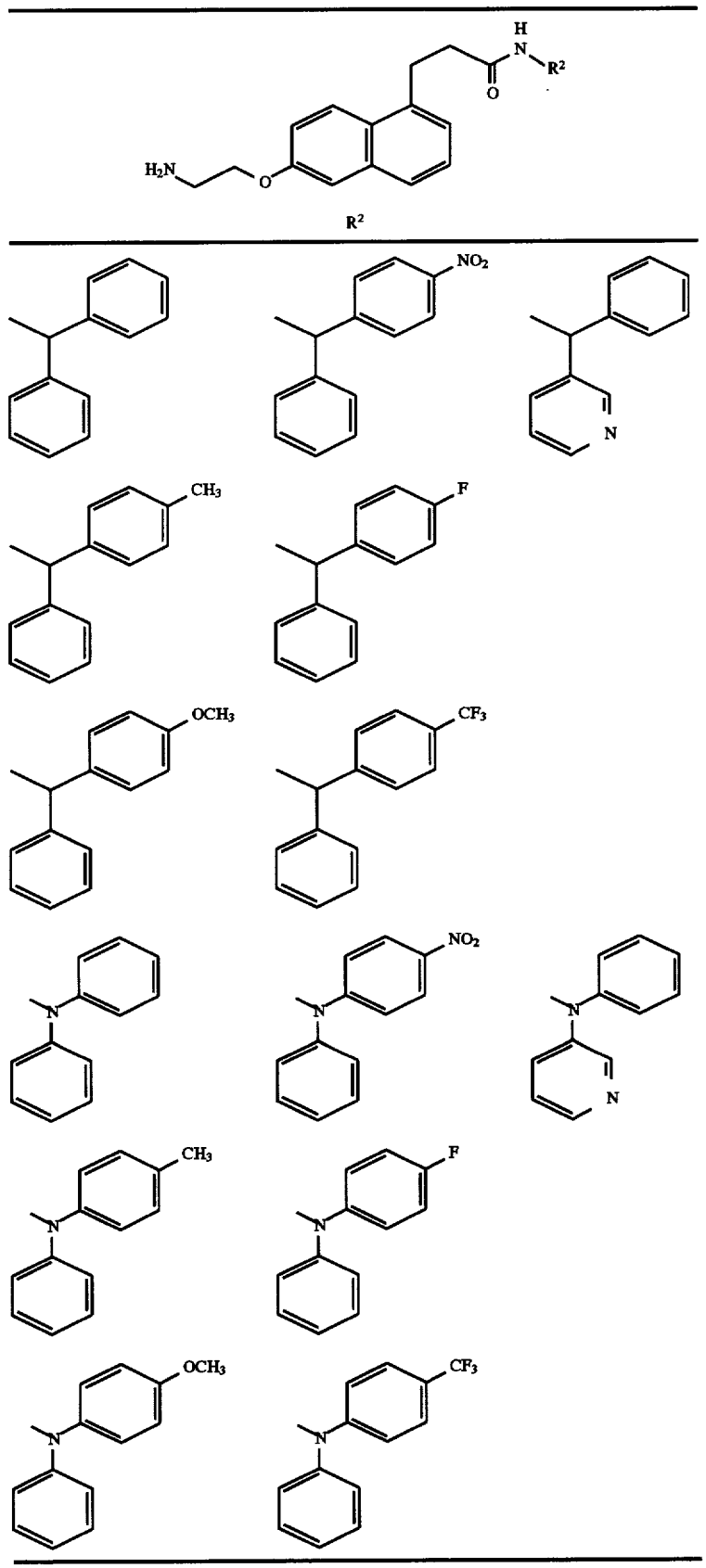

TABLE 4
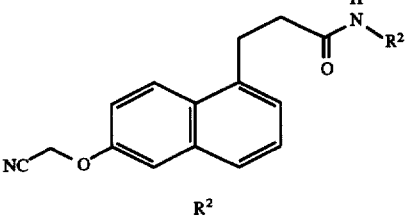

TABLE 5
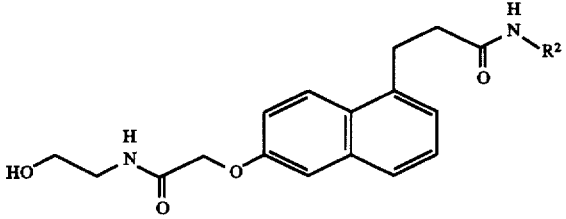

TABLE 5-continued
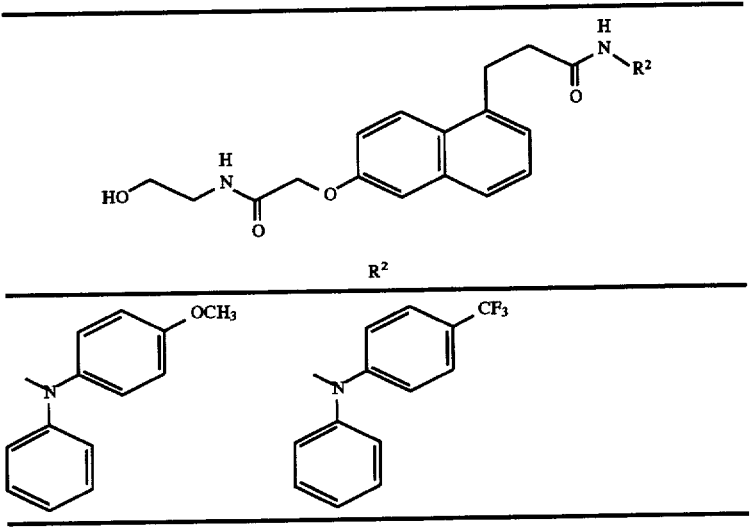
TABLE 6
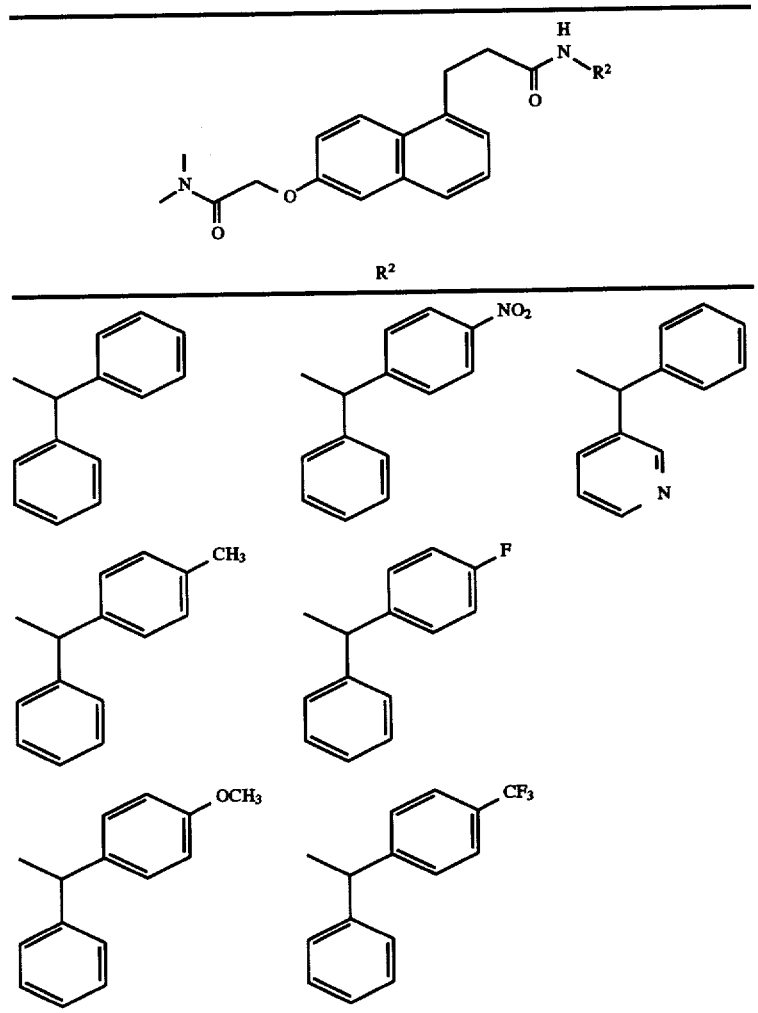

TABLE 6-continued
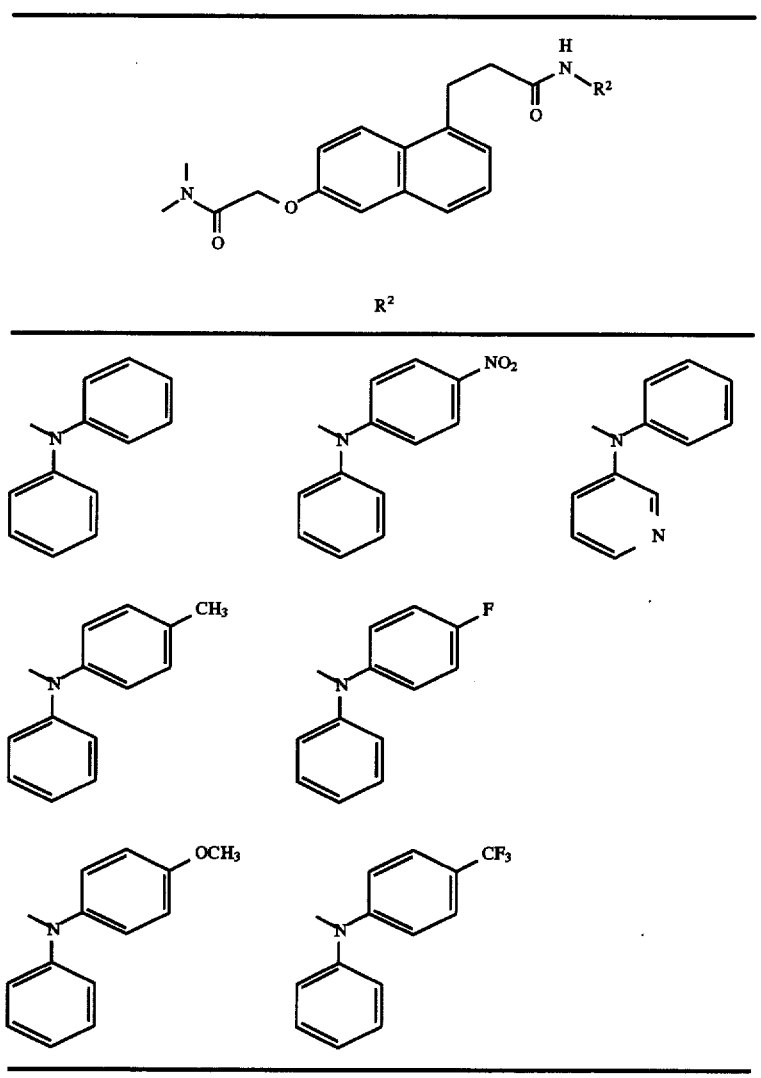
TABLE 7
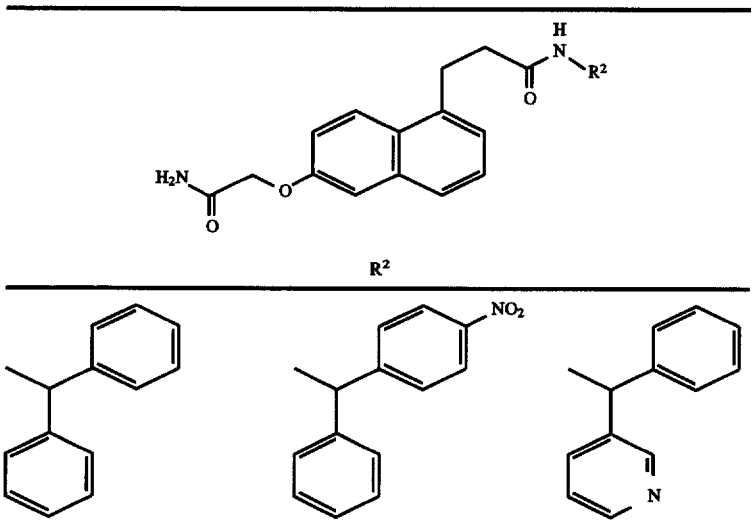

TABLE 7-continued
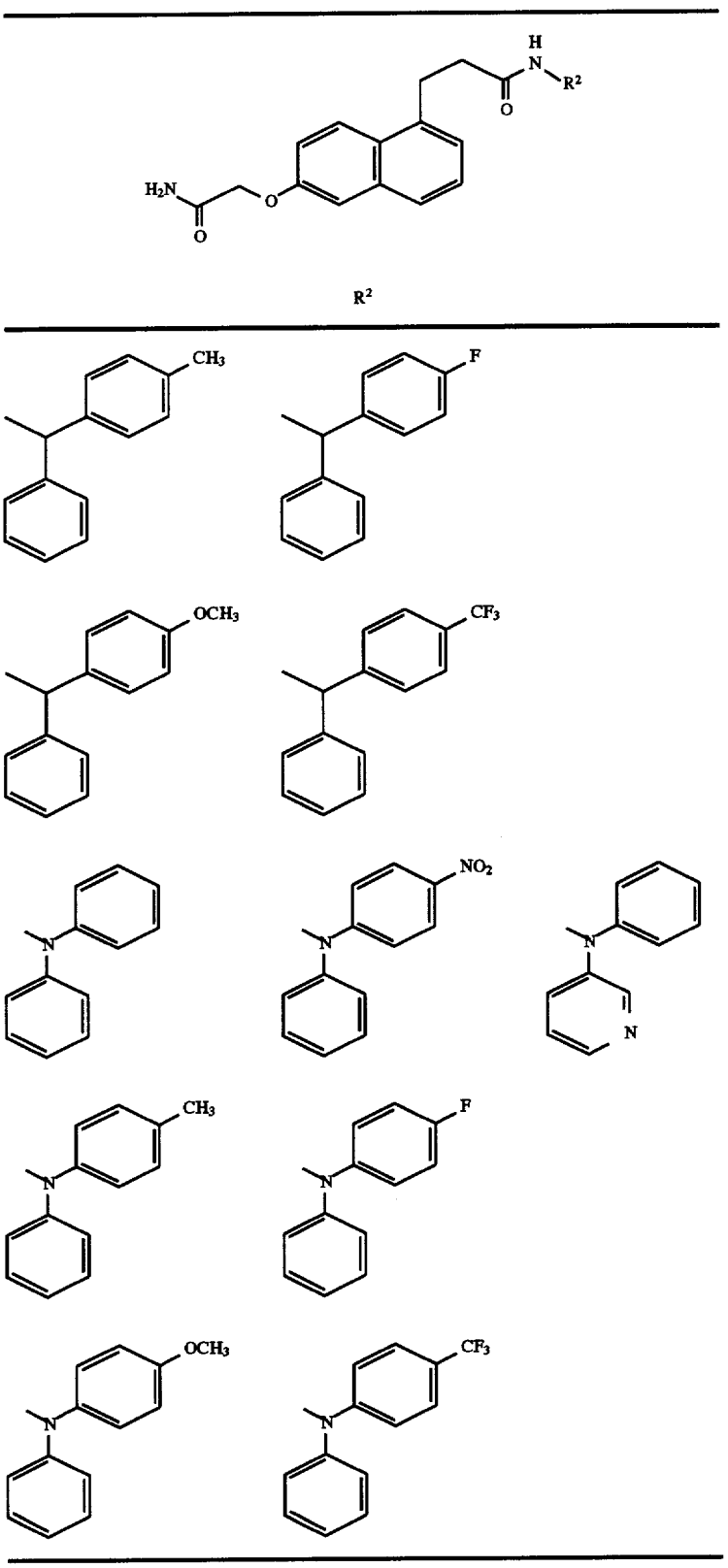
R²

TABLE 8
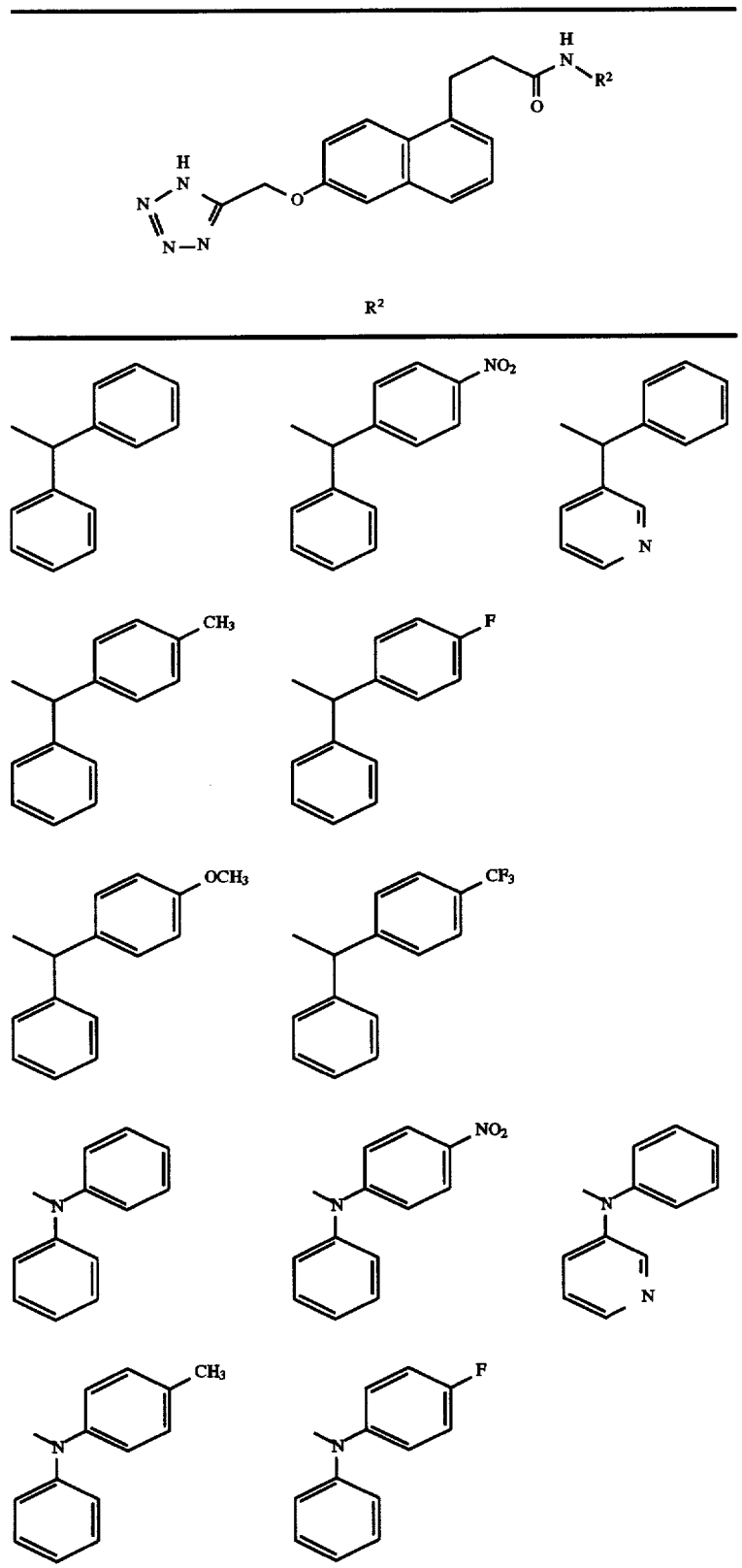

TABLE 8-continued
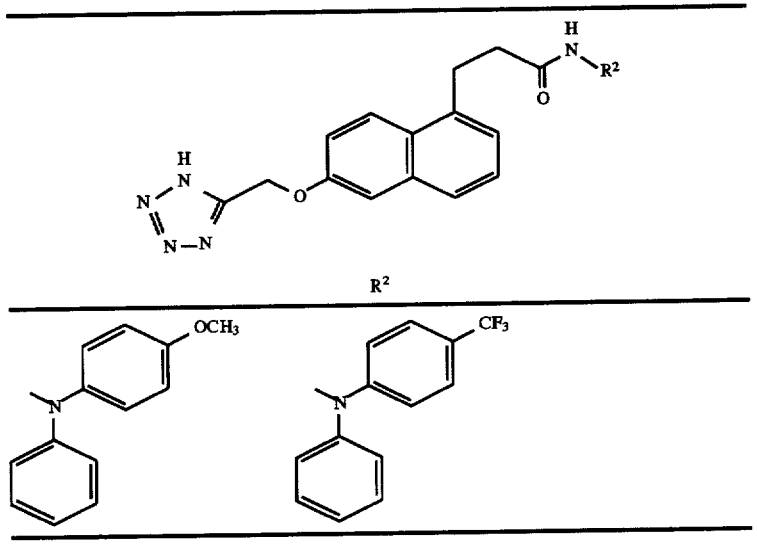
TABLE 9
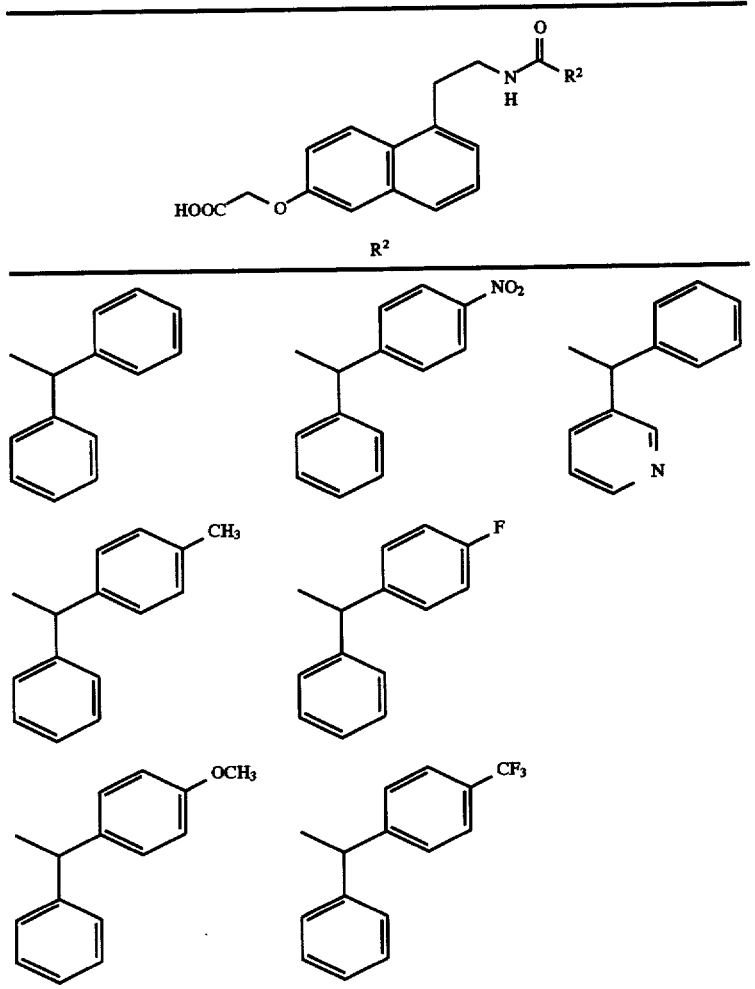

TABLE 9-continued

[Structure: naphthalene with HOOC-CH2-O- substituent and -CH2CH2-NH-C(=O)-R² substituent]

R²

[Structures of R² groups:]
- N(CH3)(phenyl)(phenyl)
- N(CH3)(4-NO2-phenyl)(phenyl)
- N(CH3)(3-pyridyl)(phenyl)
- N(CH3)(4-CH3-phenyl)(phenyl)
- N(CH3)(4-F-phenyl)(phenyl)
- N(CH3)(4-OCH3-phenyl)(phenyl)
- N(CH3)(4-CF3-phenyl)(phenyl)

TABLE 10

[Structure: naphthalene with HO-CH2CH2-O- substituent and -CH2CH2-NH-C(=O)-R² substituent]

R²

[Structures of R² groups:]
- CH(CH3)(phenyl)(phenyl)
- CH(CH3)(4-NO2-phenyl)(phenyl)
- CH(CH3)(phenyl)(3-pyridyl)

TABLE 10-continued
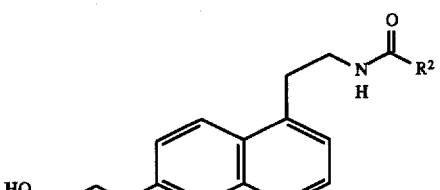
R²
 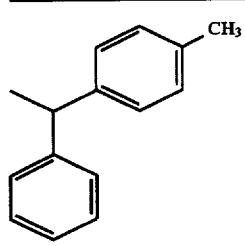
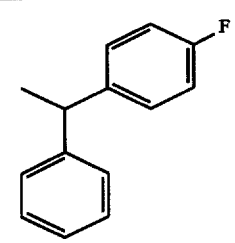 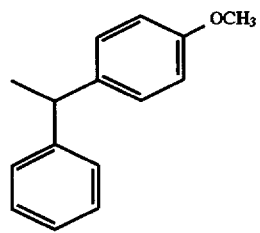
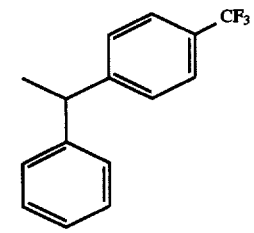 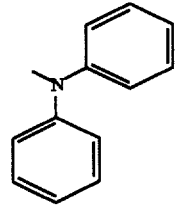 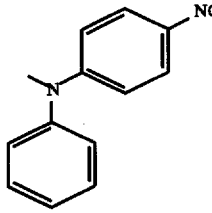
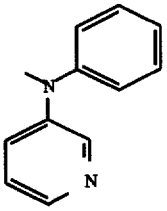 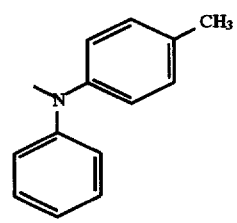
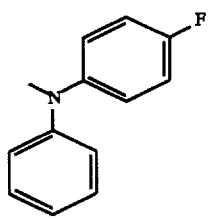 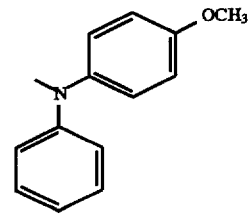

TABLE 11
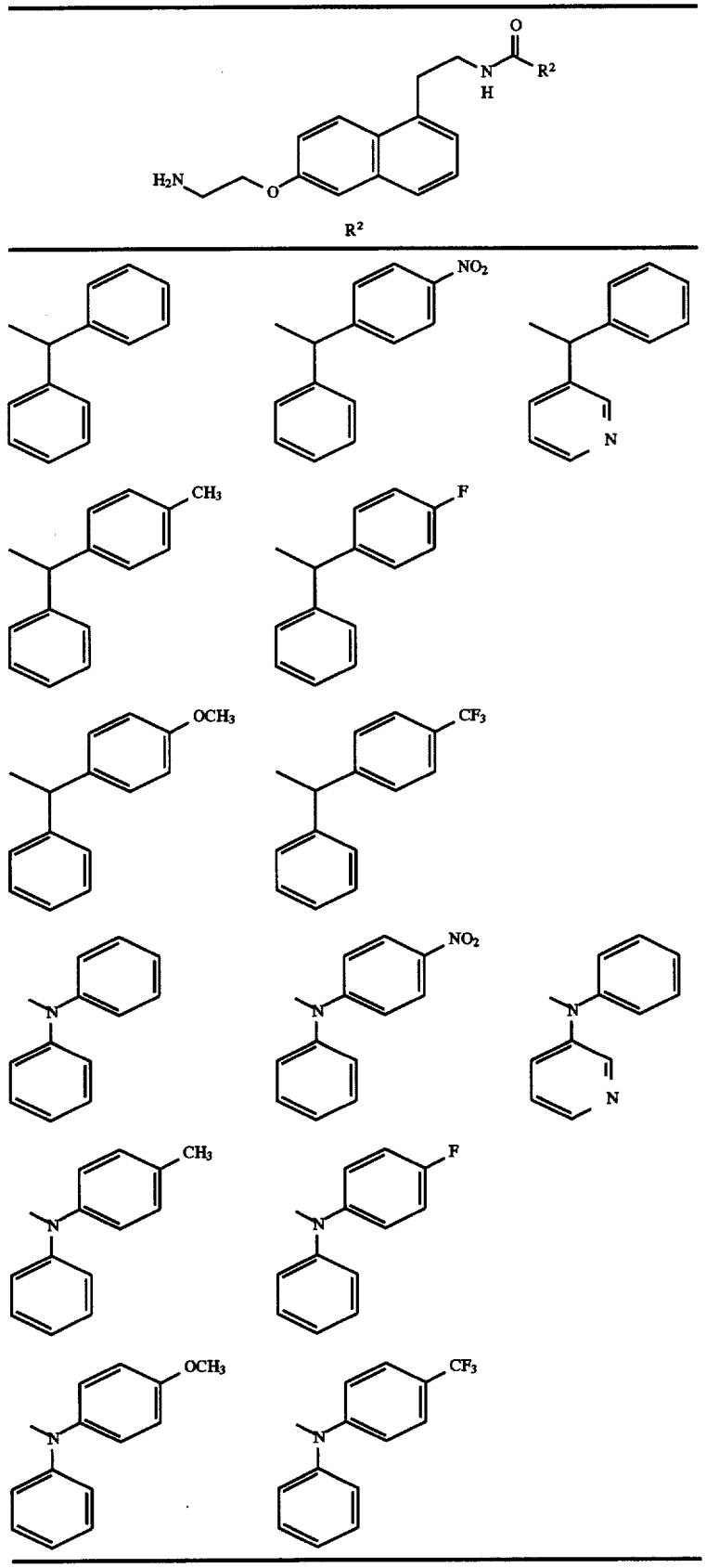

TABLE 12
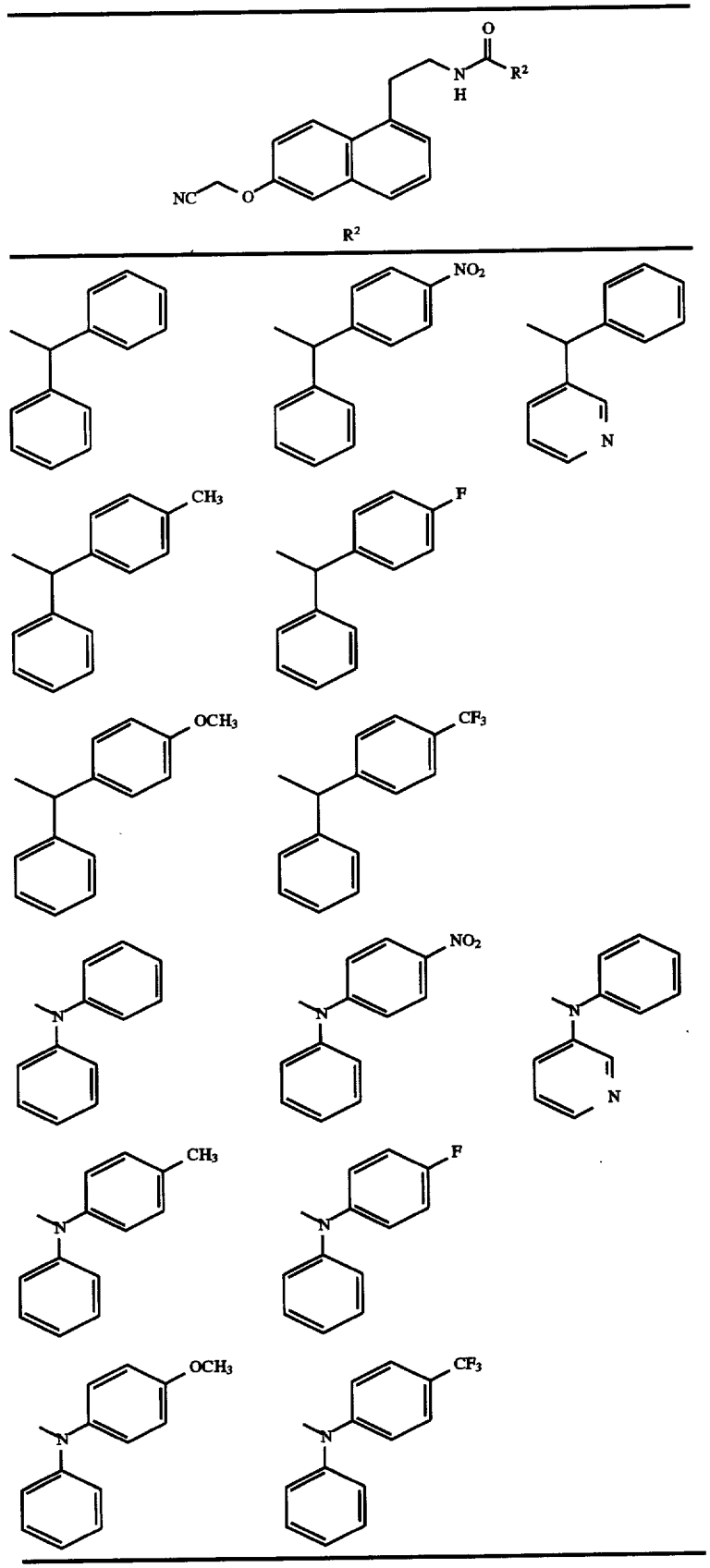

TABLE 13
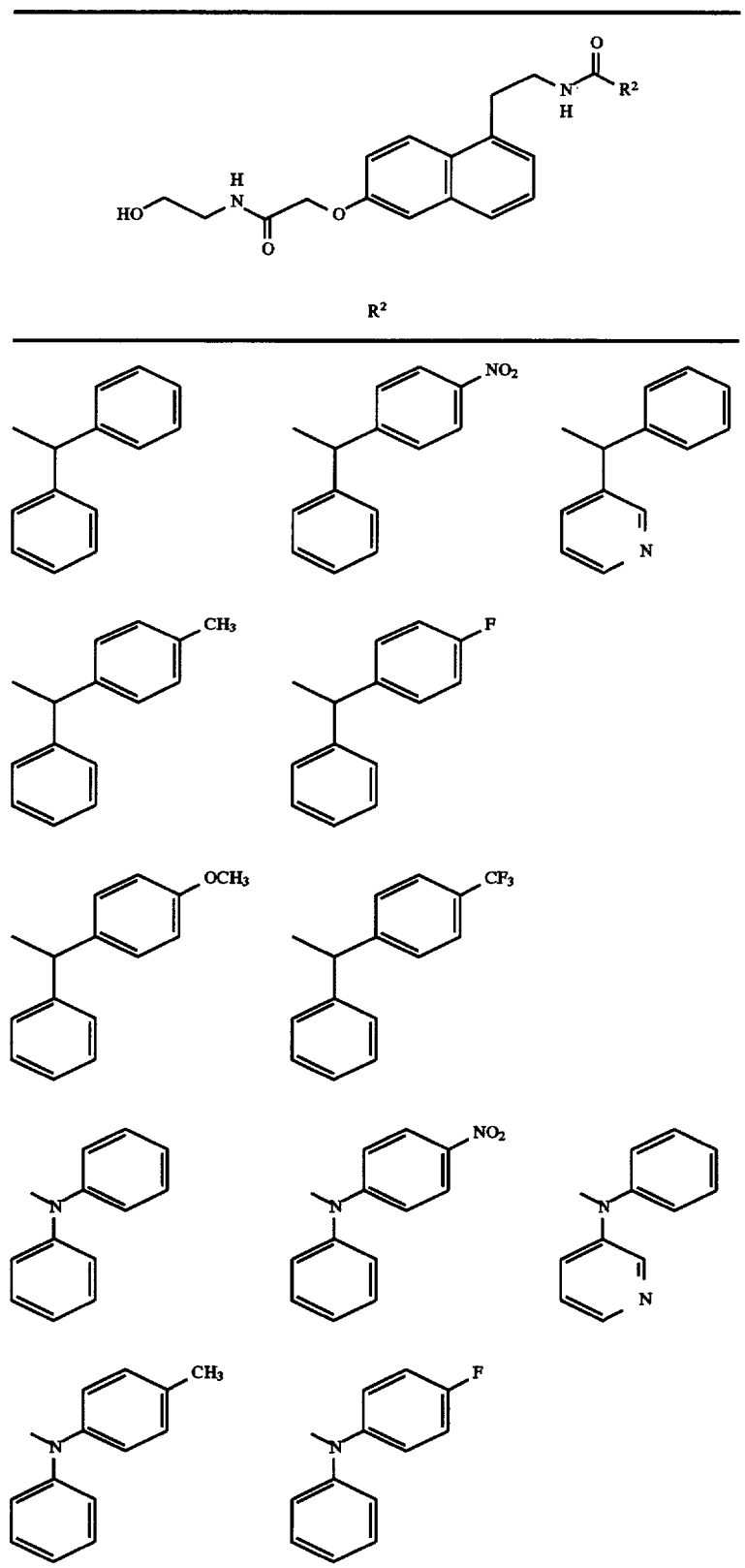

TABLE 13-continued
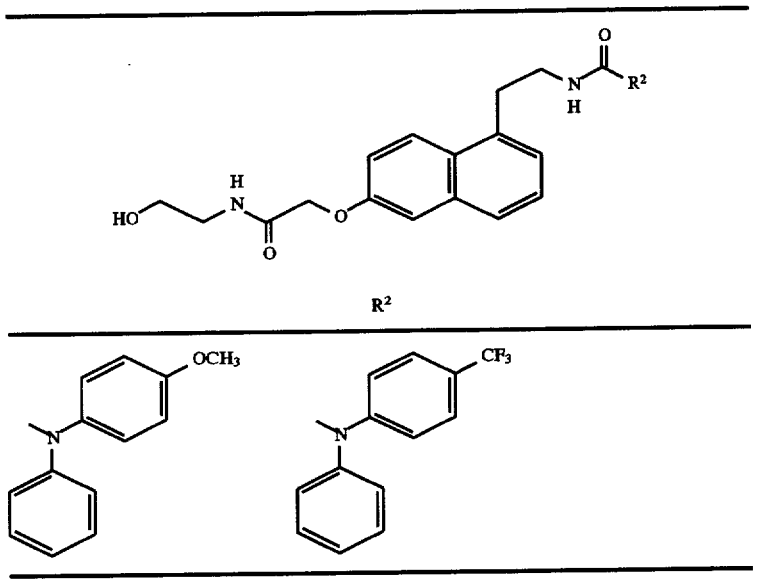
TABLE 14
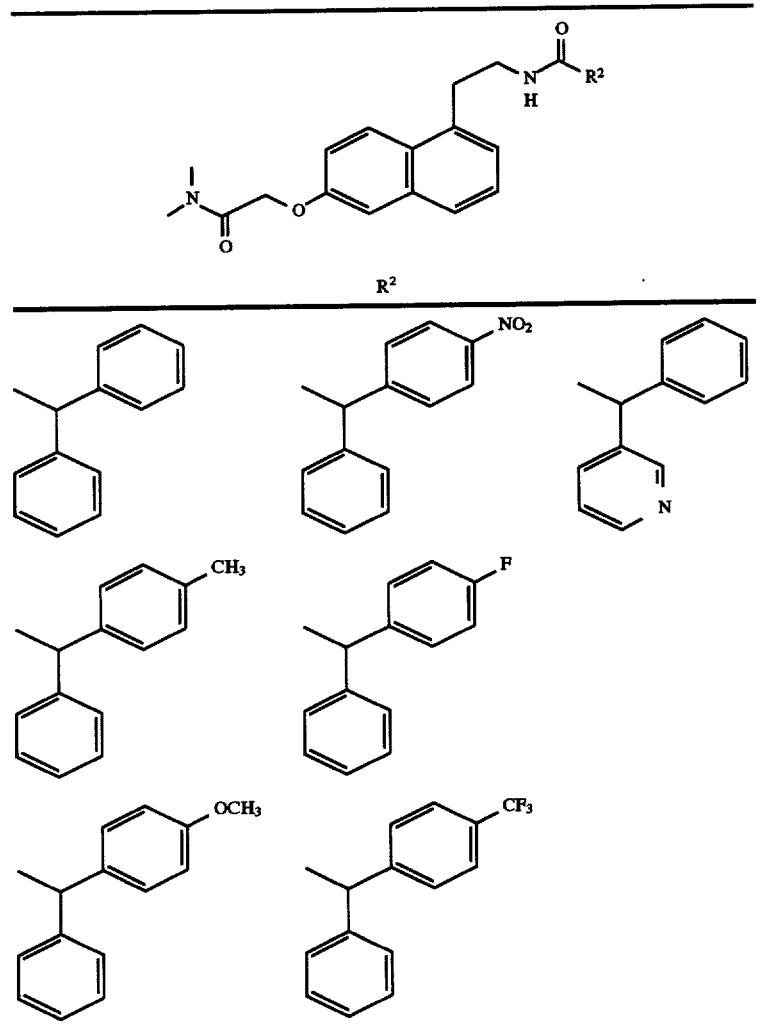

TABLE 14-continued
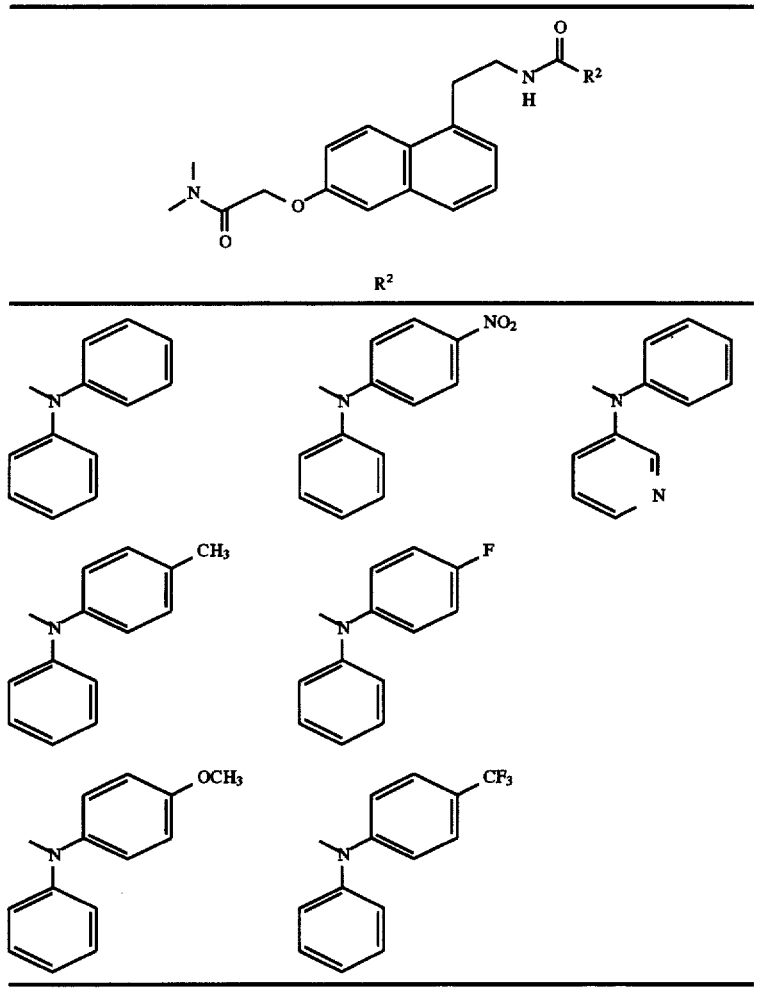
TABLE 15
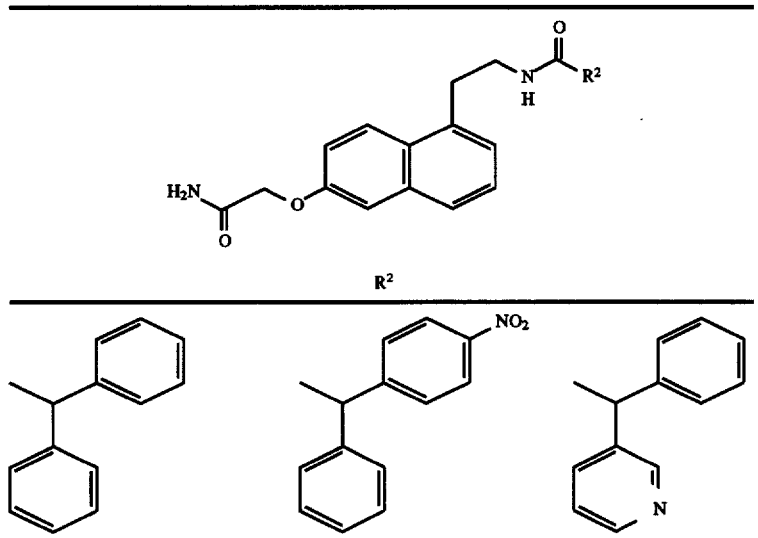

TABLE 15-continued
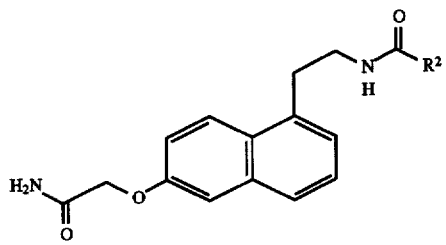
R²
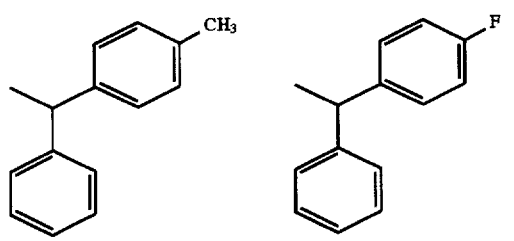
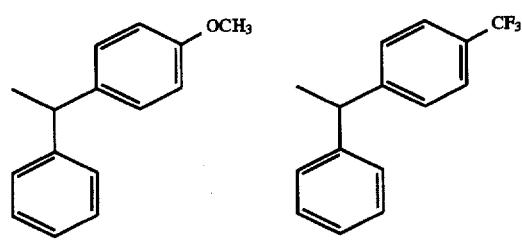
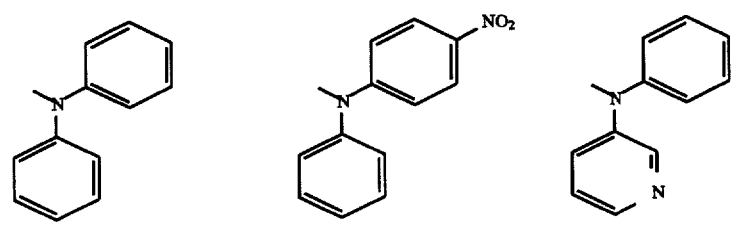
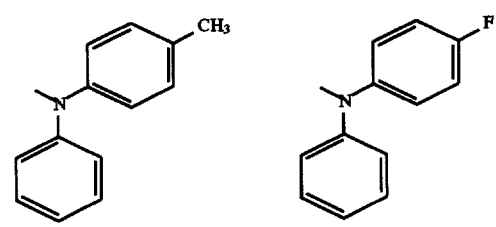
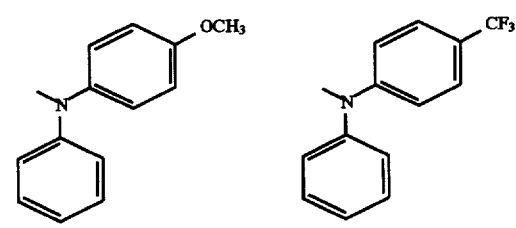

TABLE 16
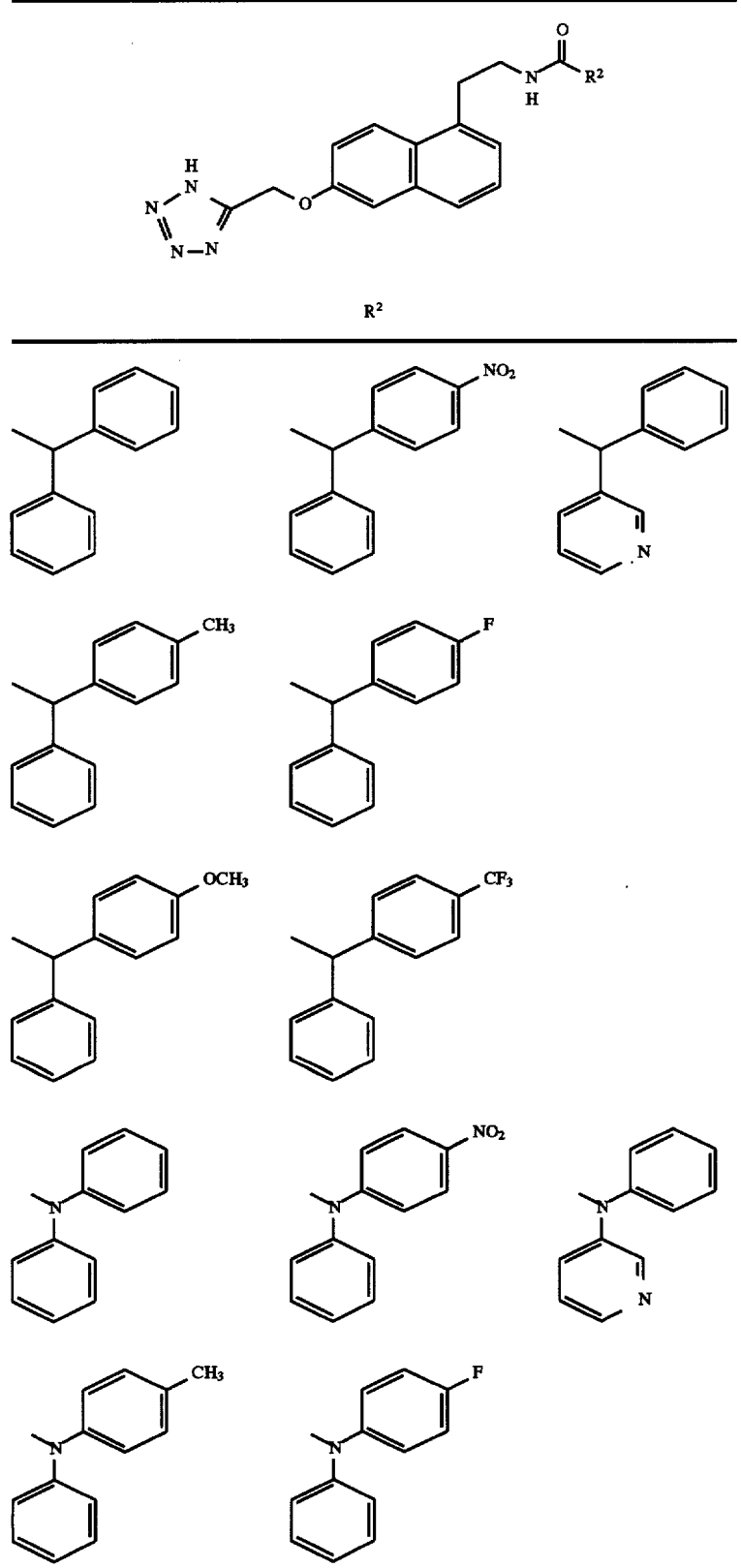

TABLE 16-continued
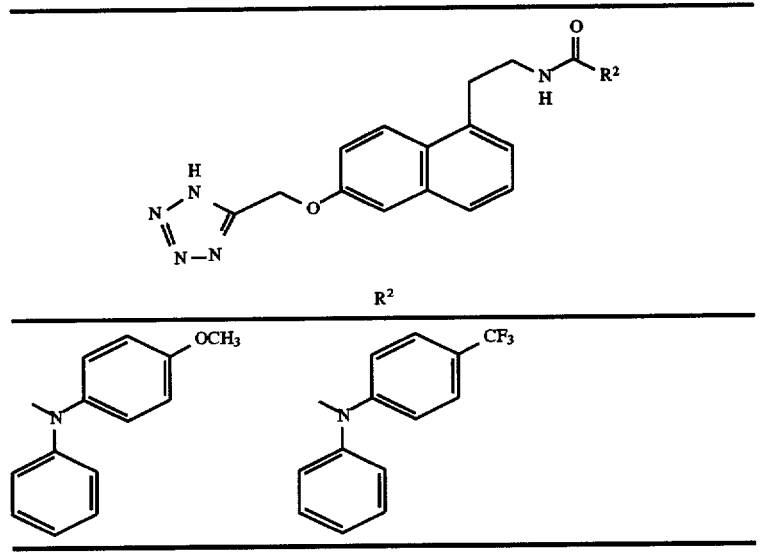
TABLE 17
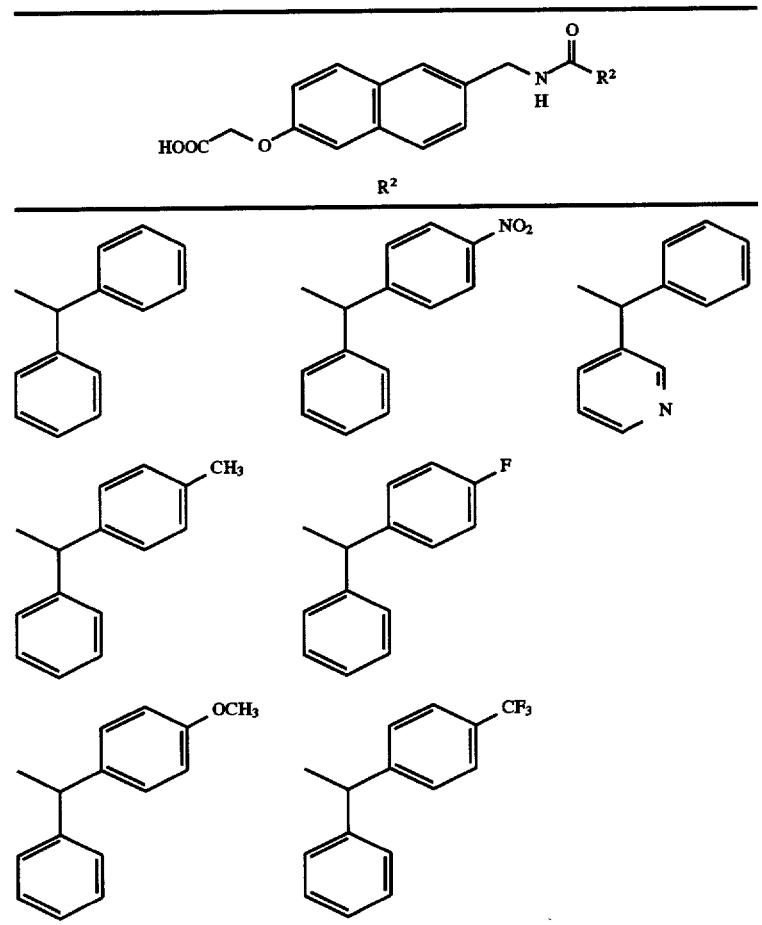

TABLE 17-continued
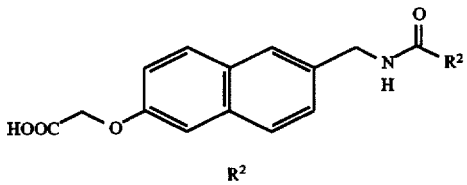
R²
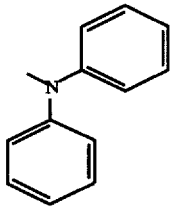 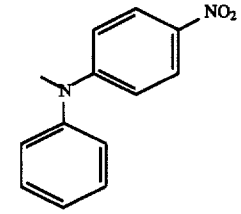 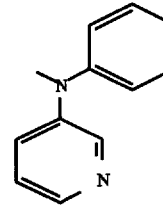
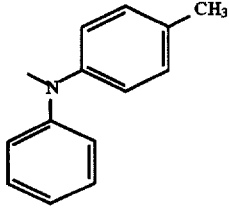 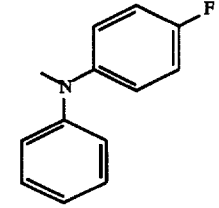
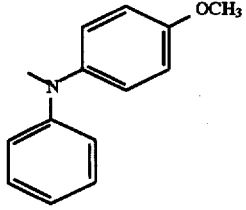 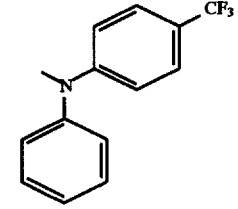
TABLE 18
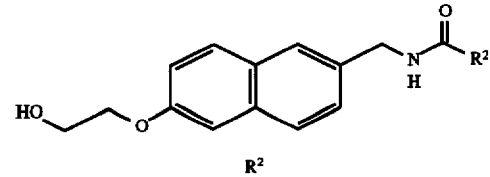
R²
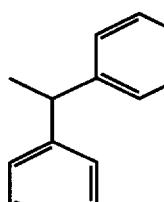 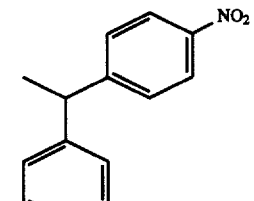 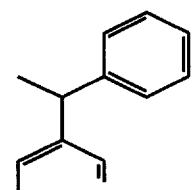
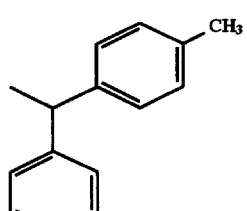 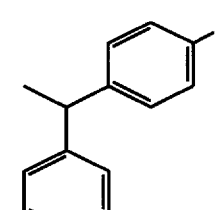

TABLE 18-continued
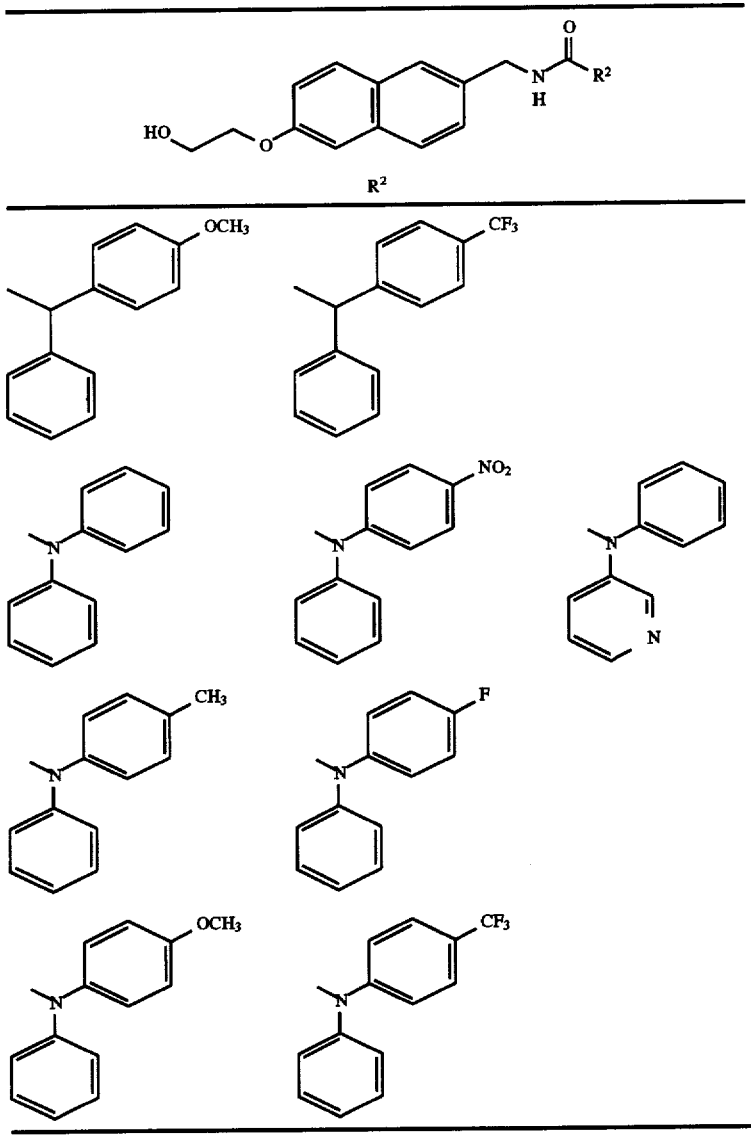
TABLE 19
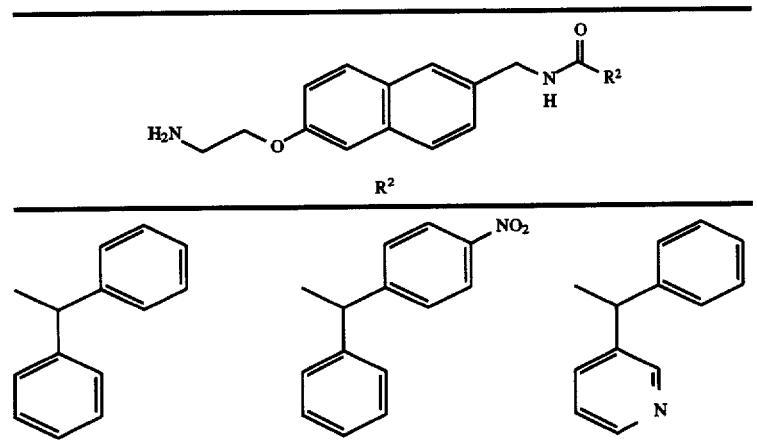

TABLE 19-continued
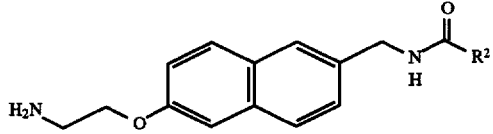

TABLE 20
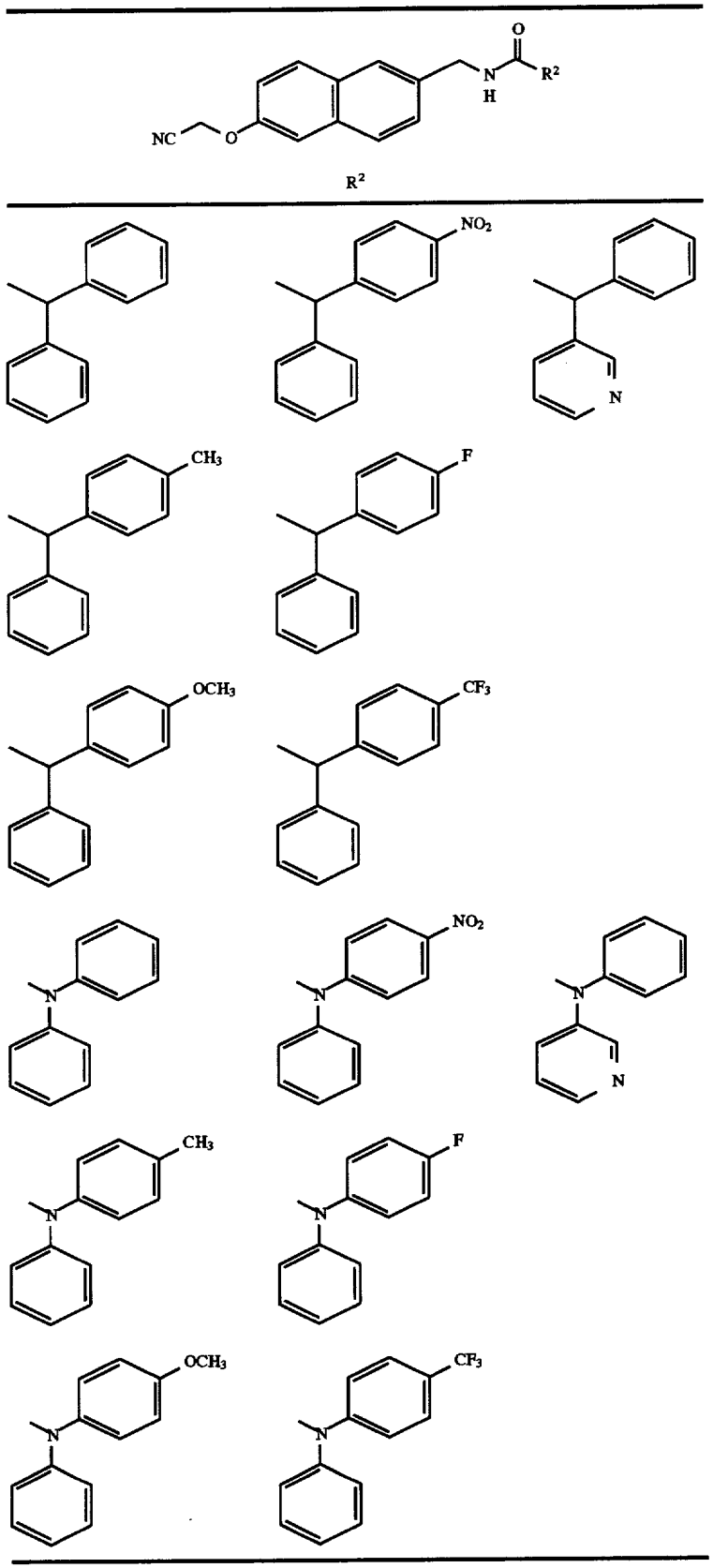

TABLE 21
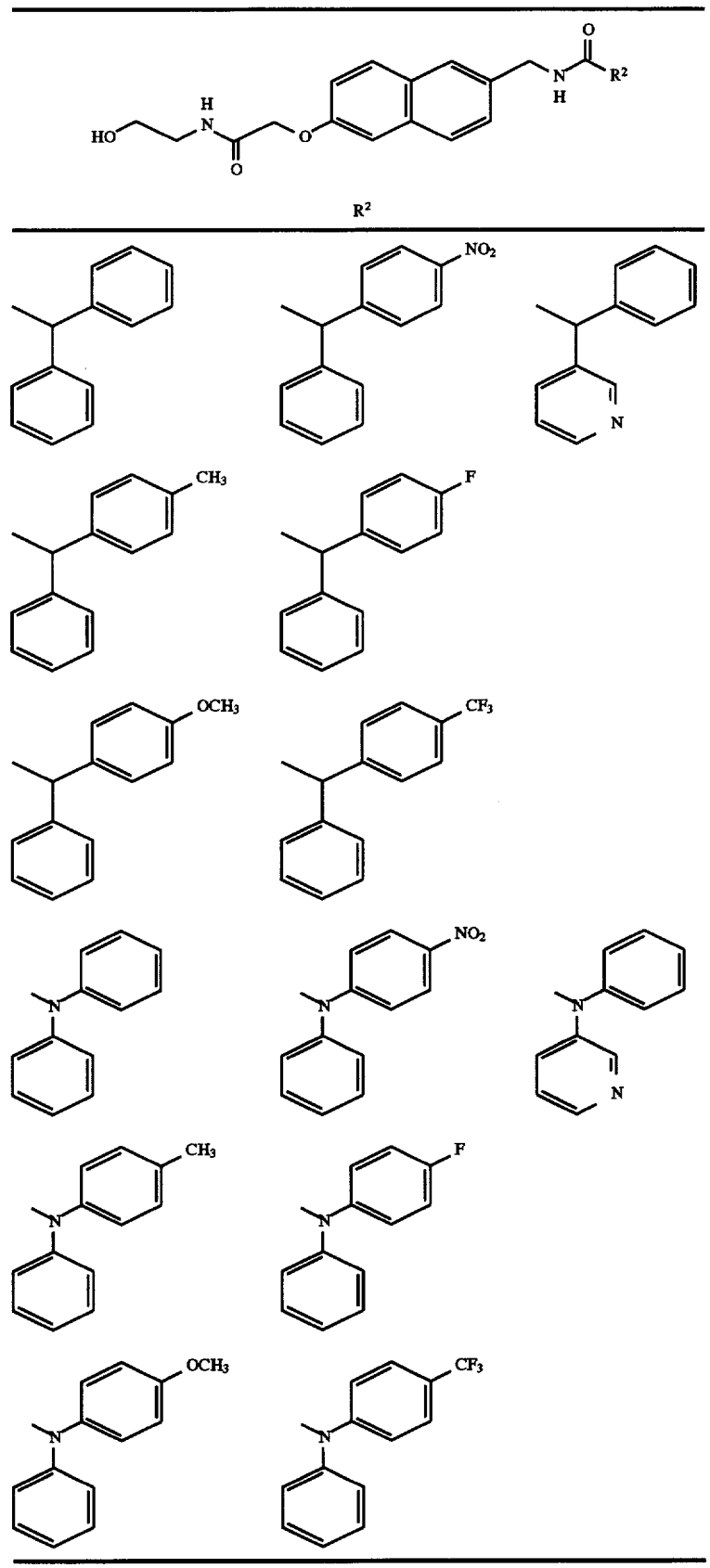

TABLE 22

[Structure: naphthalene core with (CH₃)₂N-C(=O)-CH₂-O- on one side and -CH₂-NH-C(=O)-R² on the other]

R²

(R² groups shown:)
- CH(C₆H₅)₂ (1-phenyl-1-phenylethyl, i.e., diphenylmethyl with methyl)
- CH(CH₃)(4-NO₂-C₆H₄)(C₆H₅)
- CH(CH₃)(3-pyridyl)(C₆H₅)
- CH(CH₃)(4-CH₃-C₆H₄)(C₆H₅)
- CH(CH₃)(4-F-C₆H₄)(C₆H₅)
- CH(CH₃)(4-OCH₃-C₆H₄)(C₆H₅)
- CH(CH₃)(4-CF₃-C₆H₄)(C₆H₅)
- N(CH₃)(C₆H₅) with phenyl
- N(CH₃)(4-NO₂-C₆H₄)(C₆H₅)
- N(CH₃)(3-pyridyl)(C₆H₅)
- N(CH₃)(4-CH₃-C₆H₄)(C₆H₅)
- N(CH₃)(4-F-C₆H₄)(C₆H₅)
- N(CH₃)(4-OCH₃-C₆H₄)(C₆H₅)
- N(CH₃)(4-CF₃-C₆H₄)(C₆H₅)

TABLE 23
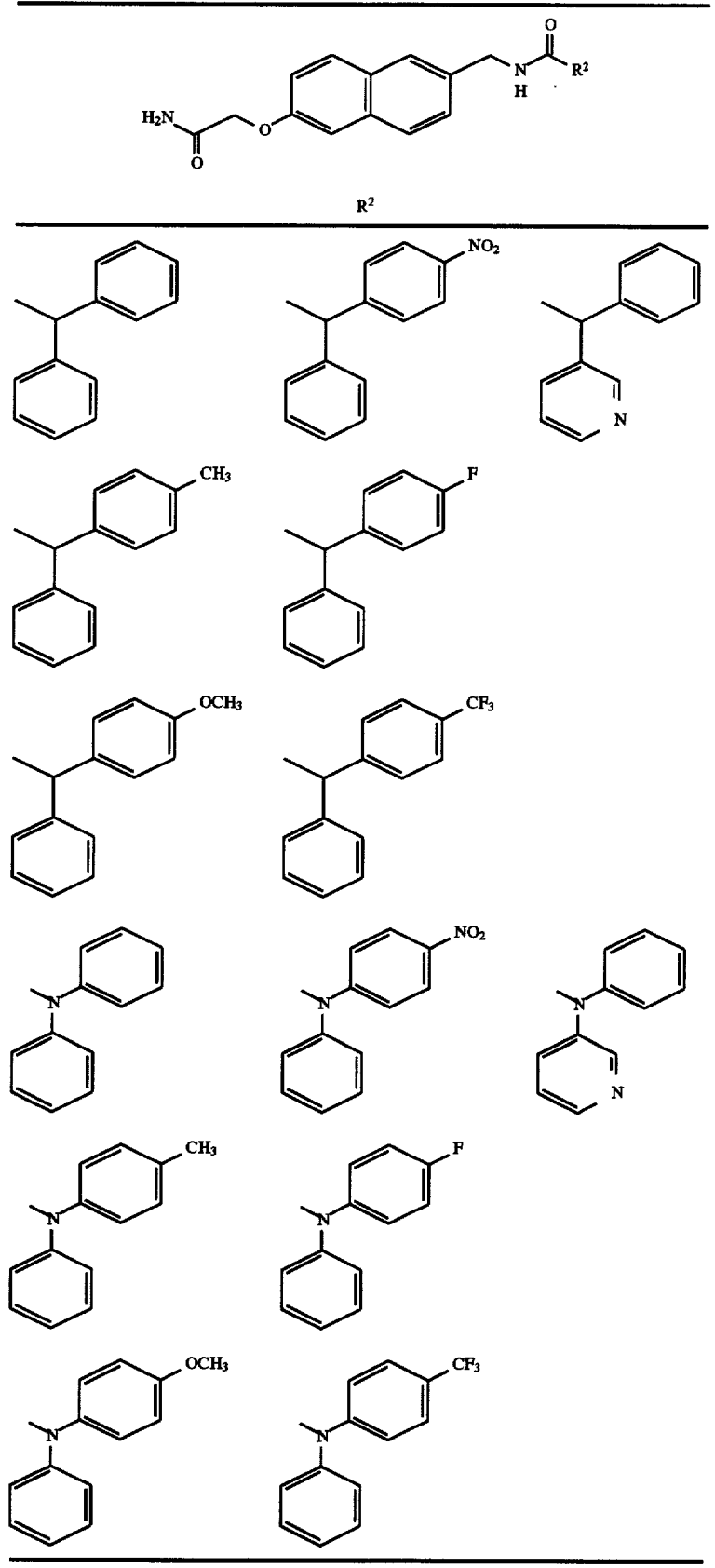

TABLE 24
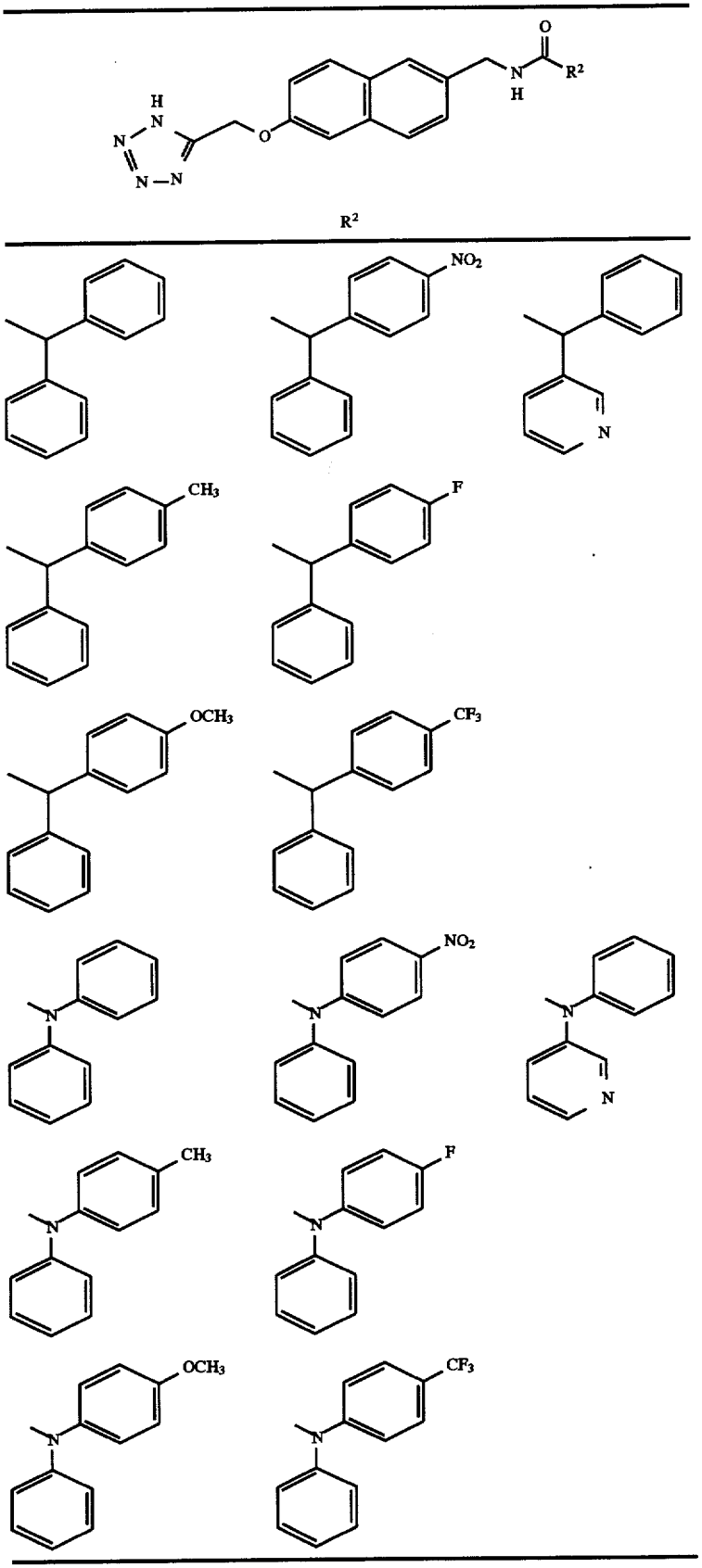

TABLE 25
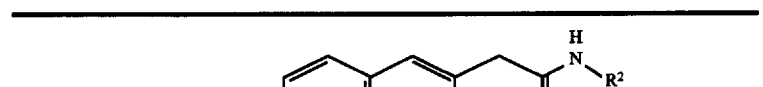

TABLE 26
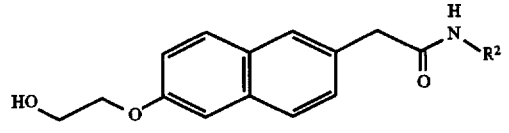

TABLE 27
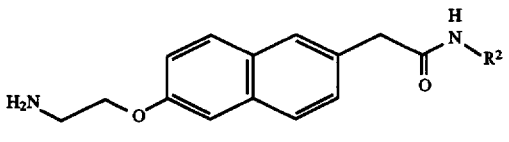

TABLE 28

TABLE 29

Core structure: HO-CH₂CH₂-NH-C(=O)-CH₂-O-[naphthalene-2,6-diyl]-CH₂-C(=O)-NH-R²

R² groups:

- −CH(CH₃)−C₆H₅, with additional phenyl (1-phenylethyl with extra phenyl at α-carbon, i.e., −CH(Ph)(Ph)... actually α-methyl-diphenylmethyl)
- −CH(CH₃)−(4-NO₂-C₆H₄), with additional phenyl
- −CH(CH₃)−(pyridin-3-yl), with additional phenyl
- −CH(CH₃)−(4-CH₃-C₆H₄), with additional phenyl
- −CH(CH₃)−(4-F-C₆H₄), with additional phenyl
- −CH(CH₃)−(4-OCH₃-C₆H₄), with additional phenyl
- −CH(CH₃)−(4-CF₃-C₆H₄), with additional phenyl
- −N(C₆H₅)(C₆H₅) (diphenylamino via N-methyl linkage shown as N-CH₃ with two phenyls) — N,N-diphenyl
- −N(CH₃ linker)−(4-NO₂-C₆H₄), with additional phenyl on N
- −N−(pyridin-3-yl), with additional phenyl on N
- −N−(4-CH₃-C₆H₄), with additional phenyl on N
- −N−(4-F-C₆H₄), with additional phenyl on N
- −N−(4-OCH₃-C₆H₄), with additional phenyl on N
- −N−(4-CF₃-C₆H₄), with additional phenyl on N TABLE 30
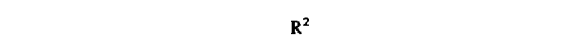
R²
  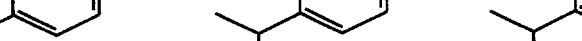
 
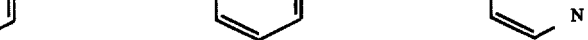 
 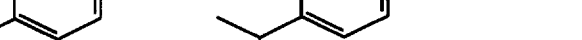 
 
 

TABLE 31
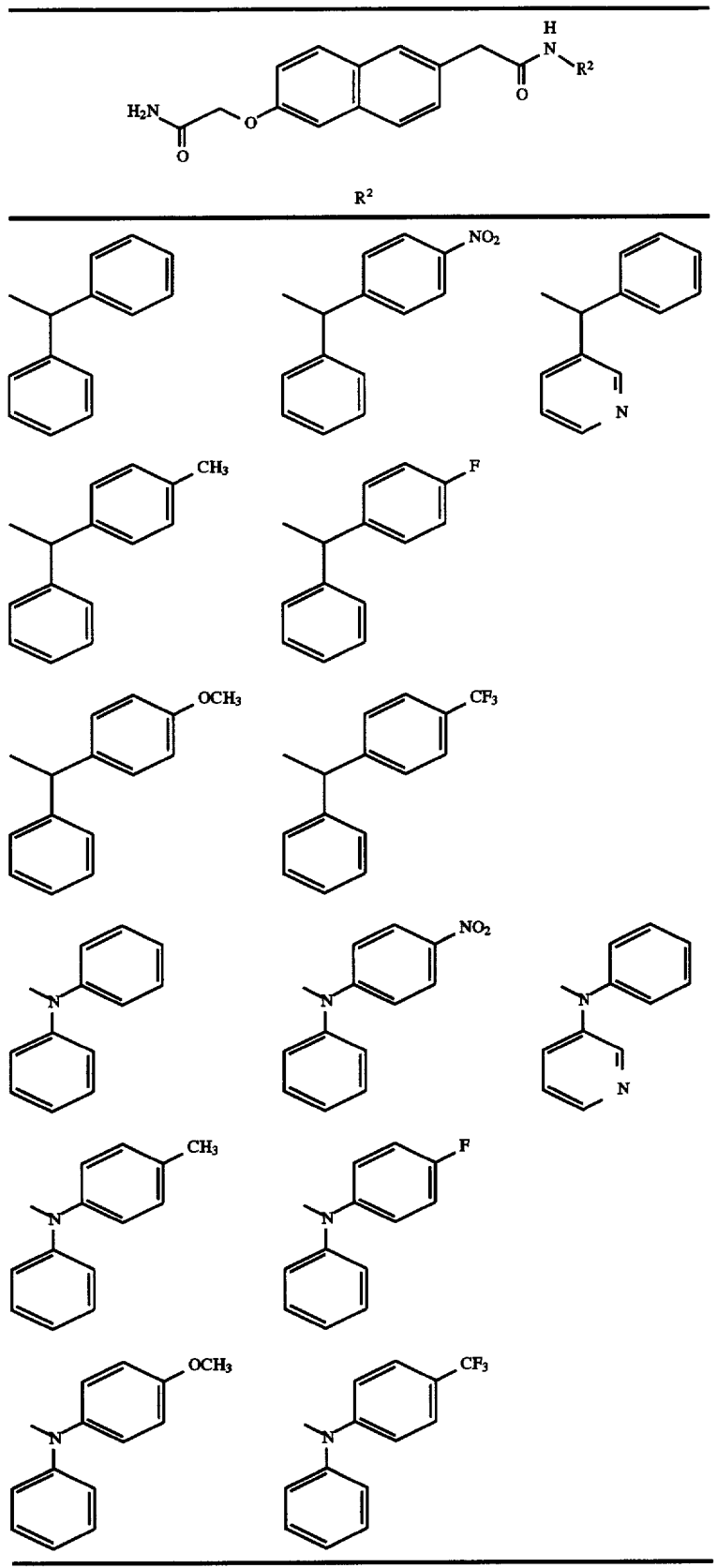

TABLE 32

[Structure: 5-((1H-tetrazol-5-yl)methoxy)naphthalen-2-yl acetamide core with N-H, N-R²]

R²:

- CH(CH₃)(C₆H₅)₂ (1,1-diphenylethyl)
- CH(CH₃)(4-NO₂-C₆H₄)(C₆H₅)
- CH(CH₃)(3-pyridyl)(C₆H₅)
- CH(CH₃)(4-CH₃-C₆H₄)(C₆H₅)
- CH(CH₃)(4-F-C₆H₄)(C₆H₅)
- CH(CH₃)(4-OCH₃-C₆H₄)(C₆H₅)
- CH(CH₃)(4-CF₃-C₆H₄)(C₆H₅)
- N(CH₃)(C₆H₅)(C₆H₅)
- N(CH₃)(4-NO₂-C₆H₄)(C₆H₅)
- N(CH₃)(3-pyridyl)(C₆H₅)
- N(CH₃)(4-CH₃-C₆H₄)(C₆H₅)
- N(CH₃)(4-F-C₆H₄)(C₆H₅)
- N(CH₃)(4-OCH₃-C₆H₄)(C₆H₅)
- N(CH₃)(4-CF₃-C₆H₄)(C₆H₅)

TABLE 33
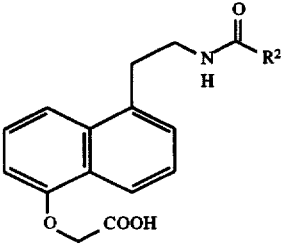

TABLE 33-continued
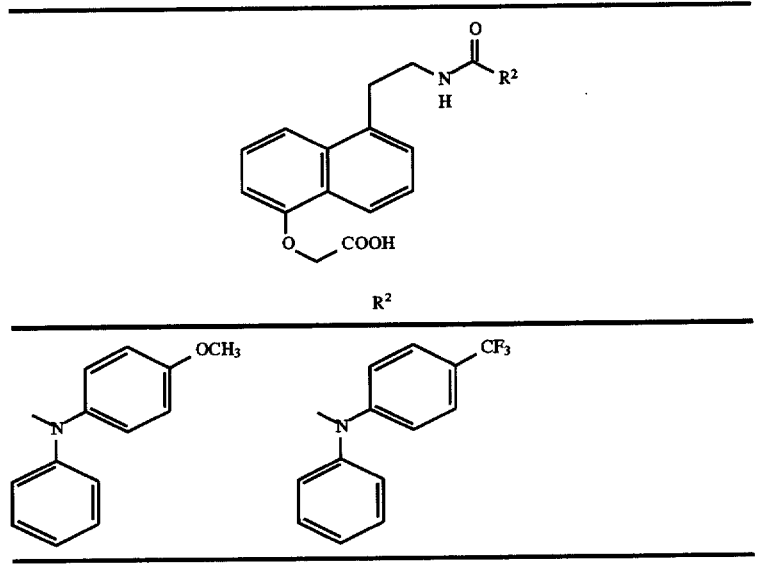
TABLE 34
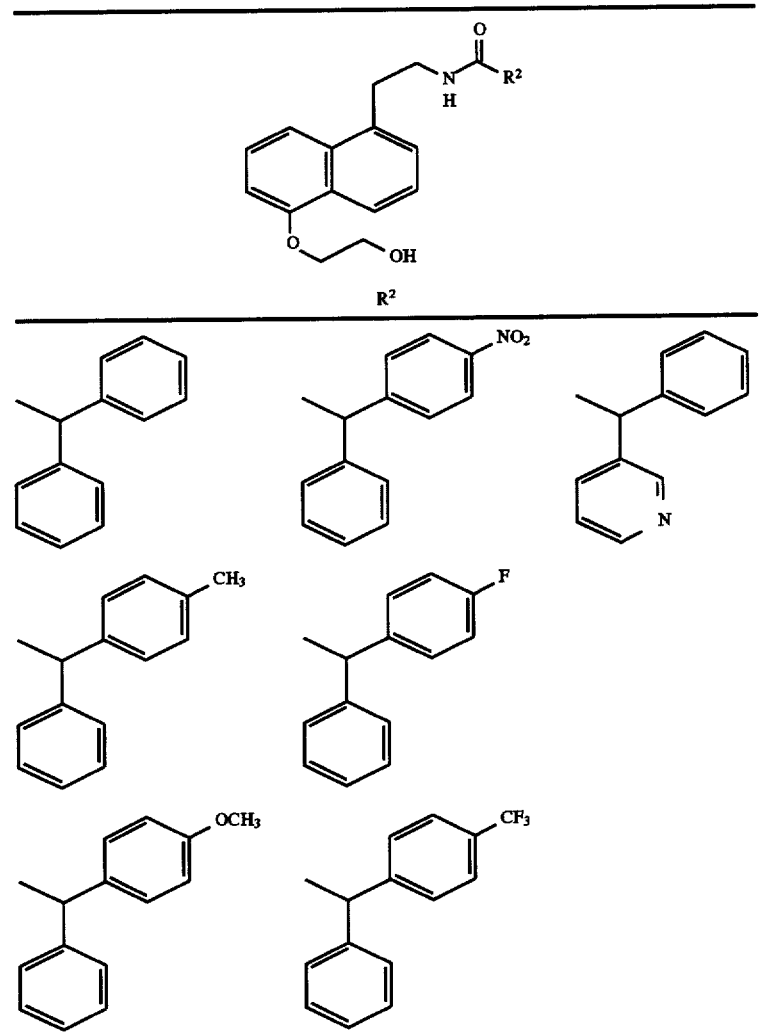

TABLE 34-continued

[Structure: naphthalene with -CH2CH2-NH-C(=O)-R² substituent at position 1 and -O-CH2CH2-OH at position 5]

R²

[Nine R² substituents shown:]
- N-methyl-N-phenylanilino
- N-methyl-N-(4-nitrophenyl)anilino
- N-methyl-N-phenyl-(pyridin-3-yl)amino
- N-methyl-N-(4-methylphenyl)anilino
- N-methyl-N-(4-fluorophenyl)anilino
- N-methyl-N-(4-methoxyphenyl)anilino
- N-methyl-N-(4-trifluoromethylphenyl)anilino

TABLE 35

[Structure: naphthalene with -CH2CH2-NH-C(=O)-R² substituent at position 1 and -O-CH2CH2-NH2 at position 5]

R²

[Three R² substituents shown:]
- 1,1-diphenylethyl
- 1-(4-nitrophenyl)-1-phenylethyl
- 1-phenyl-1-(pyridin-3-yl)ethyl TABLE 35-continued

[Structure: naphthalene with -OCH2CH2NH2 at 5-position and -CH2CH2NHC(O)R² at 1-position]

R²

| | |
|---|---|
| -CH(CH3)-C6H4-CH3 (with phenyl) | -CH(CH3)-C6H4-F (with phenyl) |
| -CH(CH3)-C6H4-OCH3 (with phenyl) | -CH(CH3)-C6H4-CF3 (with phenyl) |
| -N(C6H5)2 with methyl | -N(CH3)(C6H4-NO2)(C6H5) | -N(CH3)(3-pyridyl)(C6H5) |
| -N(CH3)(C6H4-CH3)(C6H5) | -N(CH3)(C6H4-F)(C6H5) |
| -N(CH3)(C6H4-OCH3)(C6H5) | -N(CH3)(C6H4-CF3)(C6H5) |

TABLE 36
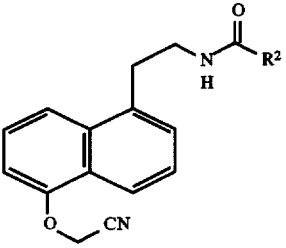
R²
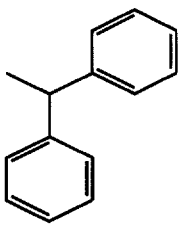 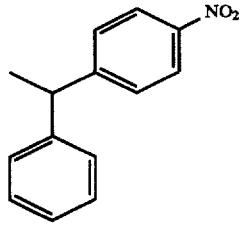 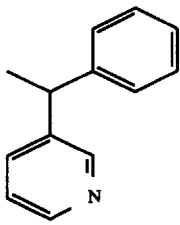
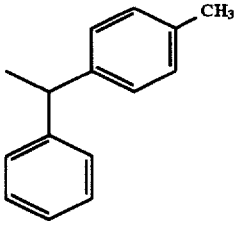 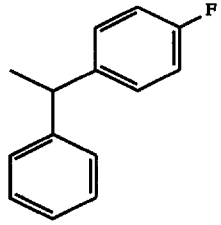
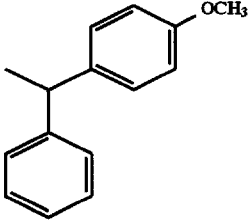 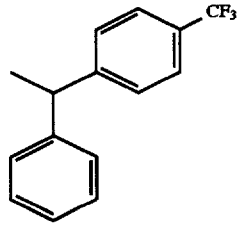
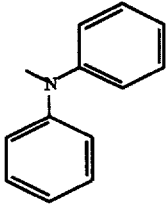 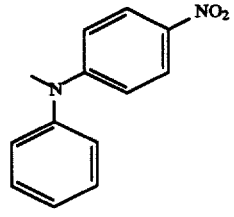 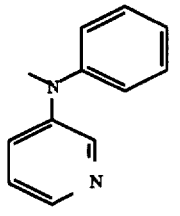
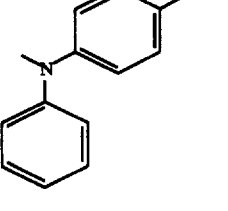 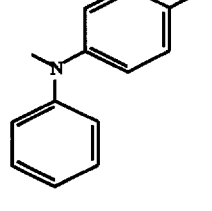

TABLE 36-continued

[Structure: naphthalene with 1-position CH₂CH₂NHC(=O)R² and 5-position OCH₂CN]

R²

[Two R² groups shown:]
- N(phenyl)(CH₂—)—C₆H₄—OCH₃ (para)
- N(phenyl)(CH₂—)—C₆H₄—CF₃ (para)

TABLE 37

[Structure: naphthalene with 1-position CH₂CH₂NHC(=O)R² and 5-position OCH₂C(=O)NH-CH₂CH₂-OH]

R²

[R² groups shown:]
- CH(C₆H₅)₂ attached via CH(CH₃)
- CH(C₆H₅)(4-NO₂-C₆H₄) via CH(CH₃)
- CH(C₆H₅)(3-pyridyl) via CH(CH₃)
- CH(C₆H₅)(4-CH₃-C₆H₄) via CH(CH₃)
- CH(C₆H₅)(4-F-C₆H₄) via CH(CH₃)

TABLE 37-continued

TABLE 38

[Structure: naphthalene with 2-(acylamino)ethyl group at one position and OCH₂C(O)N(CH₃)₂ at another; acyl group = C(O)R²]

R²

[Various R² substituents shown as structures]

TABLE 38-continued
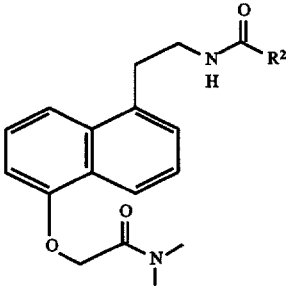
| R² | |
|---|---|
| 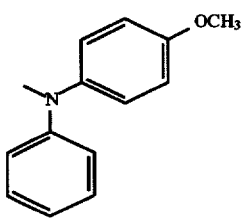 | 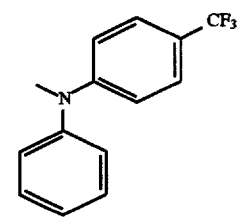 |
TABLE 39
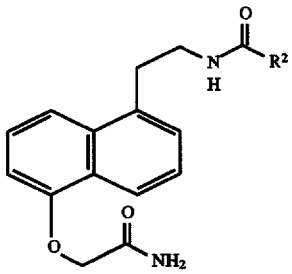
| R² | | |
|---|---|---|
| 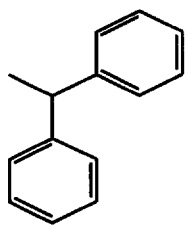 | 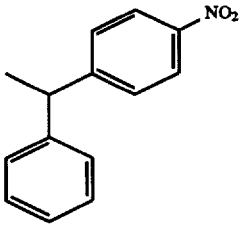 | 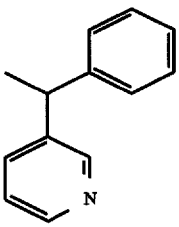 |
| 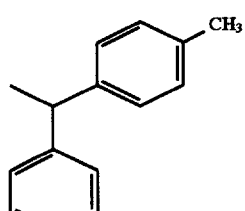 | 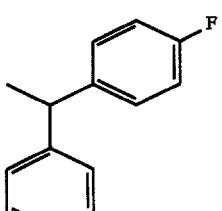 | |

TABLE 39-continued

| Structure |
|---|
| ![main scaffold: naphthalene with -CH2CH2-NH-C(=O)-R2 and -O-CH2-C(=O)-NH2] |

R²

| R² groups |
|---|
| -CH(CH₃)(4-OCH₃-C₆H₄)(C₆H₅) ; -CH(CH₃)(4-CF₃-C₆H₄)(C₆H₅) |
| -N(CH₃)(C₆H₅)₂ ; -N(CH₃)(4-NO₂-C₆H₄)(C₆H₅) ; -N(CH₃)(3-pyridyl)(C₆H₅) |
| -N(CH₃)(4-CH₃-C₆H₄)(C₆H₅) ; -N(CH₃)(4-F-C₆H₄)(C₆H₅) |
| -N(CH₃)(4-OCH₃-C₆H₄)(C₆H₅) ; -N(CH₃)(4-CF₃-C₆H₄)(C₆H₅) |

TABLE 40
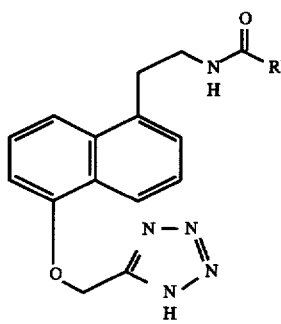
R²
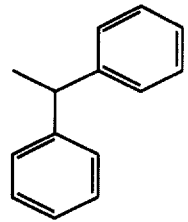 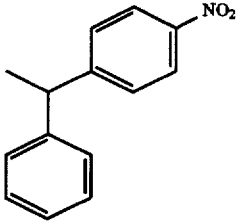 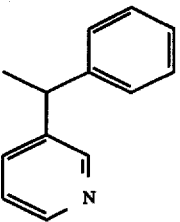
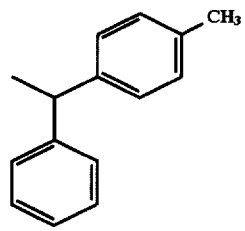 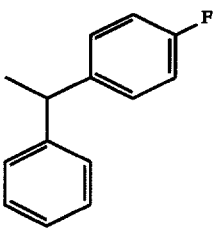
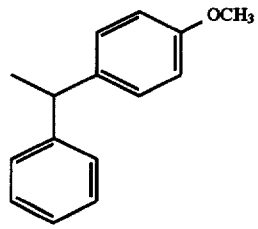 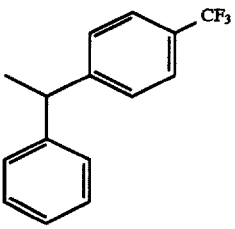
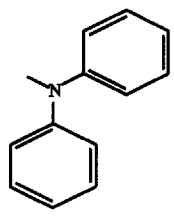 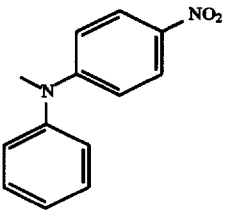 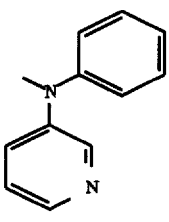
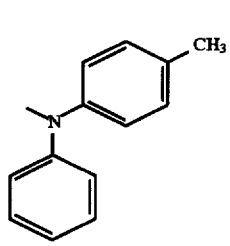 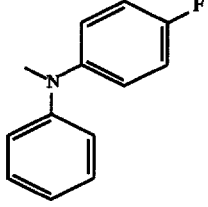

TABLE 40-continued
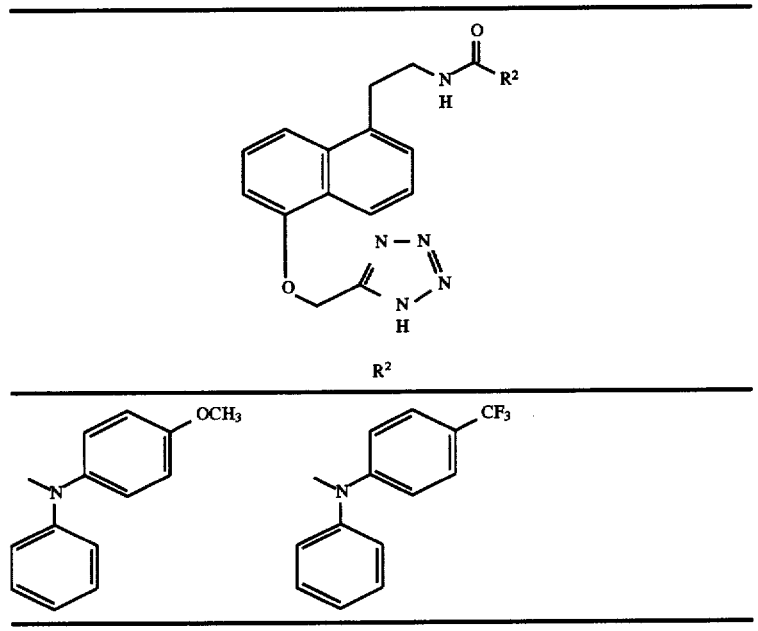
TABLE 41
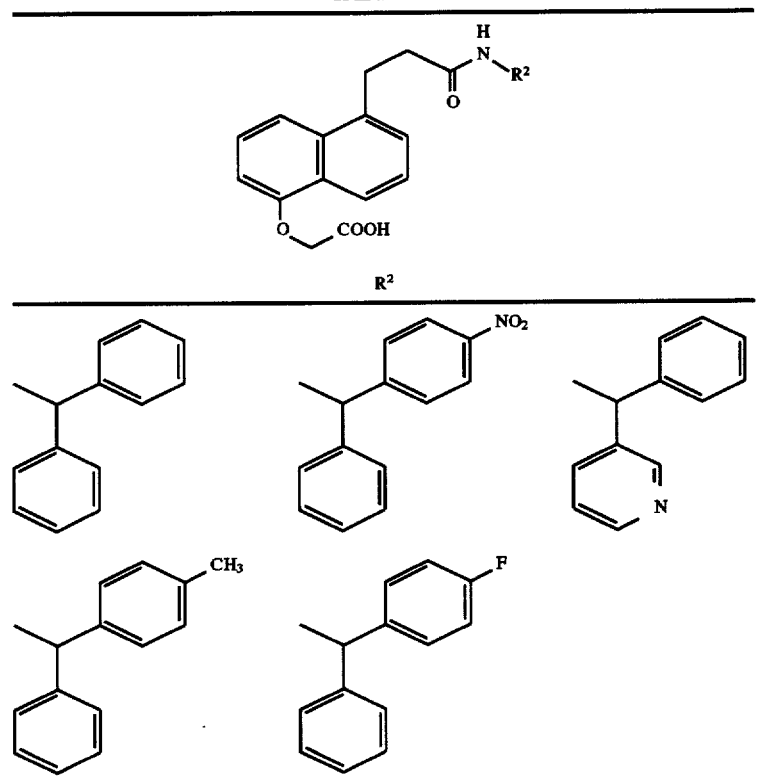

TABLE 41-continued
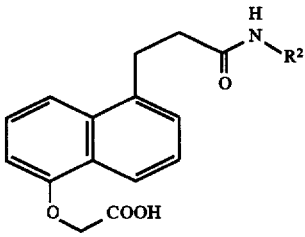
R²
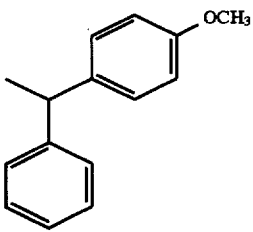

TABLE 42
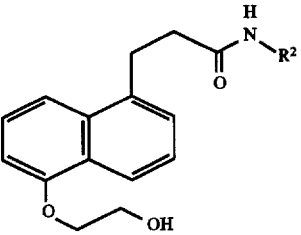
R²
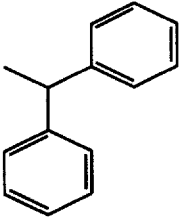 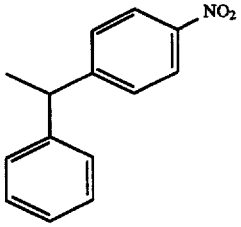 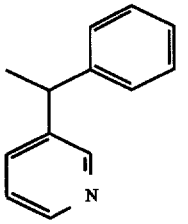
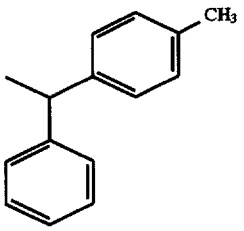 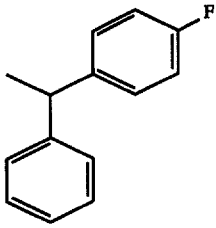
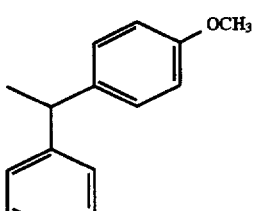 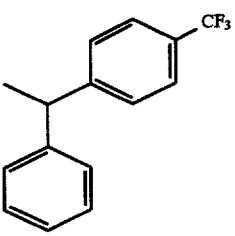
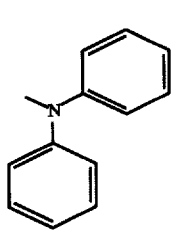 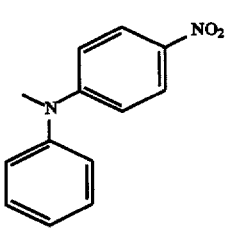 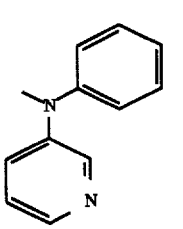
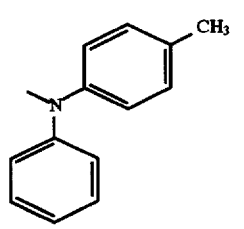 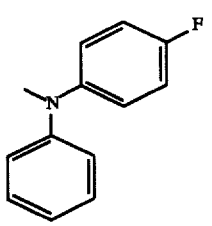

TABLE 42-continued
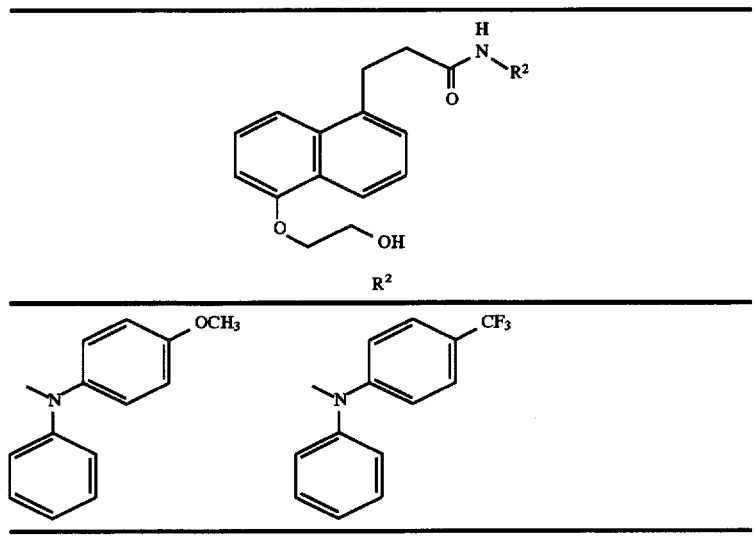
TABLE 43
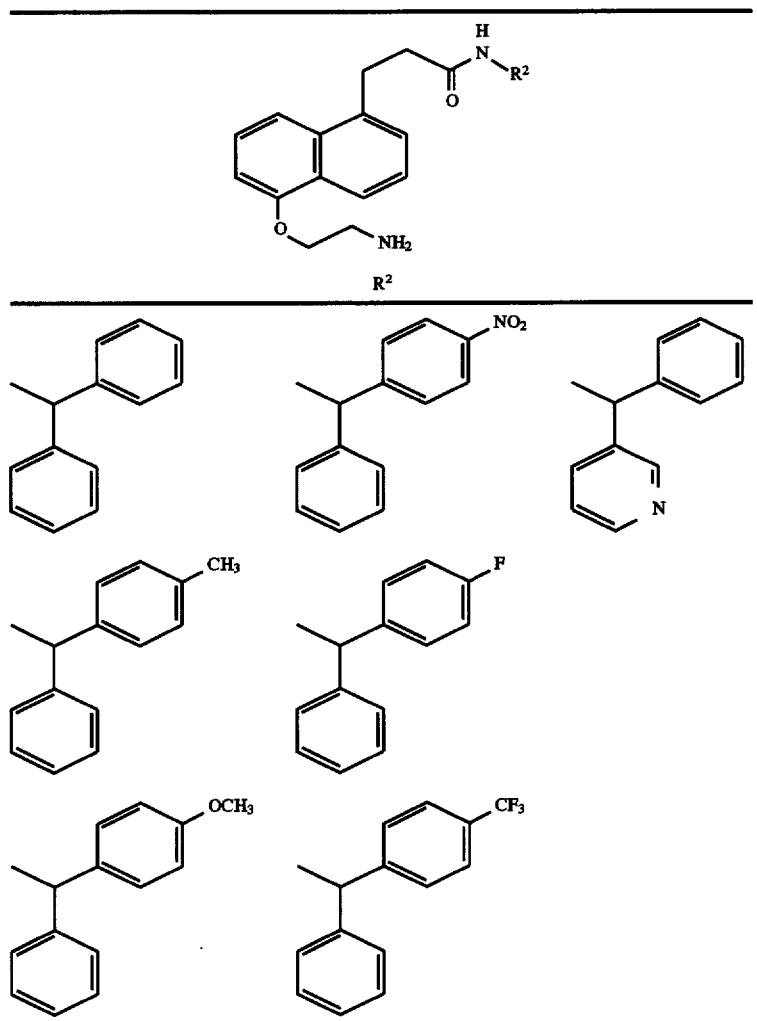

TABLE 43-continued
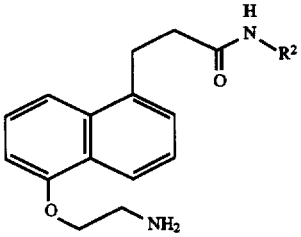
| R² |
|---|
| 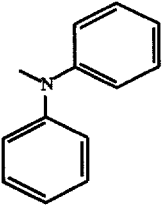 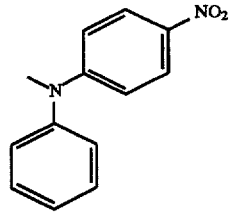 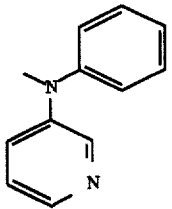 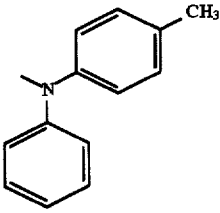 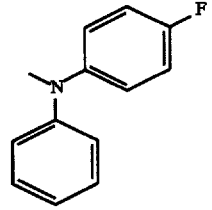 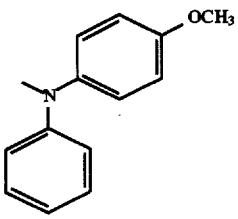 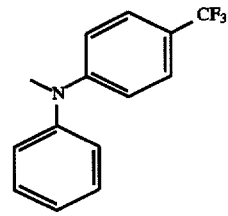 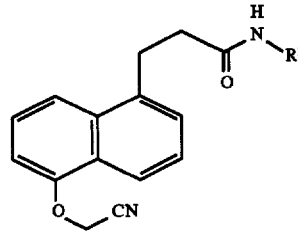 |
TABLE 44
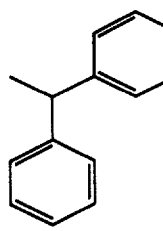
| R² |
|---|
| 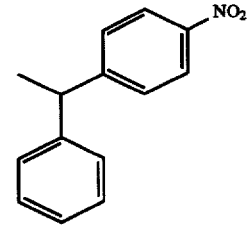 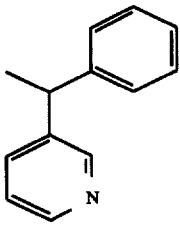 |

TABLE 44-continued
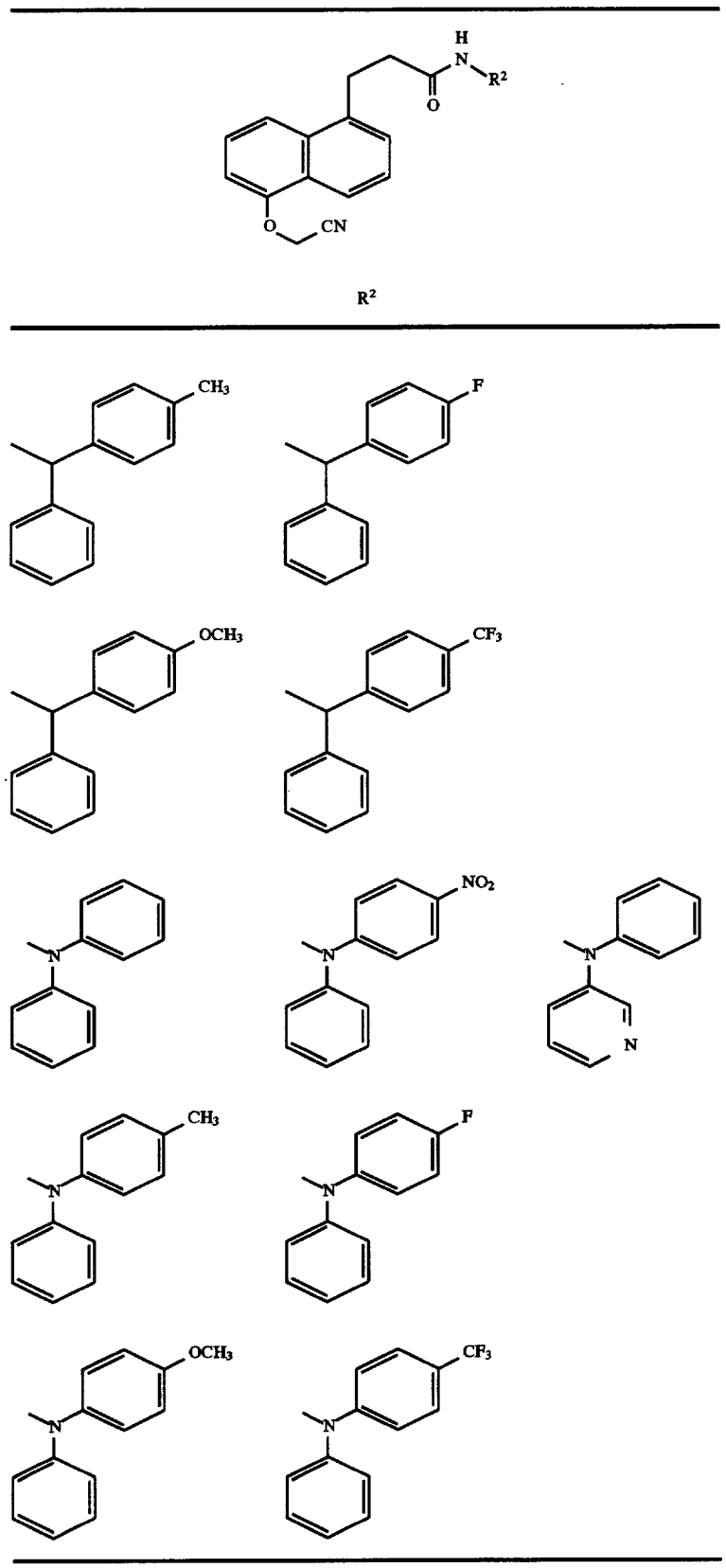
R²

TABLE 45
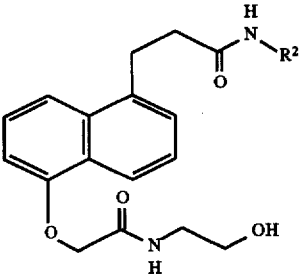
R²
| 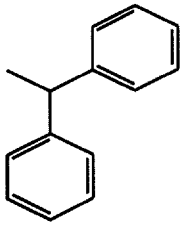 | 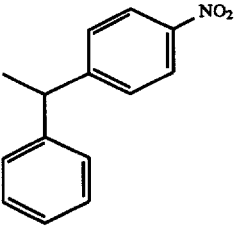 | 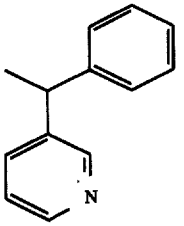 |
| 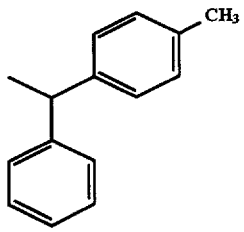 | 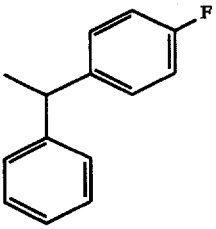 | |
| 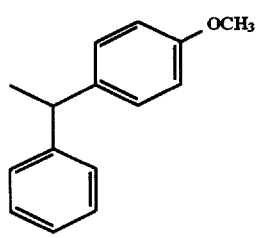 | 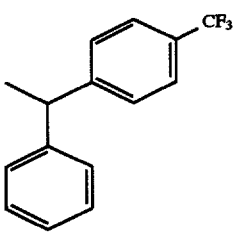 | |
| 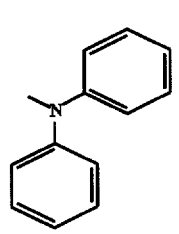 | 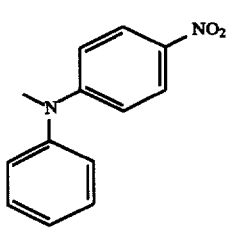 | 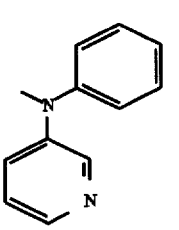 |
| 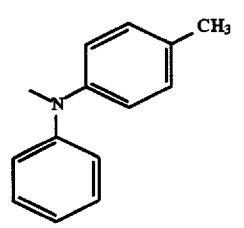 | 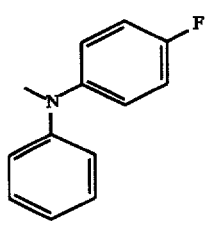 | |

TABLE 45-continued
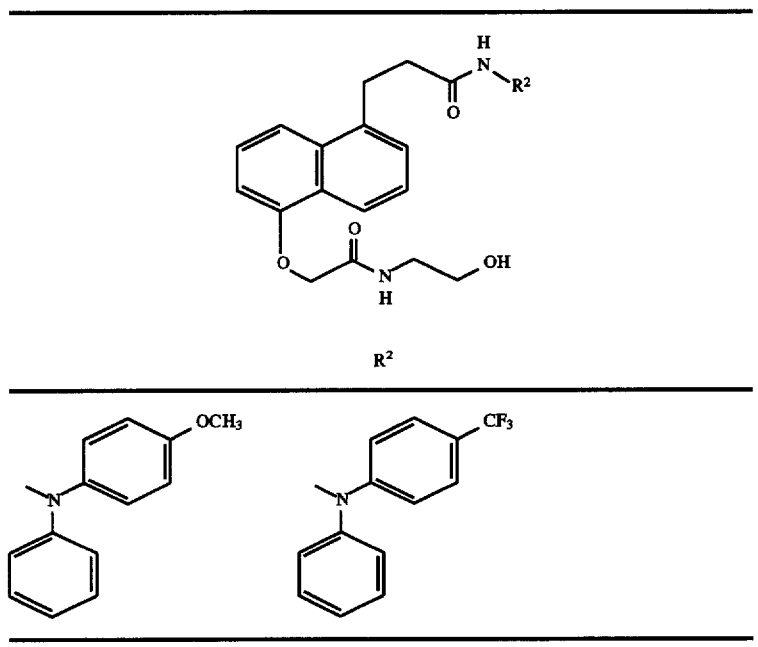
TABLE 46
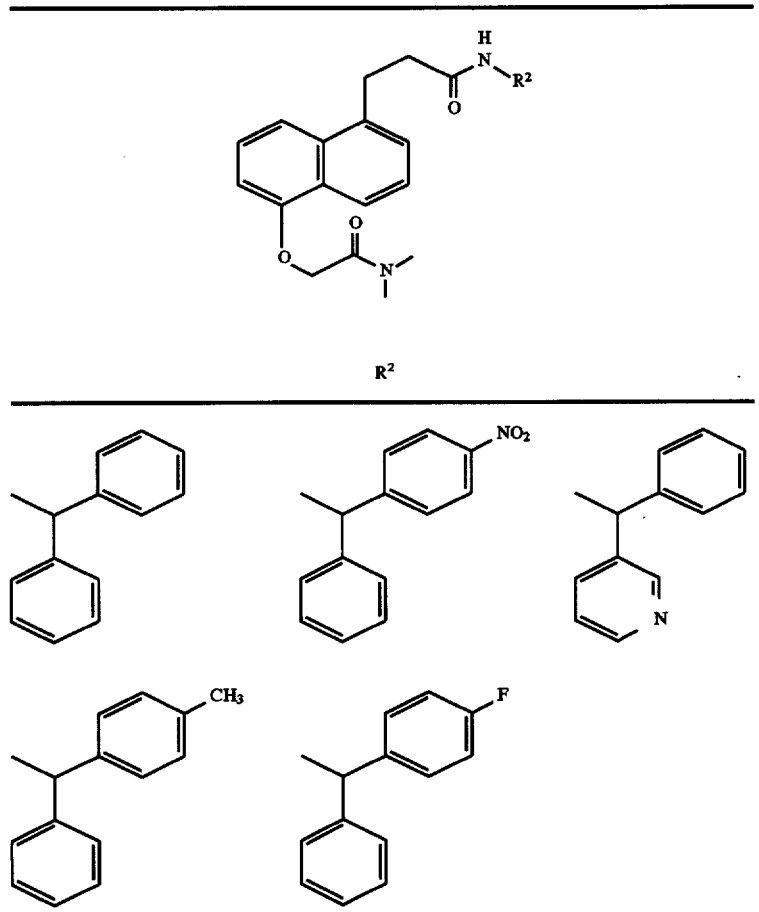

TABLE 46-continued
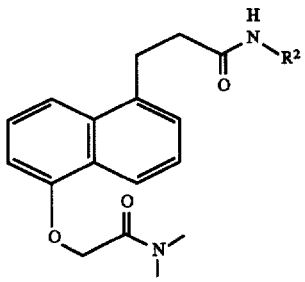
R²
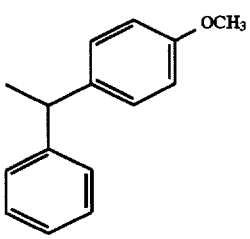
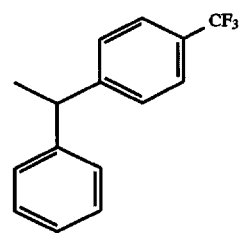
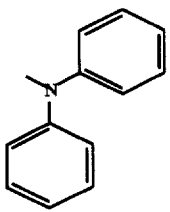
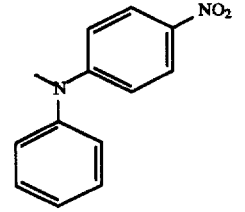
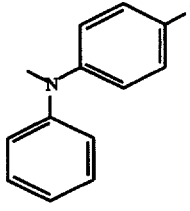
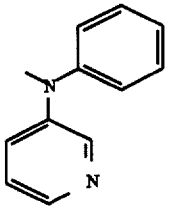
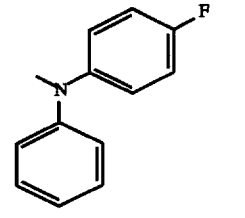
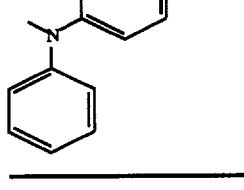
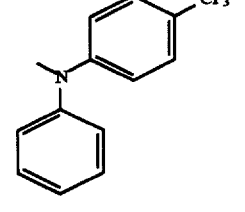

TABLE 47
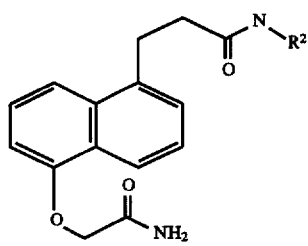
R²
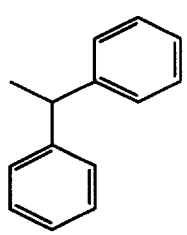 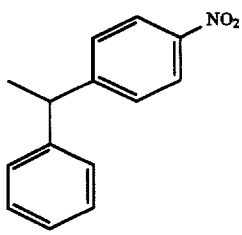 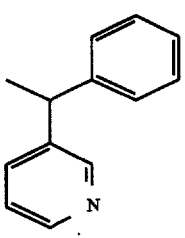
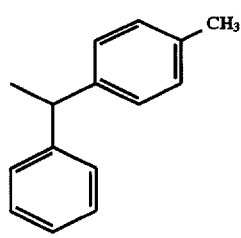 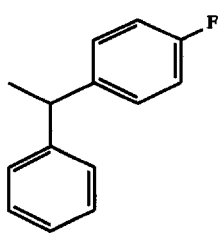
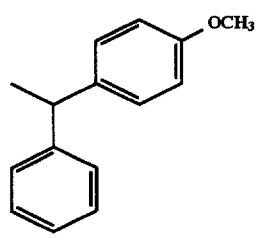 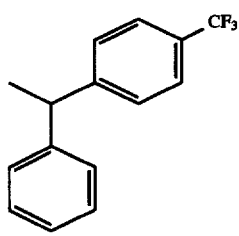
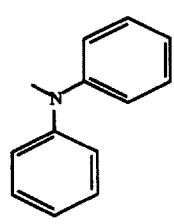 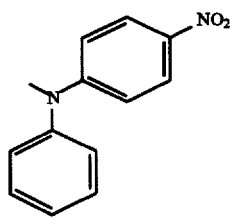 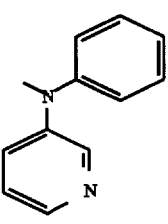
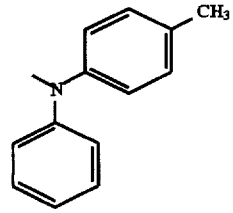 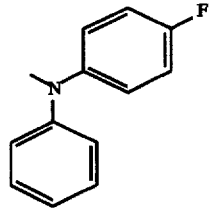

TABLE 47-continued
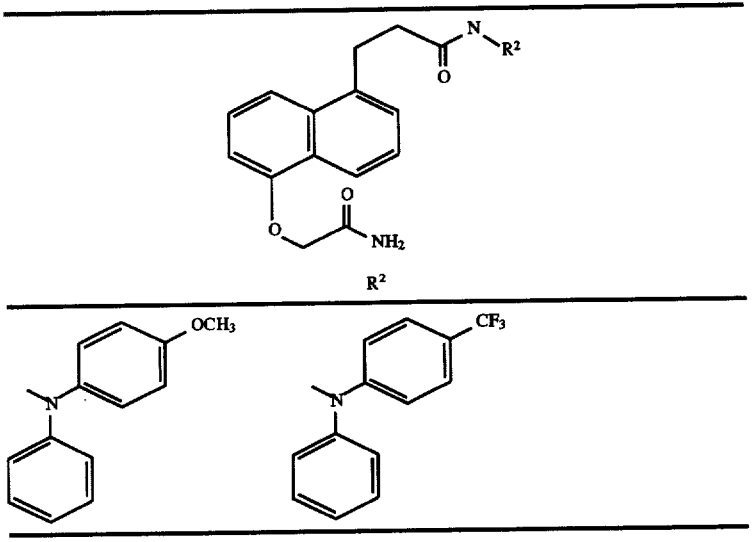
TABLE 48
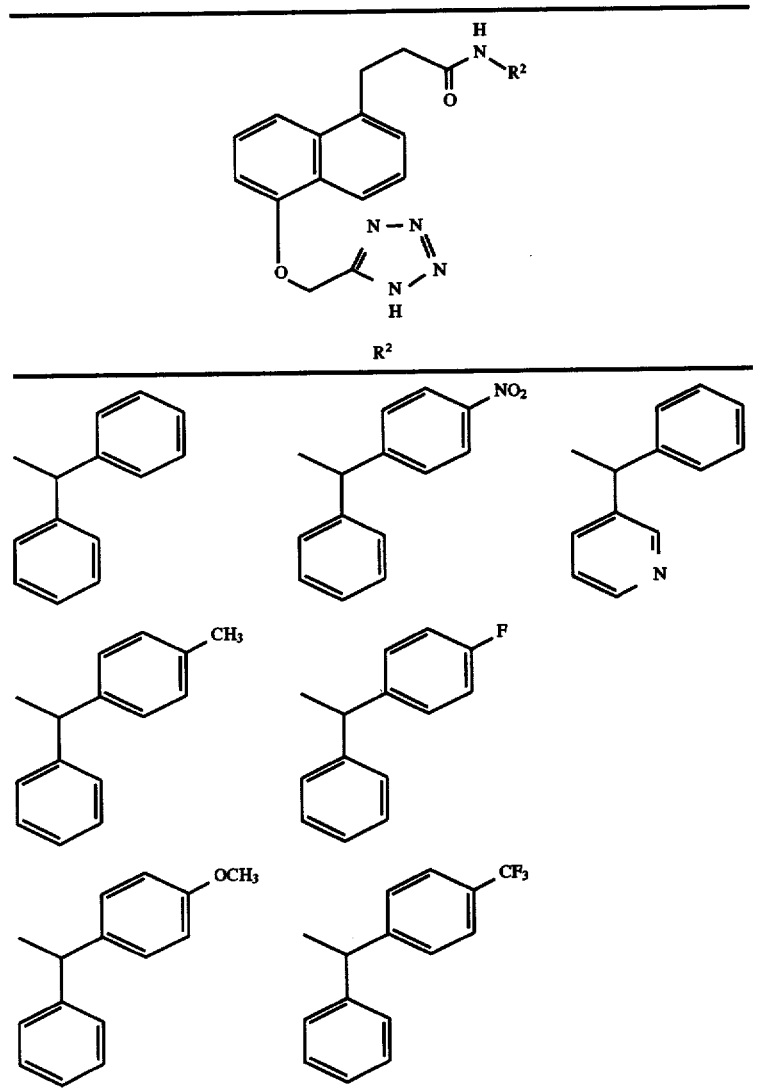

TABLE 48-continued
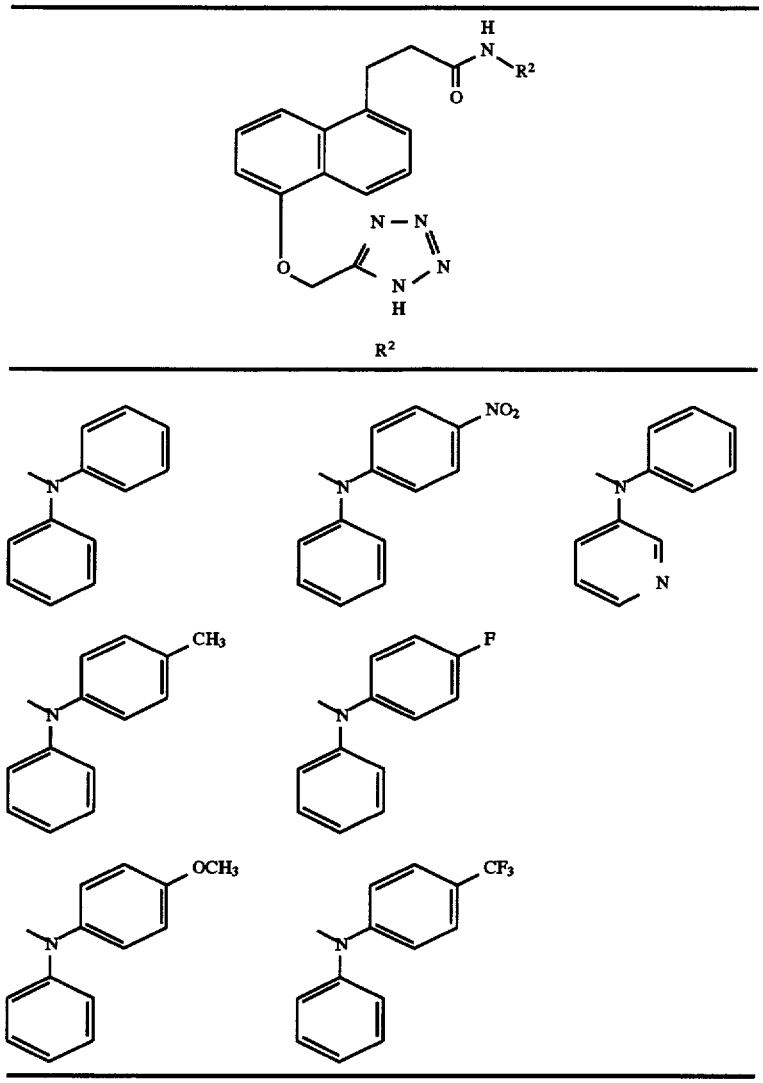
TABLE 49
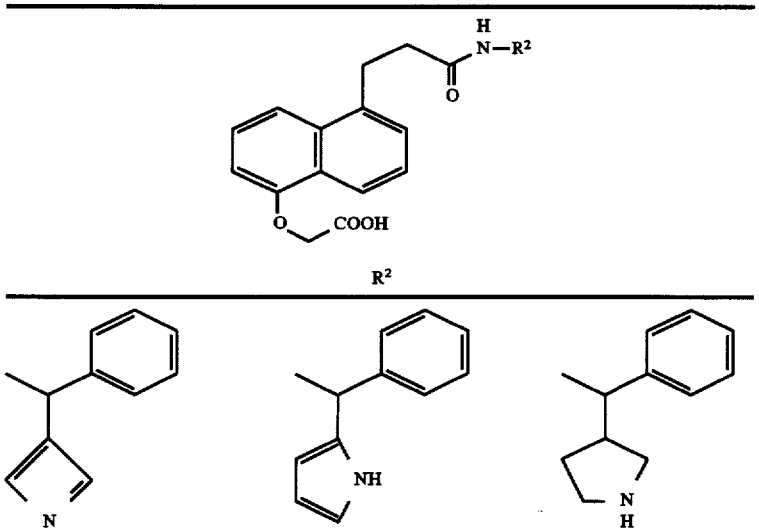

TABLE 49-continued

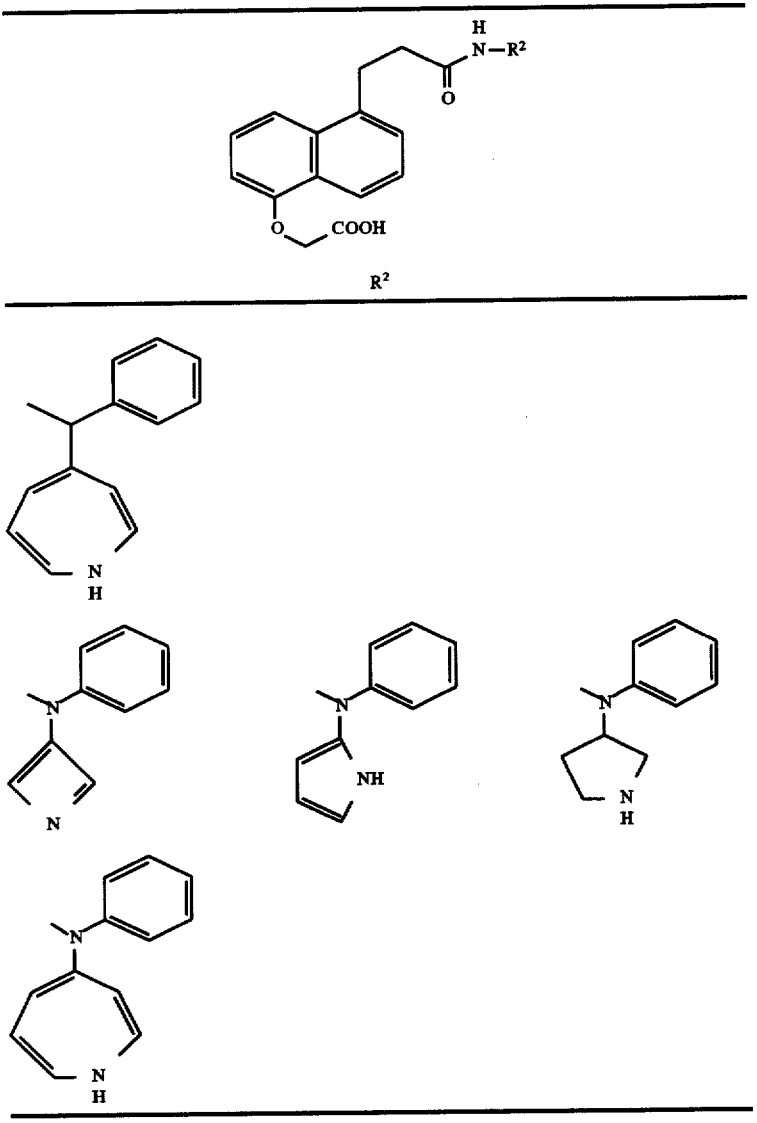

Method of preparation for the compounds of the present invention

The compounds of the formula (I), wherein $R^1$ is C1–4 alkyl or (C1–4 alkylene)-COOR$^{10}$ in which $R^{10}$ is the same meaning as herein before defined, B is NR$^3$CO in which $R^3$ is the same meaning as hereinbefore defined, i.e. the compounds of the formula (Ia)

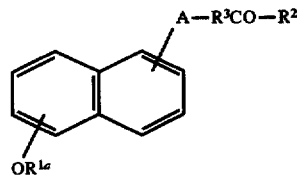
(Ia)

wherein $R^{1a}$ is C1–4 alkyl or (C1–4 alkylene)-COOR$^{10}$ in which $R^{10}$ is the same meaning as hereinbefore defined and the other symbols are the same meaning as hereinbefore defined may be prepared by reacting the compounds of the formula (II)

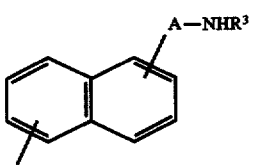
(II)

wherein $R^{1aa}$ is C1–4 alkyl or (C1–4 alkylene)-COOR$^{10a}$ in which $R^{10a}$ is C1–4 alkyl, and the other symbols are the same meaning as hereinbefore defined with the compounds of the formula (III)

HOOC—R$^2$ (III)

wherein $R^2$ is the same meaning as hereinbefore defined to form an amide-bond, if necessary, followed by hydrolysis in an alkaline condition.

Reactions to form amide-bond are well known, it may be carried out, for example;

(1) by the method with using acid halide
(2) by the method with using mixed acid anhydride
(3) by the method with using condensing agent (1-(3-dimethylaminopropyl)-3-ethyl carbodiimide (EDC), dicyclohexylcarbodiimide (DCC) etc.).

Concrete description of the methods described above are as follows:

(1) method with using acid halide may be carried out, for example; carboxylic acid is reacted with an acid halide (oxalyl chloride or thionyl chloride etc.) in an inert organic solvent (chloroform, methylene chloride, diethylether or tetrahydrofuran (THF) etc.) or without solvents at from −20° C. to a refluxing temperature of the solvent used to give an acid halide. The obtained acid halide and an amine are reacted in an inert organic solvent (chloroform, methylene chloride, diethylether, THF etc.) in the presence of tertiary amine (pyridine, triethylamine, dimethylaniline or dimethylaminopyridine etc.) at 0°–40° C.

(2) method with using mixed acid anhydride may be carried out, for example; carboxylic acid is reacted with an acid halide (pivaloyl chloride, tosyl chloride, mesyl chloride etc.) or an acid derivative (ethyl chloroformate, isobutyl chloroformate etc.) in an inert organic solvent (chloroform, methylene chloride, diethyl ether, THF etc.) or without solvents, in the presence of tertiary amine (pyridine, triethylamine, dimethylaniline or dimethylaminopyridine etc.), at 0°–40° C.

(3) method with using condensing agent such as EDC or DCC etc. may be carried out, for example; a carboxylic acid and an amine are reacted in an inert organic solvent (chloroform, methylene chloride, diethylether or THF etc.) or without solvents in the presence or absence of tertiary amine (pyridine, triethylamine, dimethylaniline or dimethylaminopyridine etc.) using with EDC or DCC etc. at 0°–40° C.

Preferably, the reactions (1), (2) and (3) described above are carried out under an atmosphere of inert gas (argon, nitrogen, etc.) under anhydrous condition.

The hydrolysis in an alkaline condition is known. For example, hydrolysis may be carried out in a water-miscible organic solvent (methanol, ethanol dimethoxyethane or mixture thereof etc.), using an alkali (sodium hydroxide, potassium hydroxide etc.), at 0°–50° C.

The compounds of the formula (I), wherein $R^1$ is C1–4 alkyl or (C1–4 alkylene)-COOR$^{10}$ in which $R^{10}$ is the same meaning as hereinbefore defined, B is CONR$^3$ in which $R^3$ is the same meaning as hereinbefore defined, i.e. the compounds of the formula (Ib)

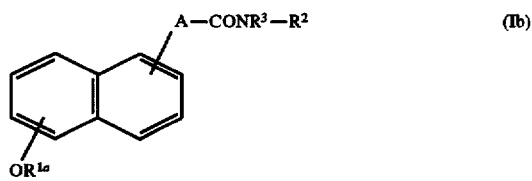

wherein all symbols are the same meaning as hereinbefore defined may be prepared by reacting the compounds of the formula (IV)

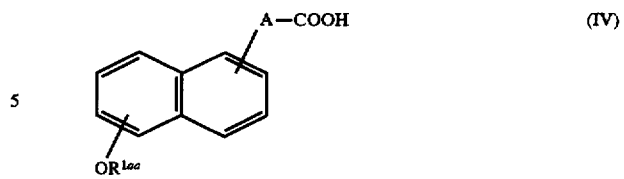

wherein all symbols are the same meaning as hereinbefore defined with the compounds of the formula (V)

$$R^3HN—R^2 \quad (V)$$

wherein all symbols are the same meaning as hereinbefore defined to form an amide-bond, if necessary, followed by hydrolysis in an alkaline condition.

Forming an amide-bond or hydrolysis in an alkaline condition may be carried out by the methods as hereinbefore described.

The compounds of the formula (II) and (IV) may be prepared according to the reaction of the following Scheme (A) and (B), respectively.

In the Scheme (A) and (B), $R^{3a}$ is C1–4 alkyl, $R^{20}$ is t-butoxycarbonyl (Boc) or benzyloxycarbonyl (Cbz), $R^{30}$ is benzyl or t-butyl, $X^1$ and $X^2$ each, independently, is halogen, and the other symbols are the same meaning as hereinbefore defined.

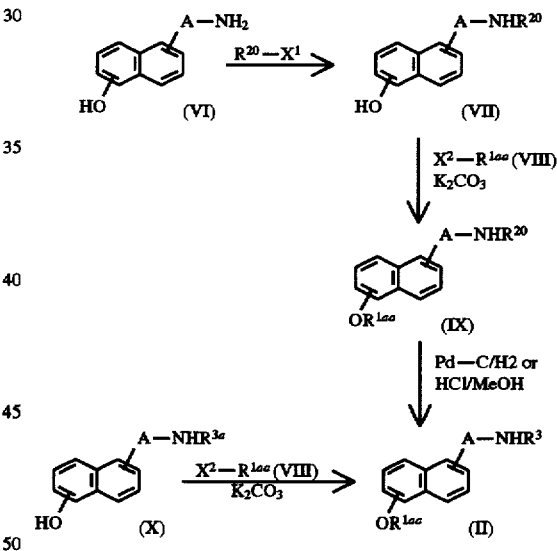

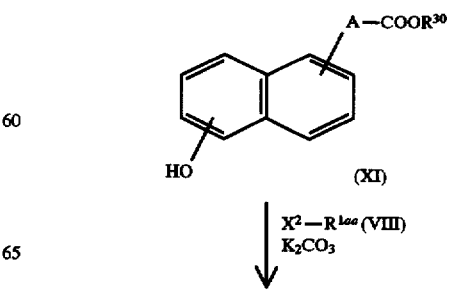

-continued
Scheme (B)

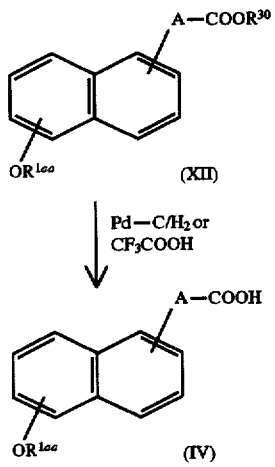

The compounds of the formula (I), wherein $R^1$ is
(C1–4 alkylene)-COOR$^{10}$,
(C1–4 alkylene)-OH,
(C1–4 alkylene)-CONR$^4$R$^5$,
(C1–4 alkylene)-CONR$^6$—(C1–4 alkylene)-OH,
(C1–4 alkylene)-NR$^4$R$^5$,
(C1–4 alkylene)-cyano or
(C1–4 alkylene)-tetrazolyl
in which all symbols are the same meaning as hereinbefore defined, i.e. the compounds of the formula (Ic)

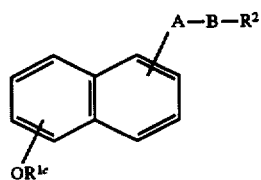

wherein, $R^{1c}$ is (C1–4 alkylene)-COOR$^{10}$, (C1–4 alkylene)-OH, (C1–4 alkylene)-CONR$^4$R$^5$, (C1–4 alkylene)-CONR$^6$-(C1–4 alkylene)-OH, (C1–4 alkylene)-NR$^4$R$^5$, (C1–4 alkylene)-cyano or (C1–4 alkylene)-tetrazolyl and the other symbols are the same meaning as hereinbefore defined may be prepared by reacting the compounds of the formula (Id)

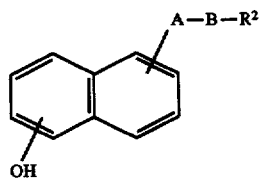

wherein all symbols are the same meaning as hereinbefore defined with the compounds of the formula $$X^3-R^{1ca}$$

wherein $X^3$ is halogen and $R^{1ca}$ is
(C1–4 alkylene)-COOR$^{10a}$,
(C1–4 alkylene)-OR$^{30a}$,
(C1–4 alkylene)-CONR$^4$R$^{5a}$,
(C1–4 alkylene)-CONR$^6$-(C1–4 alkylene)-OR$^{30a}$,
(C1–4 alkylene)-NR$^4$R$^{5a}$,
(C1–4 alkylene)-cyano,
(C1–4 alkylene)-tetrazolyl-R$^{30a}$ in which, $R^{5a}$ is C1–4 alkyl, cbz or boc, R$^{30a}$ is tetrahydropyranyl, cbz or boc, if necessary, followed by hydrolysis in an alkaline condition or by removal of the protecting group.

O-alkylation is known, and for example, this reaction may be carried out in a water-miscible organic solvent (acetone, THF or methylene chloride etc.) in the presence of a base (potassium carbonate etc.), at 0°–50° C.

The hydrolysis in an alkaline condition may be carried out by the method as hereinbefore described.

Removal of protecting group may be carried out by the known method. For example, removal of cbz may be carried out under the atmosphere of hydrogen gas, in an organic solvent (methanol, ethanol or THF etc.), by using catalyst (Pd-C, Pd or Ni etc.), at 0°–50° C. Removal of tetrahydropyranyl and boc may be carried out in a water-miscible organic solvent (methanol, ethanol, THF or dioxane etc.), by using organic acid (acetic acid, p-toluene sulfonic acid, trifluoro acetic acid or trichloro acetic acid etc.) or inorganic acid (hydrochloric acid or hydrobromic acid etc.), at 0°–90° C.

The compounds of the formula (Ic) wherein $R^{1c}$ is (C1–4 alkylene)-tetrazolyl may be prepared by reacting the compounds of the formula (Ic) wherein $R^{1c}$ is (C1–4 alkylene)-cyano with sodium azide in an organic solvent (dihydrofuran (DHF) etc.), in the presence of ammonium chloride.

The compounds of the formula (I), wherein $R^1$ is hydrogen, i.e. the compounds of the formula (Id)

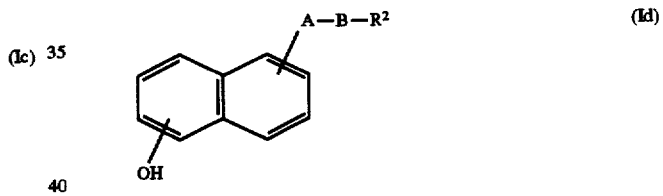

wherein all symbols are the same meaning as hereinbefore defined may be prepared from the compounds of the formula (XIII)

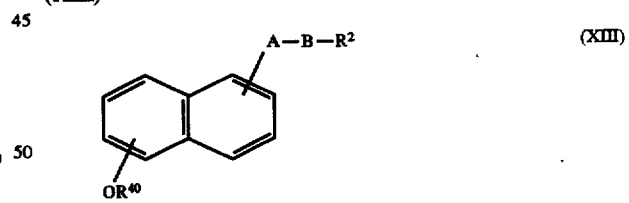

wherein $R^{40}$ is C1–4 alkyl or benzyl and the other symbols are the same meaning as hereinbefore defined, by reduction or removal of alkyl.

The reduction reaction is known, and for example, this reaction may be carried out under the condition of atmosphere of hydrogen gas, in an organic solvent (methanol, ethanol or THF etc.), in the presence of reduction catalyst (Pd-C, Pd or Ni etc.) at 0°–50° C.

The reaction of removal of alkyl is known, and for example, this reaction may be carried out in an inert organic solvent (methylene chloride or chloroform etc.) by using BBr$_3$, at 0°–50° C.

The compounds of the formula (XIII) may be prepared according to the reaction of the following Scheme (C).

Scheme (C)

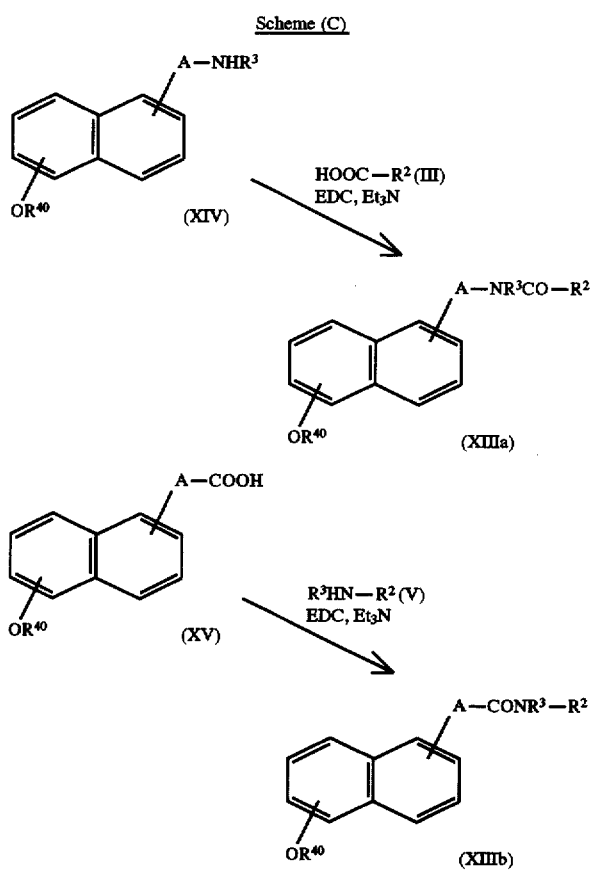

In addition, the compounds of the formulae (Ie) to (Ih) wherein corresponding $R^1$ is (C1-3 alkylene)-$CH_2OH$, (C1-3 alkylene)-$CH_2NH_2$, (C1-4 alkylene)-$CONR^4R^5$ and (C1-4 alkylene)-$CONR^6$-(C1-4 alkylene)-OH, respectively, may be prepared according to the reaction of the following Scheme (D).

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Starting materials and reagents

The starting materials and reagents in the present invention are known per se or may be prepared by known methods.

Pharmacological Activities

The compounds of the present invention of the formula (I) are useful as $PGE_2$ antagonists or agonists, because they bind onto prostaglandin $E_2$ receptors and have antagonist or agonist activity against the action thereof.

For example, in standard laboratory test, the effects of the compounds of the present invention were confirmed by inhibitory effect on binding $PGE_2$ using expression cell of mouse receptor.

Binding assay using expression cell of prostanoide receptor subtype

The preparation of membrane fraction was carried out according to the method of Sugimoto et al [J. Biol. Chem. 267, 6463-6466(1992)], using expression CHO cell of prostanoide receptor subtype (mouse $EP_3\alpha$).

The standard assay mixture contained membrane fraction (0.5 mg/ml), [$^3$H]-$PGE_2$ in a final volume of 200 ml was incubated for 1 hour at room temperature. The reaction was terminated by addition of 3 ml of ice-cold buffer. The mixture was rapidly filtered through a glass filter (GF/B). The radioactivity associated with the filter was measured by liquid scintillation counting.

Kd and Bmax values were determined from Scatchard plots [Ann. N.Y. Acad. Sci., 51, 660(1949)]. Non-specific binding was calculated as the bond in the presence of an excess (2.5 nM) of unlabeled $PGE_2$. In the experiment for competition of specific [$^3$H]-$PGE_2$ binding by the compounds of the present invention, [$^3$H]-$PGE_2$ was added at a concentration of 2.5 nM and the compounds of the present

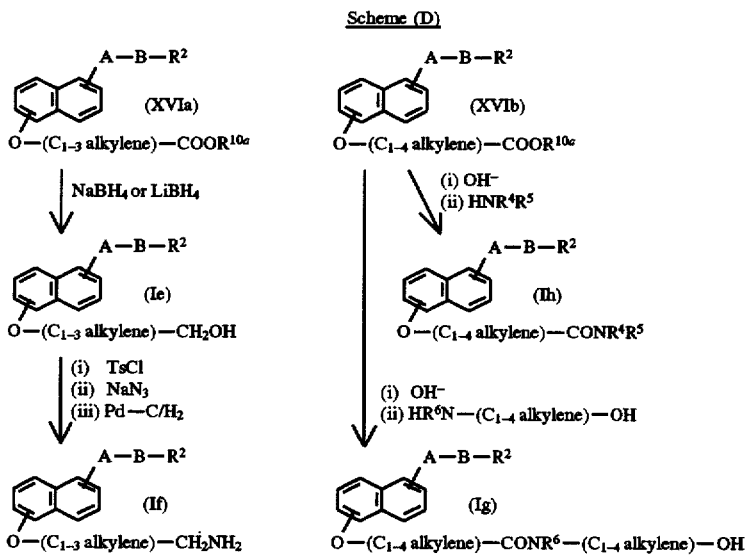

invention were at a concentration of 1 mM. The following buffer was used in all reactions.

Buffer: 10 mM potassium phosphate (pH6.0), 1 mM EDTA, 10 mM $MgCl_2$, 0.1M NaCl

The dissociation constant (Ki) of each compound was calculated by the following equation.

$$Ki=IC50/(1+([C]/Kd))$$

The results were shown in Table 50.

TABLE 50

| Ex. No. | Ki(µM) |
| --- | --- |
| 1 | 5.7 |
| 2 | 0.011 |
| 2a | 0.11 |
| 2d | 0.05 |
| 2k | 0.83 |
| 21 | 0.89 |
| 3 | 0.026 |
| 4 | 0.023 |
| 4a | 0.20 |
| 4b | 1.3 |
| 8 | 0.068 |

Toxicity

The toxicity of the compounds of the present invention are very low and therefore, it is confirmed that these compounds are safe for use as medicine.

Application for Pharmaceuticals

The compounds of the formula (I), non-toxic salts thereof, non-toxic acid addition salts thereof and hydrates thereof are useful for $PGE_2$ antagonists or agonists, because they bind onto prostaglandin $E_2$ receptors and have an activity of antagonist or agonist against the action thereof.

$PGE_2$ antagonists are considered to inhibit uterine contraction, to have an analgesic action, to inhibit digestive peristalsis or, to induce sleep, therefor they are useful for prevention and/or treatment of abortion, pain, diarrhea or insomnia.

$PGE_2$ agonists are considered to promote uterine contraction, to promote digestive peristalsis, to suppress gastric acid secretion, to lower blood pressure and inhibition of blood platelet aggregation as mentioned above. Therefore, $PGE_2$ agonists are useful as abortient, cathartics, and antiulcer, anti-gastritis, antihypertensive or antithrombosis agents.

For the purpose above described, the compounds of the formula (I), non-toxic salts thereof, non-toxic acid addition salts thereof and hydrates thereof may be normally administered systematically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 µg and 100 mg, by oral administration, up to several times per day, and between 0.1 µg and 10 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

Capsules contain hard capsules and soft capsules.

In such compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate. The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSOLBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They also be manufactured in the form of sterile solid compositions and which can be dissolved in sterile water or some other sterile diluents for injection immediately before used.

Other compositions for parenteral administration include liquids for external use, and endemic liniments, ointment, suppositories and pessaries which comprise one or more of the active compound(s) and may be prepared by know methods.

REFERENCE EXAMPLES AND EXAMPLES

The following reference examples and examples are intended to illustrate, but not limit, the present invention.

The solvents in parentheses show the developing or eluting solvents and the ratios of the solvents used are by volume in chromatographic separations. Unless otherwise specified, "NMR" was measured in a solution of dimethylsulfoxide-d (DMSO-d$_6$).

Reference example 1

[5-(2-t-butoxycarbonylethyl)naphthyl-1-oxy]acetic acid methyl ester

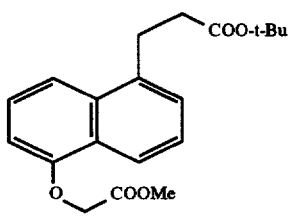

The mixture of 5-(2-t-butoxycarbonylethyl)naphth-1-ol (700 mg), methyl bromoacetate (0.29 ml), potassium carbonate (442 mg) and acetone (8 ml) was stirred overnight at room temperature. The reaction mixture was concentrated under reduced pressure. The residue was purified on silica gel chromatography to give the title compound (819 mg) having the following physical data.

TLC: Rf 0.34 (EtOAc:n-hexane=1:3);

mp :78°–79° C.

Reference example 2

[5-(2-carboxyethyl)naphthyl-1-oxy]acetic acid methyl ester.

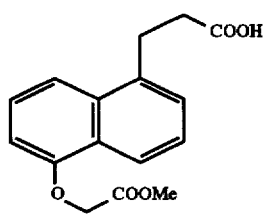

To a solution of the compound prepared in reference example 1 (605 mg) in dichloromethane (5 ml), trifluoroacetic acid (1 ml) was added. The mixture was stirred for 30 minutes at room temperature. The reaction solution was evaporated to dryness under reduced pressure to give the title compound (506 mg) having the following physical data.

mp :183°–185° C.

Example 1

[5-(2-diphenylmethylaminocarbonylethyl)naphthyl-1-oxy]acetic acid methyl ester

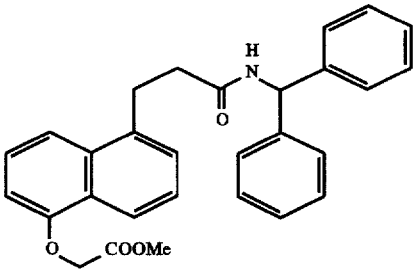

To a solution of the compound prepared in reference example 2 (327 mg), benzhydrylamine (250 mg) and 1-ethyl-3-(dimethylaminopropyl)carbodiimide hydrochloride salt (EDC.HCl) (261 mg) in dichloromethane (20 ml), 4-dimethylaminopyridine (14 mg) was added. The mixture was stirred for 3 days at room temperature. To the reaction solution, water was added. The mixture was extracted with ethyl acetate. The organic layer was washed with water and a saturated aqueous solution of sodium chloride, and dried over and concentrated under reduced pressure to give the title compound having the following physical data.

TLC: Rf 0.34 (EtOAc:benzene=1:4);

NMR (CDCl$_3$): δ8.31 (1H, m), 7.77 (1H, d), 7.45–6.98 (13H, m), 6.71 (1H, d), 6.21 (1H, d), 5.87 (1H, d), 4.82 (2H, s), 3.82 (3H, s), 3.43 (2H, t), 2.67 (2H, t).

Example 1(a)

1-methoxy-5-(2-diphenylmethylaminocarbonylethyl)naphthalene

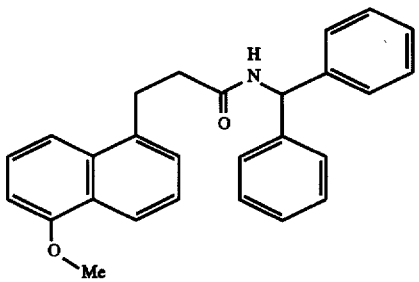

The title compound having the following physical data was obtained by the same procedure as example 1.

TLC: Rf 0.35 (n-hexane: EtOAc=2:1);

NMR (CDCl$_3$): δ8.20 (1H, m), 7.61 (1H, d), 7.47–7.18 (9H, m), 7.11–6.97 (4H, m), 6.82 (1H, d), 6.21 (1H, d), 5.88 (1H, d), 4.00 (3H, s), 3.43 (2H, d), 2.67 (2H, d).

Example 2

[5-(2-diphenylmethylaminocarbonylethyl)naphthyl-1-oxy]acetic acid

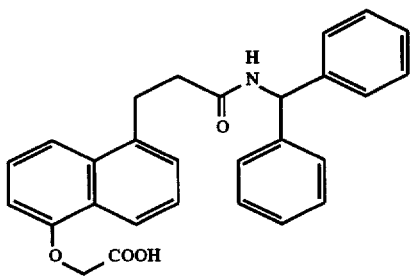

To a solution of the compound prepared in example 1 in dimethoxyethane-methanol (2:1, 10 ml), 1N aqueous solution of sodium hydroxide (2 ml) was added at 0° C. Mixture was stirred for 30 minutes at room temperature. To the reaction solution, hydrochloric acid and water were added. The obtained precipitate was filtered, washed with water and ethyl acetate and dried over under reduced pressure to give the title compound (468 mg) having the following physical data.

TLC: Rf 0.08 (MeOH:$CH_2Cl_2$=1:9);

NMR: δ8.78 (1H, d), 8.13 (1H, m), 7.67 (1H, d), 7.50–7.10 (13H, m), 6.88 (1H, d), 6.12 (1H, d), 4.87 (2H, s), 3.28 (2H, t), 2.62 (2H, t).

Example 2(a)–2(o)

The compounds having the following physical data were obtained by the same procedure as the series of reactions of reference example 1 and 2 and example 1 and 2.

Example 2(a)

[5-[2-(3,3-diphenylcarbazoyl)ethyl]naphthyl-1-oxy]acetic acid

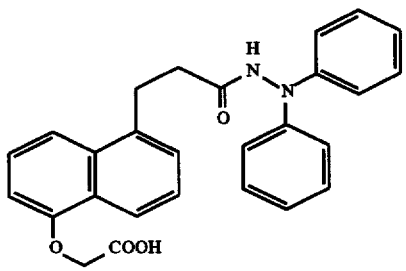

TLC: Rf 0.08 (MeOH:$CH_2Cl_2$=1:9);

NMR: δ10.32 (1H, s), 8.04 (1H, dd), 7.56 (1H, d), 7.40–6.6 (14H, m), 4.73 (2H, s), 3.32 (2H, t), 2.48 (2H, t).

Example 2(b)

[5-(diphenylmethylaminocarbonylmethoxy)naphthyl-1-oxy]acetic acid

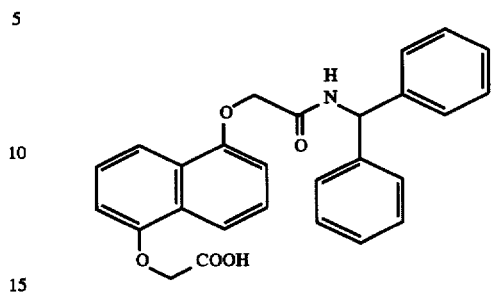

TLC: Rf 0.51 (MeOH:$CH_2Cl_2$=1:4);

NMR: δ9.09 (1H, d), 7.82 (2H, d), 7.5–7.2 (12H, m), 6.92 (1H, d), 6.91 (1H, d), 6.21 (1H, d), 4.85 (2H, s), 4.83 (2H, s), 3.35 (1H, br).

Example 2(c)

[5-[(3,3-diphenylcarbazoyl)methoxy]naphthyl-1-oxy]acetic acid

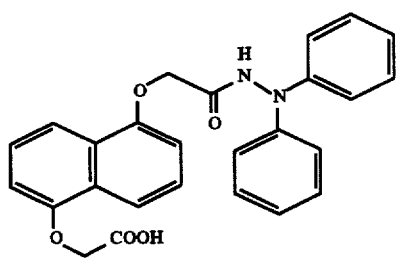

TLC: Rf 0.46 (MeOH:$CH_2Cl_2$=1:4);

NMR: δ10.96 (1H, s), 7.98 (1H, d), 7.86 (1H, d), 7.44 (1H, t), 7.42 (1H, t), 7.28 (4H, t), 7.12 (4H, d), 7.1–6.9 (4H, m), 4.90 (2H, s), 4.87 (2H, s), 3.34 (1H, br).

Example 2(d)

[5-(diphenylmethylaminocarbonylmethyl)naphthyl-1-oxy]acetic acid

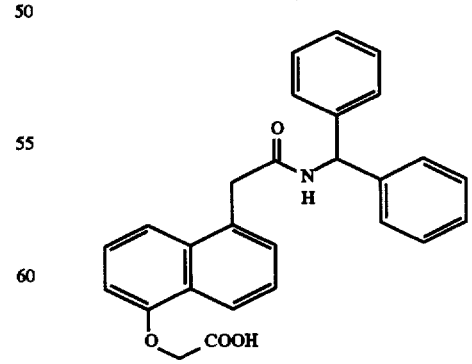

TLC: Rf 0.35 (MeOH:$CHCl_3$=3:7);

NMR: δ13.00 (1H, brs), 9.17 (1H, d), 8.17 (1H, dd), 7.70 (1H, d), 7.50–7.17 (13H, m), 6.87 (1H, d), 6.12 (1H, d), 4.86 (2H, s), 4.02 (2H, s).

Example 2(e)

[5-(diphenylmethylaminocarbonyl)naphthyl-1-oxy]acetic acid

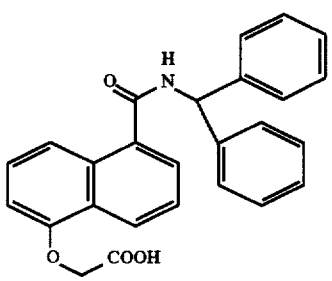

TLC: Rf 0.19 (MeOH:CH$_2$Cl$_2$=1:5);

NMR (CDCl$_3$+CD$_3$OD): δ8.40 (1H, d), 8.29 (1H, s), 7.87 (1H, d), 7.53 (1H, d), 7.48–7.20 (11H, m), 6.82 (1H, d), 6.50 (1H, s), 4.80 (2H, s).

Example 2(f)

[6-(diphenylmethylaminocarbonylmethyl)naphthyl-1-oxy]acetic acid

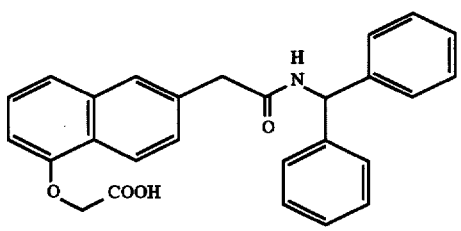

TLC: Rf 0.30 (MeOH:CH$_2$Cl$_2$=1:4);

NMR: δ9.10 (1H, d), 8.13 (1H, d), 7.72 (1H, s), 7.52–7.17 (13H, m), 6.82 (1H, dd), 6.13 (1H, d), 4.86 (2H, s), 3.73 (2H, s).

Example 2(g)

(6-(phenylmethylaminocarbonylmethyl)naphthyl-1-oxy]acetic acid

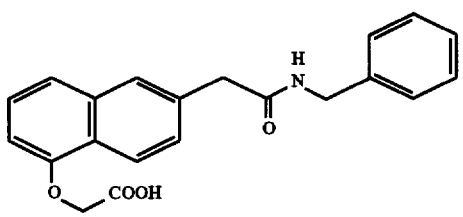

TLC: Rf 0.23 (MeOH:CH$_2$Cl$_2$=1:4);

NMR: δ8.61 (1H, t), 8.15 (1H, d), 7.73 (1H, s), 7.50–7.13 (8H, m), 6.84 (1H, d), 4.87 (2H, s), 4.30 (2H, d), 3.67 (2H, s).

Example 2(h)

[5-(2-phenylmethylaminocarbonylethyl)naphthyl-1-oxy]acetic acid

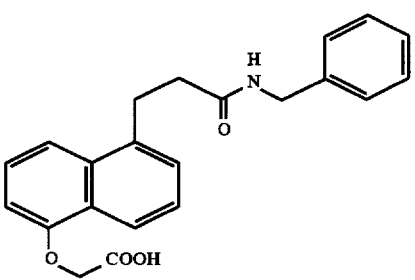

TLC: Rf 0.28 (MeOH:CHCl$_3$=3:7);

NMR(DMSO-d6+CDCl$_3$): δ8.27–8.12 (2H, m), 7.69 (1H, d), 7.48–7.10 (8H, m), 6.79 (1H, d), 4.79 (2H, s), 4.30 (2H, d), 3.35 (2H, t), 2.60 (2H, t).

Example 2(i)

[5-(diphenylmethylaminocarbonyl)naphthyl-1-oxy]acetic acid

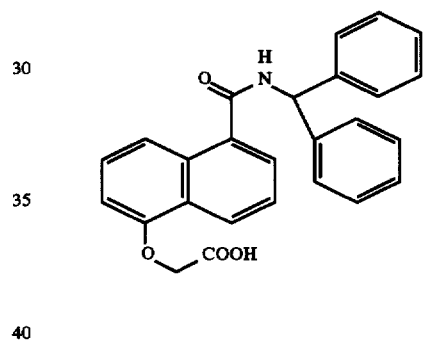

TLC: Rf 0.15 (MeOH:CH$_2$Cl$_2$=1:5);

NMR (CDCl$_3$+CD$_3$OD): δ8.49 (1H, d), 7.78 (1H, d), 7.65 (1H, d), 7.53–7.20 (12H, m), 6.79 (1H, d), 6.54 (1H, s), 4.79 (2H, s).

Example 2(j)

[6-(2-diphenylmethylaminocarbonylethyl)naphthyl-1-oxy]acetic acid

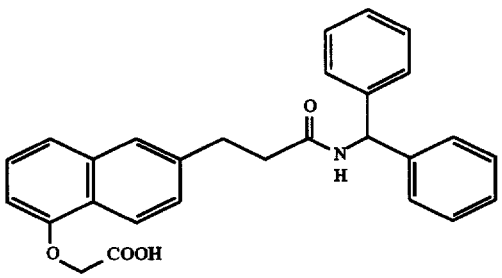

TLC: Rf 0.30 (MeOH:CHCl$_3$=3:7);

NMR: δ8.77 (1H, d), 8.13 (1H, d), 7.66 (1H, s), 7.43–7.06 (13H, m), 6.83 (1H, m), 6.09 (1H, d), 4.90 (2H, s), 3.03 (2H, t), 2.64 (2H, t).

Example 2(k)

[5-[2-((1R)-1-phenylethyl)aminocarbonylethyl]naphthyl-1-oxy]acetic acid

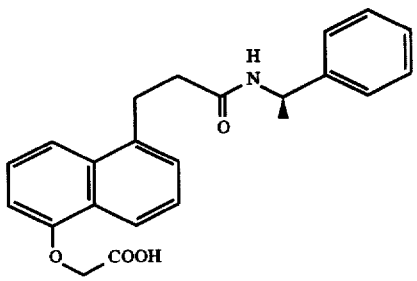

TLC: Rf 0.21 (CHCl$_3$:MeOH=20:1);

NMR: δ13.18–12.92 (1H, br), 8.30 (1H, d), 8.18 (1H, d), 7.63 (1H, d), 7.40–7.18 (8H, m), 6.89 (1H, d), 5.00–4.89 (1H, m), 4.88 (2H, s), 3.31–3.22 (2H, m), 2.52–2.49 (2H, m), 1.31 (3H, d).

Example 2(l)

[5-[2-((1S)-1-phenylethyl)aminocarbonylethyl]naphthyl-1-oxy]acetic acid

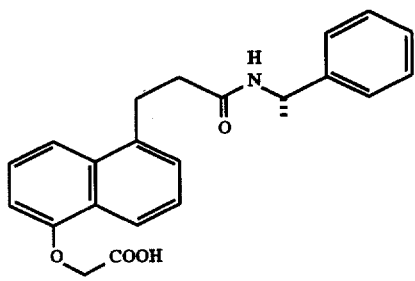

TLC: Rf 0.21 (CHCl$_3$:MeOH=20:1);

NMR: δ13.18–12.92 (1H, br), 8.30 (1H, d), 8.18 (1H, d), 7.63 (1H, d), 7.40–7.18 (8H, m), 6.89 (1H, d), 5.00–4.89 (1H, m), 4.88 (2H, s), 3.31–3.22 (2H, m), 2.52–2.49 (2H, m), 1.31 (3H, d).

Example 2(m)

[5-[2-[1-phenyl-1-(3-pyridyl)methyl]aminocarbonylethyl]naphthyl-1-oxy]acetic acid

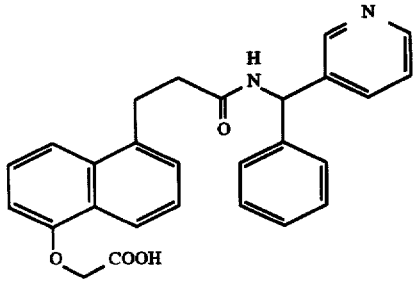

TLC: Rf 0.22 (CHCl$_3$:MeOH=20:1);

NMR: δ8.82 (1H, d), 8.17 (1H, d), 7.61(1H, d), 7.40–7.18 (13H, m), 6.75 (1H, d), 6.14 (1H, d), 4.34 (2H, s), 2.59 (2H, t), 2.50–2.49 (2H, m).

Example 2(n)

[5-[2-(N-diphenylmethyl-N-ethylaminocarbonyl)ethyl]naphthyl-1-oxy]acetic acid

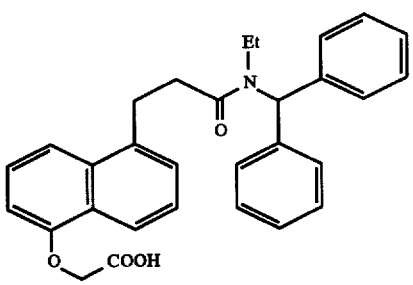

TLC: Rf 0.28 (CHCl$_3$:MeOH=20:1);

NMR: δ8.12–7.99 (2H, m), 7.39–7.06 (8H, m), 6.99–6.95 (4H, m), 6.85–6.59 (2H, m), 4.45 (2H, s), 3.94–3.38 (4H, m), 2.81–2.59 (2H, m), 0.46–0.18 (3H, m).

Example 2(o)

[5-[2-(diphenylmethylaminocarbonyl)vinyl]naphthyl-1-oxy]acetic acid

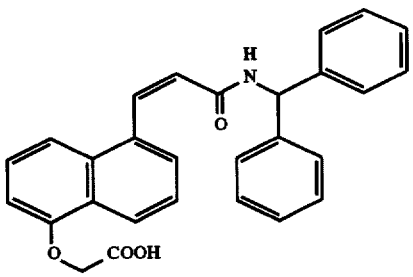

TLC: 0.50 (CHCl$_3$:MeOH:AcOH=93:5:2);

NMR: δ9.15 (1H, d), 8.32 (1H, d), 8.23 (1H, d), 7.81 (1H, d), 7.76 (1H, d), 7.57 (1H, dd), 7.50 (1H, dd), 7.40–7.20 (10H, m), 6.96 (1H, d), 6.92 (1H, d), 6.32 (1H, d), 4.89 (2H, s).

Example 3

2-[5-(2-diphenylmethylaminocarbonylethyl)naphthyl-1-oxy]ethanol

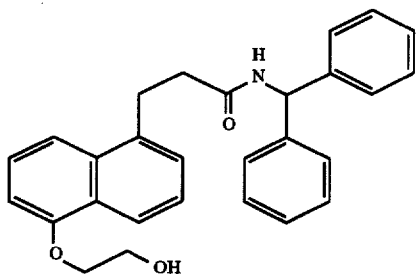

To a solution of the compound prepared in example 1 (750 mg) in methanol-THF (10 ml+6ml), sodium boro hydride (125 mg) was added. The mixture was stirred for 2 hours at 60° C. After termination of reaction, 1N hydrochloric acid was added to the reaction mixture. The mixture was extracted with methylene chloride. The organic layer was washed with a saturated aqueous solution of sodium chloride, dried over and concentrated under reduced pressure. The residue was purified on silica gel chromatography to give the title compound (600 mg) having the following physical data:

TLC: Rf 0.40 (EtOH : $CH_2Cl_2$=3:7);

NMR ($CDCl_3$):δ8.21 (1H, m), 7.65 (1H, d, J=8 Hz), 7.45–7.17 (9H, m), 7.13–6.98 (4H, m), 6.85 (1H, d, J=8 Hz), 6.22 (1H, d, J=8 Hz), 5.86 (1H, d, J=8 Hz), 4.28 (2H, t, J=4 Hz), 4.12 (2H, m), 3.45 (2H, t, J=7 Hz), 2.68 (2H, t, J=7 Hz), 2.14 (1H, t, J=7 Hz).

Example 4

[5-(2-diphenylmethylaminocarbonylethyl)naphthyl-1-oxy]acetic acid amide

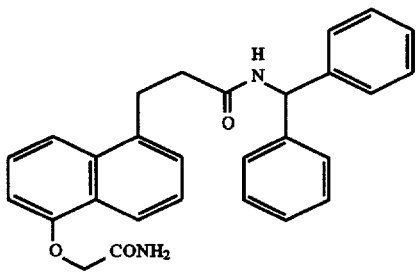

To a solution of the compound prepared in example 1 (75 mg) in THF (1 ml), conc. aqueous solution of ammonia (0.2 ml) was added. The mixture was stirred for 10 hours at room temperature. The reaction solution was diluted with methylene chloride, washed with 1N hydrochloric acid and a saturated aqueous solution of sodium chloride, dried over and concentrated under reduced pressure. The residue was purified on silica gel chromatography to give the title compound having the following physical data:

TLC: Rf 0.46 ($CHCl_3$:MeOH=9:1);

NMR:δ8.79 (1H, d, J=9 Hz), 8.28 (1H, m), 7.69 (1H, d, J=9 Hz), 7.64–7.14 (15H, m), 6.90 (1H, d, J=7 Hz), 6.13 (1H, d, J=9 Hz), 4.62 (2H, s), 3.32 (2H, m), 2.63 (2H, t, J=8 Hz).

Example 4(a)

N,N-dimethyl-[5-(2-diphenylmethylaminocarbonylethyl)naphthyl-1-oxy]acetic acid amide

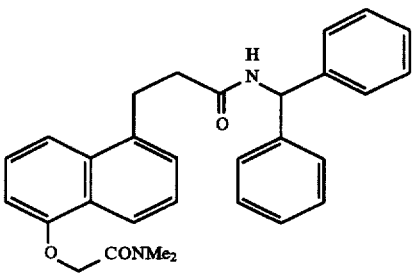

The title compound having the following physical data was obtained by the same procedure as example 4.

TLC: Rf 0.58 ($CHCl_3$:MeOH=9:1);

NMR ($CDCl_3$): δ8.22 (1H, m), 7.64 (1H, d, J=8 Hz), 7.43–7.16 (9H, m), 7.12–7.00 (4H, m), 6.83 (1H, d, J=8 Hz), 6.22 (1H, d, J=8 Hz), 6.08 (1H, d, J=8 Hz), 4.83 (2H, s), 3.42 (2H, t, J=8 Hz), 3.12 (3H, s), 2.97 (3H, s), 2.66 (2H, t, J=8 Hz).

Example 4(b)

N-(2-hydroxyethyl)-[5-(2-diphenylmethylaminocarbonylethyl)naphthyl-1-oxy]acetic acid amide

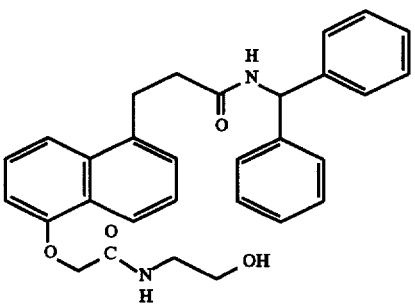

The title compound having the following physical data was obtained by the same procedure as example 4.

TLC: Rf 0.44 ($CHCl_3$:MeOH=9:1);

NMR ($CDCl_3$): δ8.14 (1H, m), 7.72 (1H, d, J=9 Hz), 7.50–7.34 (3H, m), 7.34–7.18 (6H, m), 7.14–6.98 (5H, m), 6.82 (1H, d, J=7 Hz), 6.22 (1H, d, J=8 Hz), 5.89 (1H, d, J=8 Hz), 4.71 (2H, s), 3.77 (2H, m), 3.56 (2H, t, J=5 Hz), 3.46 (2H, t, J=8 Hz), 2.69 (2H, t, J=8 Hz), 2.24 (1H, t, J=5 Hz).

Example 5

2-[5-(2-diphenylmethylaminocarbonylethyl)naphthyl-1-oxy]ethylamine

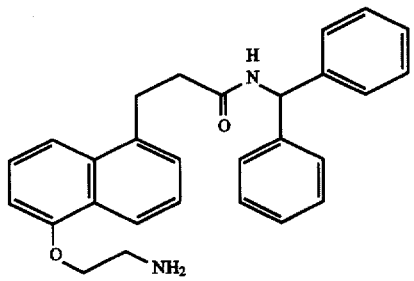

To a solution of compound prepared in example 3 (51 mg) in pyridine (1 ml), tosyl chloride (30 mg) was added. The mixture was stirred for 1 hour at room temperature. The reaction solution was diluted with methylene chloride, washed with 1N hydrochloric acid, a saturated aqueous solution of sodium hydrogencarbonate and a saturated aqueous solution of sodium chloride, dried over and concentrated under reduced pressure. To a solution of the residue (65 mg) in dimethylformamide (DMF), sodium azide (16 mg) was added. The mixture was refluxed with heating for 4 hours. After cooling the reaction mixture, the reaction mixture was diluted with water and extracted with methylene chloride. The organic layer was washed with water, dried over and concentrated under reduced pressure. To a solution of the residue (48 mg) in methanol (2 ml), Pd—C (10 mg; 10%) was added. The mixture was stirred under an atmosphere of hydrogen gas for 1 night at room temperature. Reaction solution was filtered and concentrated under reduced pressure. The residue was purified on silica gel chromatography to give the title compound (31 mg) having the following physical data.

TLC: Rf 0.28 (MeOH: CHCl$_3$=3:7);

NMR (CDCl$_3$): δ8.20 (1H, m), 7.62 (1H, d, J=8 Hz), 7.43–6.97 (13H, m), 6.81 (1H, d, J=8 Hz), 6.21 (1H, d, J=8 Hz), 6.01 (1H, d, J=8 Hz), 4.14 (2H, t, J=5 Hz), 3.45 (2H, t, J=7 Hz), 3.19 (2H, t, J=5 Hz), 2.67 (2H, t, J=7 Hz), 1.50 (2H, s).

Reference example 3

1-benzyloxy-5-[2-(diphenylmethylcarbonylamino)ethyl]naphthalene

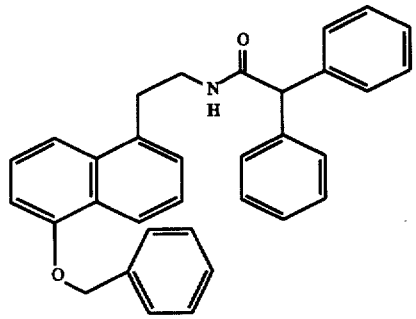

To a solution of diphenylacetic acid (0.171 g) in methylene chloride (10 ml), dimethylaminopyridine (0.01 g) and 1-benzyloxy-5-(2-aminoethyl)naphthalene (0.196 g) were added at room temperature. After 10 minutes, EDC. HCl (0.154 g) was added to the mixture solution. The mixture was stirred overnight at room temperature for 1 night. After termination of reaction, water and methylene chloride were added to the reaction mixture. The organic layer was washed with a saturated aqueous solution of ammonium chloride, water and a saturated aqueous solution of sodium chloride, dried over and concentrated under reduced pressure. The residue was purified on silica gel chromatography to give the title compound (0.172 g) having the following physical data.

TLC: Rf 0.42 (EtOAc: n-hexane=1:2).

Example 6

5-[2-(diphenylmethylcarbonylamino)ethyl]naphth-1-ol

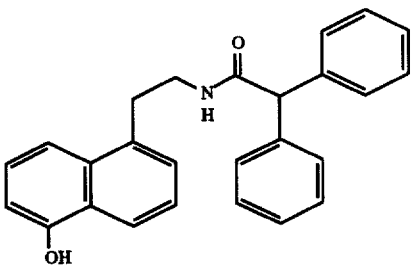

Under an atmosphere of hydrogen gas, the mixture of the compound prepared in reference example 3 (0.168 g), Pd—C (0.1 g; 10%) and methanol (20 ml) was stirred vigorously for 3 hours at room temperature. The reaction mixture was filtered and concentrated under reduced pressure to give the title compound (0.13 g) having the following physical data.

TLC: Rf 0.26 (EtOAc: n-hexane=1:2).

Example 7

[5-[2-(diphenylmethylcarbonylamino)ethyl]naphthyl-1-oxy]acetic acid methyl ester

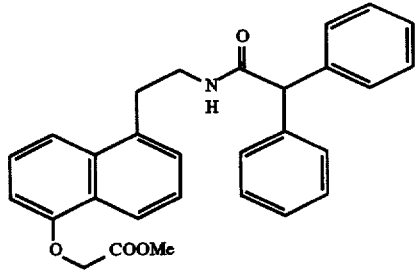

To a solution of the compound prepared in example 6 (0.128 g) in acetone (15 ml), potassium carbonate (0.056 g) and methyl bromoacetate (0.062 g) were added at room temperature. The reaction solution was stirred for overnight at room temperature. The reaction solution was filtered and concentrated under reduced pressure. The residue was purified by recrystalization from ethyl acetate-hexane solvent to give the title compound (0.073 g) having the following physical data.

TLC: Rf 0.48 (EtOAc: benzene=1:5).

Example 8

[5-[2-(diphenylmethylcarbonylamino)ethyl]naphthyl-1-oxy]acetic acid

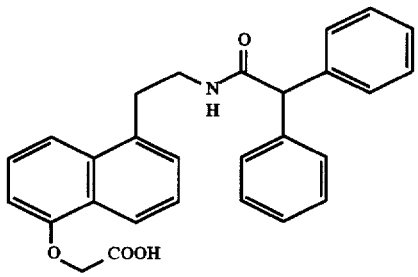

By using the compound prepared in example 7 (0.067 g), the title compound (0.05 g) having the following physical data was obtained by the same procedure as example 2.

TLC: Rf 0.22 (MeOH:CH$_2$Cl$_2$=1:5);

NMR (CDCl$_3$+CD$_3$OD): δ826 (1H, d), 7.65 (1H, d), 7.40–7.00 (13H, m), 6.75 (1H, d), 627–6.10 (1H, m), 4.85 (1H, s), 4.80 (2H, s), 3.80–3.40 (2H, m) 3.22 (2H, t).

Example 9

5-(2-diphenylmethylaminocarbonylethyl)naphth-1-ol

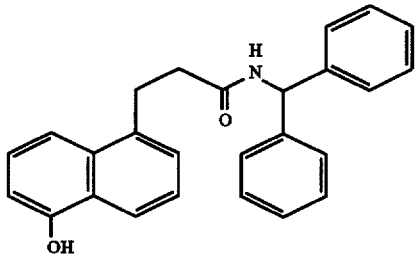

To a solution of the compound prepared in example 1(a) in methylene chloride (50 ml), BBr$_3$ (0.96 ml) was added dropwise at 0° C. The reaction solution was stirred for 30 minutes at room temperature. The reaction solution was poured into iced water and extracted with ethyl acetate. The organic layer was washed with a saturated aqueous solution of sodium hydrogencarbonate and a saturated aqueous solution of sodium chloride, dried over and concentrated under reduced pressure. The residue was purified by recrystalization (ethyl acetate-hexane) to give the title compound (1.62 g) having the following physical data.

TLC: Rf 0.20 (n-hexane : EtOAc=2:1);

NMR δ10.07 (1H, s), 8.79 (1H, d), 8.05 (1H, m), 7.53 (1H, d), 7.40–7.16 (13H, m), 6.88 (1H, d), 6.14 (1H, d), 3.38 (2H, d), 2.63 (2H, d).

Example 10

1-cyanomethoxy-5-(2-diphenylmethylaminocarbonylethyl)naphthalene

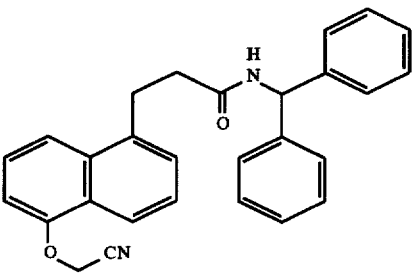

By using the compound prepared in example 9, the title compound having the following physical data was obtained by the same procedure as example 7.

TLC: Rf 0.30 (n-hexane:EtOAc=7:3);

NMR (CDCl$_3$): δ8.12 (1H, t-like), 7.77 (1H, d), 7.46 (1H, d), 7.41–7.38 (2H, m), 7.29–7.24 (6H, m), 7.07–7.03 (4H, m), 6.93 (1H, d), 6.21 (1H, d), 5.92–5.79 (1H, m), 4.97 (3H, s), 3.46 (2H, t), 2.68 (2H, t).

Example 11

1-tetrazolylmethoxy-5-(2-diphenylmethylaminocarbonylethyl)naphthalene

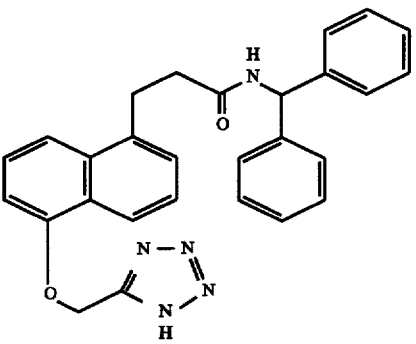

To a solution of the compound prepared in example 10 (420 mg) in DHF (2 ml), sodium azido (72 mg) and ammonium chloride (59 mg) were added. The mixture was stirred for 12 hours at 120° C. To the reaction solution, water (2 ml) was added. The mixture solution was adjusted to pH2 by adding conc. hydrochloric acid. The obtained precipitate was collected with filter, washed with iced water and ether and dried over under reduced pressure to give the title compound (391 mg) having the following physical data.

TLC: Rf 0.31 (CHCl$_3$:MeOH=20:1);

NMR : δ8.67 (1H, d), 8.03 (1H, t-like), 7.58 (1H, d), 7.37 (1H, d), 7.29–6.89 (13H, m), 6.00 (1H, d), 5.56 (3H, s), 3.17 (2H, t), 2.51 (3H, t).

Example 12

1-methoxy-5-[2-[1-phenyl-1-(3-chlorophenyl)
methyl]aminocarbonylethyl]naphthalene

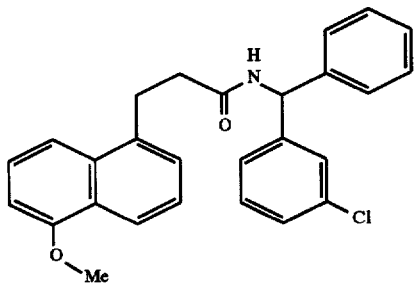

By using [1-phenyl-1-(3-chlorophenyl)methyl]amine instead of benzhydrylamine in example 1, the title compound having the following physical data was obtained by the same procedure as example 1.

TLC: Rf 0.50 (n-hexane: EtOAc=1:1);

NMR (CDCl$_3$): δ8.20 (1H, m), 7.62 (1H, d), 7.52–6.80 (13H, m), 6.16 (1H, d), 5.80 (1H, d), 4.02 (3H, s), 3.45 (2H, t), 2.69 (2H, t).

Example 13

5-[2-[1-phenyl-1-(3-chlorophenyl)methyl]
aminocarbonylethyl]naphth-1-ol

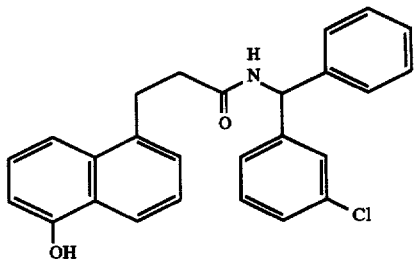

By using the compound prepared in example 12, the title compound having the following physical data was obtained by the same procedure as example 9.

TLC: Rf 0.41 (n-hexane: EtOAc=1:1);

NMR: δ10.05 (1H, s), 8.82 (1H, d), 8.03 (1H, m), 7.52 (1H, d), 7.40–7.15 (12H, m), 6.88 (1H, d), 6.15 (1H, d), 3.27 (2H, t), 2.63 (2H, t).

Example 14

1-cyanomethoxy-5-[2-[1-phenyl-1-(3-chlorophenyl)
methyl]aminocarbonylethyl]naphthalene

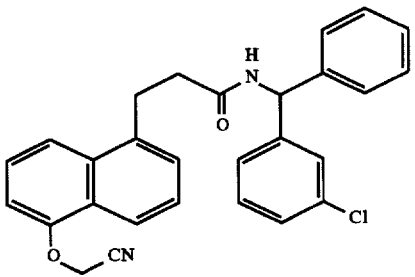

By using the compound prepared in example 13, the title compound having the following physical data was obtained by the same procedure as example 7.

TLC: Rf 0.30 (EtOAc: benzene=3:17);

NMR (CDCl$_3$): δ8.13 (1H, m), 7.76 (1H, d, J=8 Hz), 7.52–6.86 (13H, m), 6.16 (1H, d, J=8 Hz), 5.90 (1H, d, J=8 Hz, NH), 4.97 (2H, s, —OCH$_2$), 3.44 (2H, t, J=7 Hz), 2.67 (2H, t, J=7 Hz).

Example 15

(5-[2-[1-phenyl-1-(3-chlorophenyl)methyl]
aminocarbonylethy]naphthyl-1-oxy]-acetic acid
methyl ester

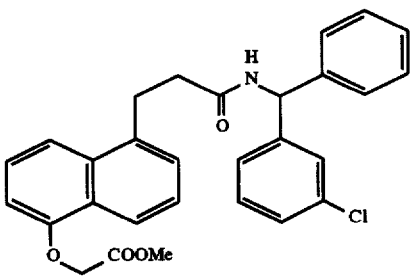

By using the compound prepared in example 13, the title compound having the following physical data was obtained by the same procedure as example 7.

TLC: Rf 0.33 (EtOAc benzene=3:17);

NMR (CDCl$_3$): δ8.27 (1H, m), 7.67 (1H, d, J=8 Hz), 7.50–6.87 (12H, m), 6.71 (1H, d, J=8 Hz), 6.16 (1H, d, J=8 Hz), 5.83 (1H, d, J=8 Hz, NH), 4.82 (2H, s, —OCH$_2$), 3.83 (3H, s, —OCH$_3$), 3.44 (2H, t, J=7 Hz), 2.67 (2H, t, J=7 Hz).

Example 16

[5-[2-[1-phenyl-1-(3-chlorophenyl)methyl]aminocarbonylethyl]naphthyl-1-oxy]-acetic acid

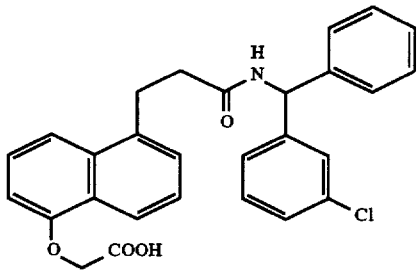

By using the compound prepared in example 15, the title compound having the following physical data was obtained by the same procedure as example 2.

TLC: Rf 0.18 (MeOH:CHCl$_3$=1:4);

NMR: δ13.07 (1H, brs, COOH), 8.82 (1H, d, J=8 Hz, NH), 8.13 (1H, m), 7.67 (1H, d, J=8 Hz), 7.50–7.11 (12H, m), 6.87 (1H, d, J=8 Hz), 6.15 (1H, d, J=8 Hz), 4.86 (2H, s, —OCH$_2$), 3.30 (2H, t, J=7 Hz), 2.63 (2H, t, J=7 Hz).

Formulation example

Formulation example 1

The following compounds were admixed in conventional method and punched out to obtain 100 tablets each containing 5 mg of active ingredient.

| | |
|---|---|
| [5-(2-diphenylmethylaminocarbonylethyl)naphthyl-1-oxy] acetic acid methyl ester (compound of example 1) | 500 mg |
| Carboxymethylcellulose calcium | 200 mg |
| Magnesium stearate | 100 mg |
| Micro crystalline cellulose | 9.2 g |

For us, what we claim is:

1. A naphthyloxyacetic acid derivative of the formula (1)

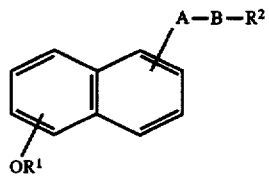
(I)

wherein

R$^1$ is (C1–4 alkylene)-COOR$^{10}$ in which R$^{10}$ is hydrogen or C$_{1-4}$ alkyl, A is a single bond, C1–6 alkylene, C2–6 alkenylene, —S-(C1–6 alkylene) or —O-(C1–6 alkylene), B is NR$^3$CO or CONR$^3$ in which, R$^3$ is hydrogen or C1–4 alkyl, and R$^2$ is (i) C1–6 alkyl, (ii) C2–6 alkenyl, (iii) C1–6 alkyl substituted by 1–3 of substituent(s) selected from the group consisting of phenyl, C4–7 cycloalkyl, and naphthyl, (iv) C2–6 alkenyl substituted by 1–3 of substituent(s) selected from the group consisting of phenyl, C4–7 cycloalkyl and naphthyl, (v) NR$^{7a}$R$^{8a}$ in which R$^{7a}$ and R$^{8a}$ each, independently, is phenyl, C4–7 cycloalkyl or naphthyl, or (vi) (C1–6 alkylene)-NR$^{7a}$R$^{8a}$ in which R$^{7a}$ and R$^{8a}$ are the same meaning as hereinbefore defined, with the proviso that the ring in R$^2$ may be substituted by 1–3 of C1–4 alkyl, C1–4 alkoxy, halogen, nitro or trifluoromethyl; or non-toxic salt thereof, non-toxic acid addition salt thereof and hydrate thereof.

2. A compound according to claim 1, which is

[5-(2-diphenylmethylaminocarbonylethyl)naphthyl-1-oxy] acetic acid,

[5-(diphenylmethylaminocarbonylmethoxy)naphthyl-1-oxy]acetic acid,

[5-(diphenylmethylaminocarbonylmethyl)naphthyl-1-oxy] acetic acid,

[5-(diphenylmethylaminocarbonyl)naphthyl-1-oxy]acetic acid,

[6-(diphenylmethylaminocarbonylmethyl)naphthyl-1-oxy] acetic acid, (6-(phenylmethylaminocarbonylmethyl)naphthyl-1-oxy] acetic acid,

[5-(2-phenylmethylaminocarbonylethyl)naphthyl-1-oxy] acetic acid,

[5-(diphenylmethylaminocarbonyl)naphthyl-1-oxy]acetic acid,

[6-(2-diphenylmethylaminocarbonylethyl)naphthyl-1-oxy] acetic acid,

[5-[2-((1R)-1-phenylethyl)aminocarbonylethyl]naphthyl-1-oxy]acetic acid,

[5-[2-((1S)-1-phenylethyl)aminocarbonylethyl]naphthyl-1-oxy]acetic acid,

[5-[2-(N-diphenylmethyl-N-ethylaminocarbonyl)ethyl] naphthyl-1-oxy]acetic acid,

[5-[2-(diphenylmethylaminocarbonyl)vinyl]naphthyl-1-oxy]acetic acid,

[5-[2-(diphenylmethylcarbonylamino)ethyl]naphthyl-1-oxy]acetic acid or

[5-[2-[1-phenyl-1-(3-chlorophenyl)methyl]aminocarbonylethyl]naphthyl-1-oxy]-acetic acid or methyl ester thereof.

3. A pharmaceutical composition which comprises an effective amount of a naphthyloxyacetic acid derivative of the formula (I) depicted in claim 1, non-toxic salt thereof, non-toxic acid addition salt thereof or hydrate thereof and pharmaceutically acceptable carrier and/or coating.

4. A method for treating and/or preventing abortion, pain, diarrhea, cathartics, ulcer, gastritis, hypertension and thrombosis, or for induction of abortion or sleep, which comprises administering an effective amount of a naphthyloxyacetic acid derivative of the formula (I) depicted in claim 1, non-toxic salt thereof, non-toxic acid addition salt thereof or hydrate thereof and pharmaceutically acceptable carrier and/or coating.

* * * * *